United States Patent
Neya et al.

(10) Patent No.: US 7,872,097 B2
(45) Date of Patent: Jan. 18, 2011

(54) CYCLIC PEPTIDE COMPOUNDS

(75) Inventors: Masahiro Neya, Tokyo (JP); Seiji Yoshimura, Tokyo (JP); Kazunori Kamijyo, Tokyo (JP); Takuya Makino, Tokyo (JP); Minoru Yasuda, Tokyo (JP); Toshio Yamanaka, Tokyo (JP); Eisaku Tsujii, Tokyo (JP); Yukiko Yamagishi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 263 days.

(21) Appl. No.: 12/083,551

(22) PCT Filed: Oct. 26, 2006

(86) PCT No.: PCT/JP2006/321924

§ 371 (c)(1),
(2), (4) Date: Apr. 14, 2008

(87) PCT Pub. No.: WO2007/049803

PCT Pub. Date: May 3, 2007

(65) Prior Publication Data

US 2009/0170755 A1    Jul. 2, 2009

Related U.S. Application Data

(60) Provisional application No. 60/730,011, filed on Oct. 26, 2005, provisional application No. 60/751,204, filed on Dec. 19, 2005.

(51) Int. Cl.
*C07K 7/64* (2006.01)

(52) U.S. Cl. .......................... 530/317; 530/328; 514/11

(58) Field of Classification Search .................. 530/317, 530/328; 514/11
See application file for complete search history.

(56) References Cited

U.S. PATENT DOCUMENTS 6,927,208 B1    8/2005    Wenger et al.

FOREIGN PATENT DOCUMENTS

| WO | WO 00/01715 | 1/2000 |
|---|---|---|
| WO | WO 02/32447 A2 | 4/2002 |
| WO | WO 2005/021028 A1 | 3/2005 |
| WO | WO 2005/032576 A1 | 4/2005 |
| WO | WO 2006/038088 A1 | 4/2006 |
| WO | WO 2006/039668 A2 | 4/2006 |
| WO | WO 2006/054801 A1 | 5/2006 |

OTHER PUBLICATIONS

Soo Y. Ko, "Solid-Phase Total Synthesis of Cyclosporine Analogues", Helvetica Chimica Ada, vol. 80, (1997), pp. 695-705.
Marian E. Major, et al., "Hepatitis C Viruses", Virology 4th Edition, pp. 1127-1161, (2001).
Qui-Lim Choo et al., "Isolation of a cDNA Clone Derived from a Blood-Borne Non-A, Non-B Viral Hepatitis Genome", Science, vol. 244, pp. 359-362, (1989).
Markus Thall et al., "Functional Association of Cyclophilin A with HIV-1 Virions", Nature, vol. 372, pp. 363-365, (1994).
K Inoue et al., "Antiviral Effect of Cyclosporin A on HCV Propagation", NIH, Jun. 1989, 6th International Symposium on Hepatitis C and Related Virus.
Marina Berenguer et al., "HCV-Related Fibrosis Progression Following Liver Transplantation: Increase in Recent Years", Journal of Hepatology, vol. 32, (2000), pp. 673-684.
Koichi Watashi et al., "Cyclosporin A Suppresses Replication of Hepatitis C Virus Genome in Cultured Hepatocytes", J. Hepatology, vol. 38, No. 5, pp. 1282-1288 (2003).
Mina Nakagawa et al., "Specific Inhibition of Hepatitis C Virus Replication by Cyclosporin A", Biochemical and Biophysical Research, vol. 313, No. 1, pp. 42-47 (2004).
Kazutoshi Sakamoto et al., "Taxonomy of the Producing Organism, Fermentation, Isolation, Physico-Chemical Properties and Biological Activities", The Journal of Antibiotics, vol. 46, No. 12, pp. 1788-1798 (1993).
Office Action dated Mar. 10, 2010, in corresponding Israeli Application No. 190286, Examiner A. Fleider.
Office Action dated May 27, 2010, in corresponding Russian Application No. 2008116674, Examiner M. E. Gorbatovskaya.
Official Action in corresponding Russian Application No. 2008116674, apparent mailing date: Sep. 13, 2010.

*Primary Examiner*—David Lukton
(74) *Attorney, Agent, or Firm*—Finnegan, Henderson, Farabow, Garrett & Dunner, L.L.P.

(57) ABSTRACT

The present invention relates to a new cyclic peptide compound or a salt thereof, which has anti-hepatitis C virus activities based on inhibitory activity against the RNA replication of hepatitis C virus replicon, to a process for preparation thereof comprising a rearrangement reaction under a mild acidic condition and the following amino acid changing reactions etc., to a pharmaceutical composition comprising the same, and to a method for prophylactic and/or therapeutic treatment of hepatitis C in a human being or an animal.

11 Claims, No Drawings

CYCLIC PEPTIDE COMPOUNDS

CROSS REFERENCE TO RELATED APPLICATIONS

This application is an national phase application based on PCT/JP2006/321924, filed Oct. 26, 2006, and claims the benefit of U.S. Provisional Application Nos. 60/730,011, filed Oct. 26, 2005; and 60/751,204, filed Dec. 19, 2005, the contents of each of which is incorporated herein by reference.

TECHNICAL FIELD

The present invention relates to a new cyclic peptide compound or a salt thereof having inhibitory activity against the RNA replication of hepatitis C virus (hereafter referred to as HCV) replicon. In particular, the present invention relates to a new cyclic peptide compound or a salt thereof, to a process for preparation thereof, to a pharmaceutical composition comprising the new cyclic peptide compound or a salt thereof, and to a method for the prophylactic and/or therapeutic treatment of hepatitis C in a human being or animal.

BACKGROUND ART

The estimated number of HCV carriers is about 170 million worldwide (about 3%) and about 1.5 million in Japan. Even in the combination therapy of using interferon (hereafter referred to as IFN) and ribavirin (Virazole), available as a first option for treatment, its effectiveness is 40% for all types of HCV. Furthermore, its effectiveness is only 15 to 20% for IFN-resistant virus (genotype 1b), particularly abundantly found in Japan. On the other hand, the combination therapy has side effects frequently. It is thus difficult to get rid of the virus completely by using currently available treatment methods. In the case when chronic hepatitis cannot be cured completely, the hepatitis will securely develop into cirrhosis hepatitis (30%) or hepatocellular carcinoma (25%). In Europe and the United States, hepatitis C has been a major indication for liver transplant. However, the redevelopment of HCV occurs frequently even in transplanted livers. For these reasons, the needs for new agents being improved in both effectiveness and safety, having higher antiviral effects and capable of inhibiting hepatitis C are very strong in society.

HCV is a virus having plus-strand RNA as a gene and is classified into Flaviviridae in accordance with the analysis of the base sequence of the gene. According to Fields Virology fourth edition, D. Knipe et al ed., Philadelphia, Lippincott Williams & Wilkins 2001, 1127-1161, although the existence of HCV was anticipated in 1970s, the discovery of HCV was very difficult. HCV was called non-A non-B hepatitis virus for many years. In 1989, according to Choo Q-L et al., Science 244, 359-362 (1989), part of the gene of this virus was cloned from the serum of an infected laboratory animal, and its cDNA sequence was identified and confirmed, whereby the virus was named "HCV."

DISCLOSURE OF THE INVENTION

Cyclosporin A is used as an immunosuppressant for organ transplant. M. Thali et al., Nature 372, 363-365 (1994) reported that Cyclosporin A had anti-HIV activity by inhibiting the interaction between Cyclosporin A and the virus particle forming protein of Human Immunodeficiency Virus Type 1 (HIV-1). R. M. Wenger et al. reported in WO00/01715 that their novel cyclosporins has the anti-HIV activity. Furthermore, K. Inoue et al., 6th International Symposium on Hepatitis. C and Related Virus, 3-6. June (2000) Bethesda, Md., USA reported that Cyclosporin A had an anti-HCV activity, however, reports for supporting this finding are not presented by other groups up until now. And HIJIKATA et al. reported in WO2005/021028 that their modified cyclosporins have the anti-HCV activity.

M. Berenguer et al., J. Hepatol 32, 673-684 (2000) reported that the clinical use of Cyclosporin A serving as an immunosuppressant caused. HCV to multiply in transplant patients.

Hence, an anti-hepatitis C agent improved in the activity, transition in blood, selectivity and the side effects, for example, in comparison with Cyclosporin A, has been demanded because of the above-mentioned reasons.

Further, in order to convert the skeleton of the Cyclosporine compounds, it needs some severe conditions such as high temperature or high pressure. On the other hand, the conversion of the starting compound (FR901459 compound) to our compounds by a rearrangement reaction in the present invention needs the mild acidic condition because of the hydroxyl group on the 2-position of the starting compound.

The object cyclic peptide compound in the present invention is a new compound, and can be represented by the following general formula (I):

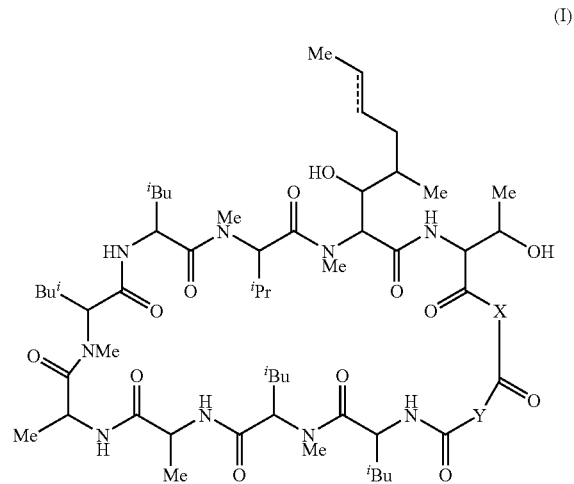

wherein
X is

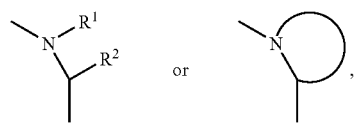

in which
$R^1$ is hydrogen or lower alkyl;
$R^2$ is hydrogen, aryl or lower alkyl which is optionally substituted by a suitable substituent selected from the group consisting of:
hydroxy, cyclo(lower)alkyl, lower alkoxy, aryl, aryl (lower)alkoxy, optionally substituted carbamoyloxy, and optionally substituted amino;

and

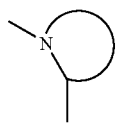

is N-containing heterocyclic group;

Y is

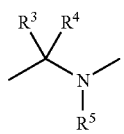 or 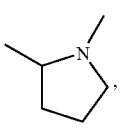, in which

R³ is cyclo(lower)alkyl, aryl, optionally substituted heterocyclic group or lower alkyl which is optionally substituted by a suitable substituent selected from the group consisting of:

hydroxy, cyclo(lower)alkyl, lower alkoxy, aryl, aryl(lower)alkoxy, lower alkoxy(lower)alkoxy, optionally substituted amino and —OC(O)NR⁶R⁷ (wherein R⁶ and R⁷ are each independently hydrogen or lower alkyl, or alternatively R⁶ and R⁷, together with the nitrogen-atom to which they attached, represent N-containing heterocyclic group which is optionally substituted by a lower alkyl);

and

R⁴ and R⁵ are each independently hydrogen or lower alkyl;

and

═════represents single bond or double bond;

or a salt thereof, with proviso, when R² is hydrogen, R³ is cyclo(lower)alkyl, aryl, optionally substituted heterocyclic group, lower alkoxymethyl, aryl(lower)alkyl, t-butyl, sec-butyl, cyclo(lower)alkyl(lower)alkyl, or ethyl substituted by a suitable substituent selected from the group consisting of hydroxy, lower alkoxy, aryl(lower)alkoxy, lower alkoxy(lower)alkoky, optionally substituted amino and —OC(O)NR⁶R⁷ (wherein R⁶ and R⁷ are each as defined above).

Preferred embodiments of the object compound (I) are as follows.

1) The compound of the general formula (I), wherein

X is

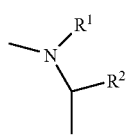

in which

R¹ is hydrogen or lower alkyl;

and

R² is aryl or lower alkyl which is optionally substituted by a suitable substituent selected from the group consisting of:

hydroxy, cyclo(lower)alkyl, lower alkoxy, aryl, aryl(lower)alkoxy, di(lower)alkylcarbamoyloxy, and amino which is optionally substituted by one or two suitable substituent(s) selected from the group consisting of:

lower alkyl, benzyloxycarbonyl and t-butoxycarbonyl;

and

Y is

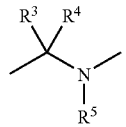 or 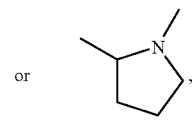

in which

R³ is cyclo(lower)alkyl, aryl, or lower alkyl which is optionally substituted by a suitable substituent selected from the group consisting of hydroxy, lower alkoxy, and aryl(lower)alkoxy;

R⁴ is hydrogen;

and

R⁵ is lower alkyl;

or a salt thereof.

2) The compound of 1), wherein

R¹ is lower alkyl;

R² is lower alkyl;

Y is

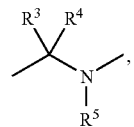, in which

R³ is aryl or lower alkyl which is optionally substituted by hydroxy or lower alkoxy;

R⁴ is hydrogen;

and

R⁵ is lower alkyl;

and

═════moiety is double bond;

or a salt thereof.

3) The compound of 2), wherein

R³ is lower alkyl which is optionally substituted by hydroxy or lower alkoxy;

or a salt thereof.

4) The compound of the general formula (I),
  wherein
  X is

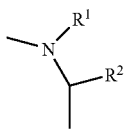

in which
    R¹ is lower alkyl;
    and
    R² is hydrogen;
  and
  Y is

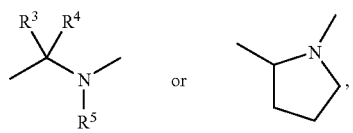

in which
    R³ is cyclo(lower)alkyl, aryl, heterocyclic group which is optionally substituted by lower alkoxy carbonyl, (lower)alkoxy(lower)alkyl, aryl(lower)alkyl, t-butyl, sec-butyl, cyclo(lower)alkyl(lower)alkyl, or ethyl substituted by a suitable substituent selected from the group consisting of:
      hydroxy, lower alkoxy, aryl(lower)alkoxy, lower alkoxy(lower)alkoxy, —OC(O)NR⁶R⁷ (wherein R⁶ and R⁷ are each independently hydrogen or lower alkyl, or alternatively R⁶ and R⁷, together with the nitrogen atom to which they attached, represent N-containing heterocyclic group which is optionally substituted by a lower alkyl),
      and amino which is optionally substituted by one or two suitable substituent(s) selected from the group consisting of:
        lower alkyl and benzyloxycarbonyl;
    and
    R⁴ and R⁵ are each independently hydrogen or lower alkyl;
  or a salt thereof.

5) The compound of 4),
  wherein
  Y is

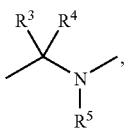

in which
    R³ is cyclo(lower)alkyl, aryl, heterocyclic group which is optionally substituted by lower alkoxy carbonyl, t-butyl, sec-butyl, or ethyl substituted by a suitable substituent selected from the group consisting of:
      hydroxy, lower alkoxy, aryl(lower)alkoxy, lower alkoxy(lower)alkoxy, and —OC(O)NR⁶R⁷ (wherein R⁶ and R⁷ are each independently hydrogen or lower alkyl, or alternatively R⁶ and R⁷, together with the nitrogen atom to which they attached, represent N-containing heterocyclic group which is optionally substituted by a lower alkyl);
    R⁴ is hydrogen
    and
    R⁵ is lower alkyl;
  and
  =====moiety is double bond;
  or a salt thereof.

6) The compound of the general formula (I),
  wherein
  X is

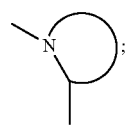

and
  Y is

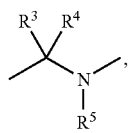

in which
    R³ is lower alkyl;
    and
    R⁴ and R⁵ are each independently hydrogen or lower alkyl;
  or a salt thereof.

7) The compound of 6),
  wherein
  X is

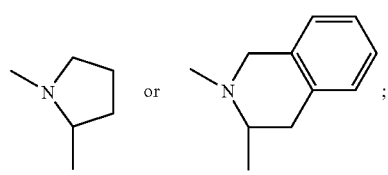

R⁴ is hydrogen;
  R⁵ is lower alkyl;
  and
  =====moiety is double bond;
  or a salt thereof.

The compound (I) or a salt thereof in the present invention can be prepared by the processes as illustrated in the following reaction schemes.

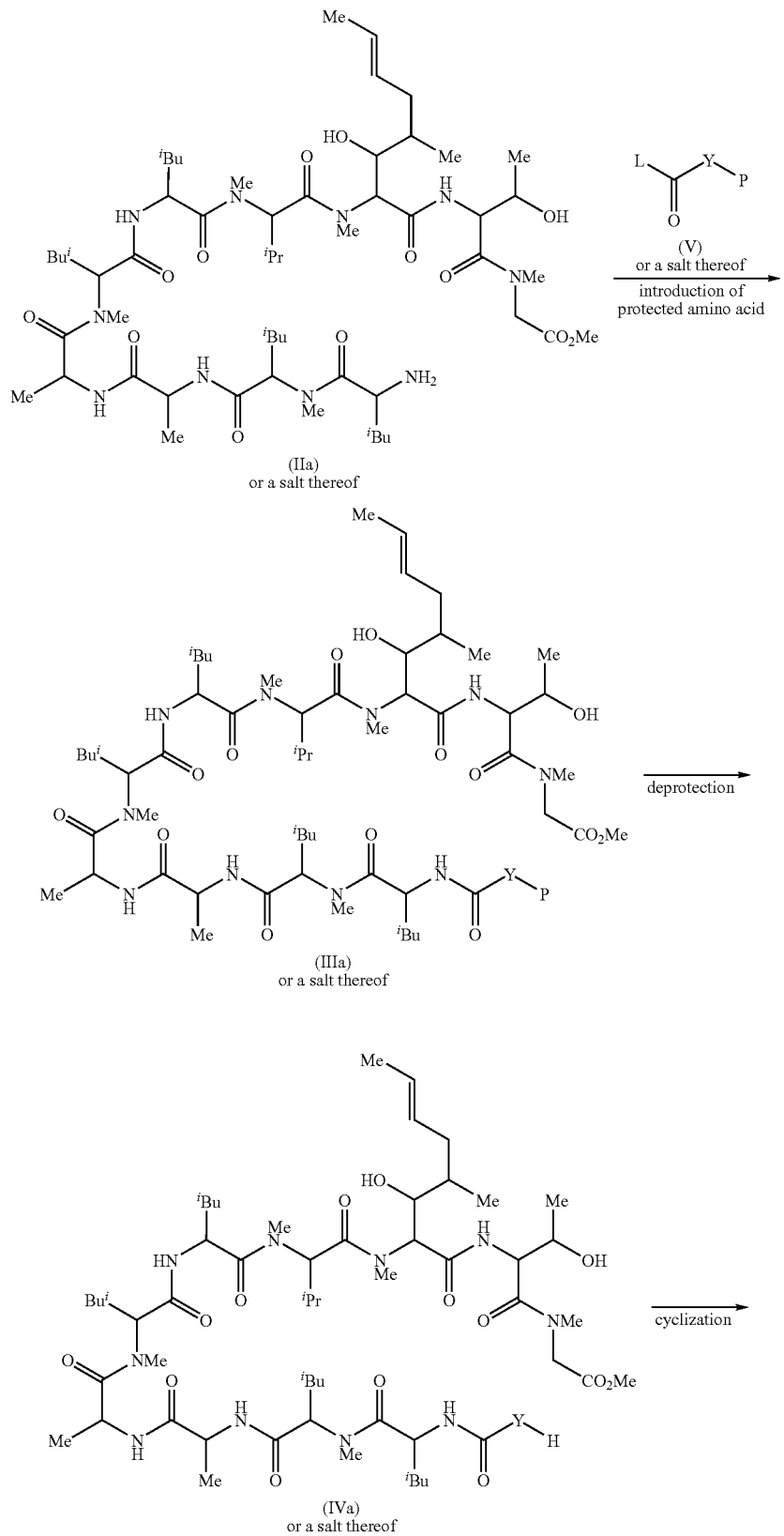

-continued
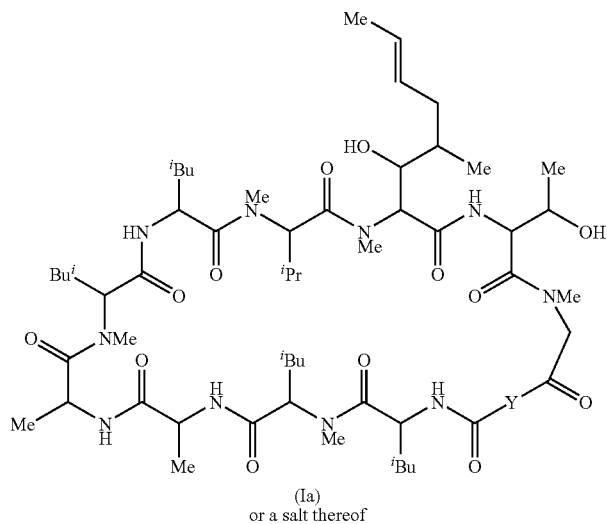
(Ia)
or a salt thereof
Process 2
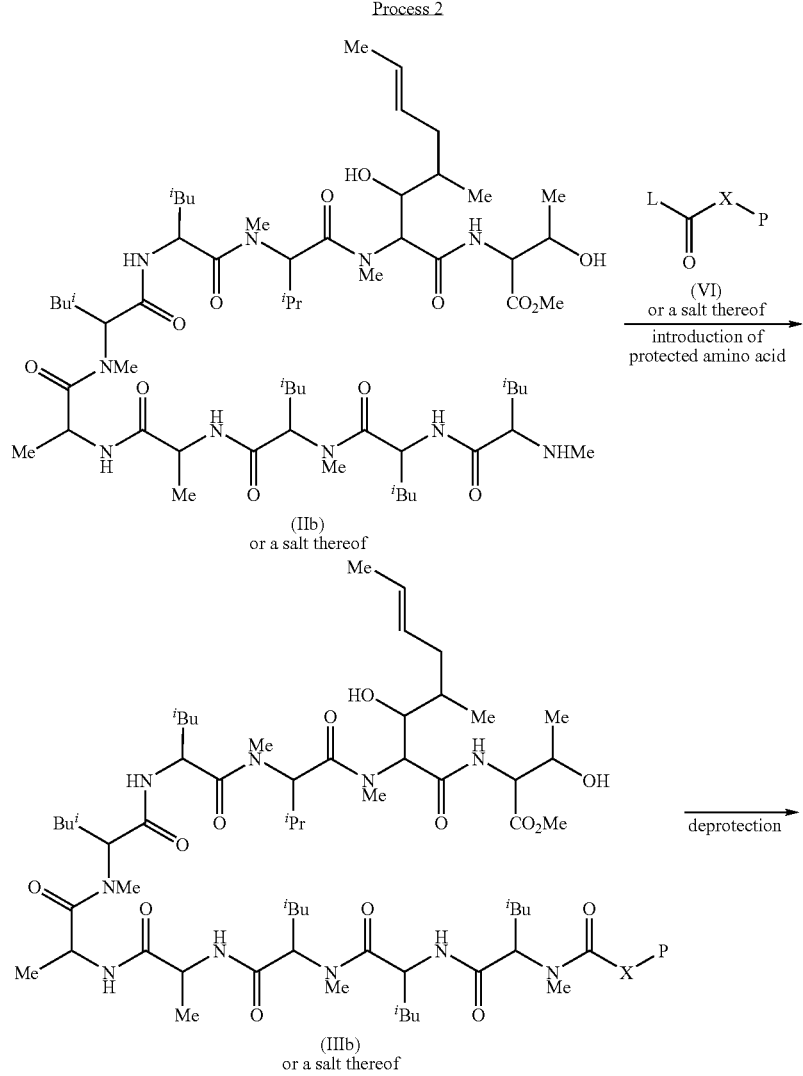

-continued
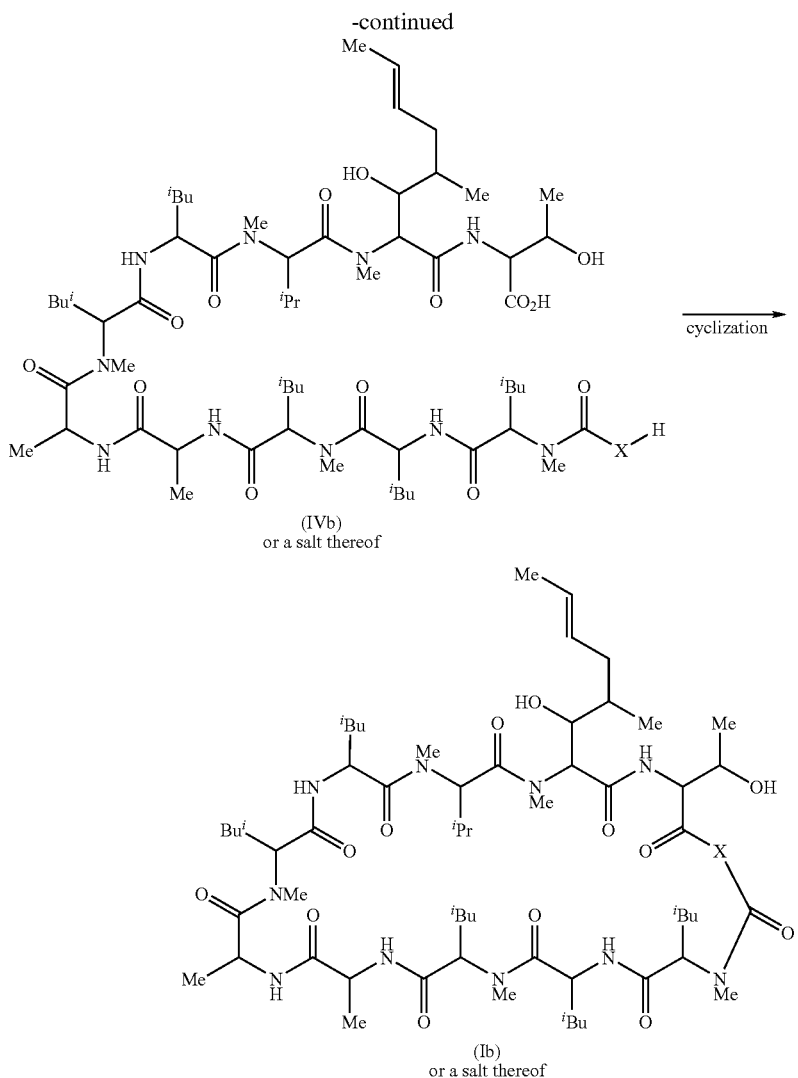
(IVb) or a salt thereof
cyclization
(Ib) or a salt thereof
Process 3
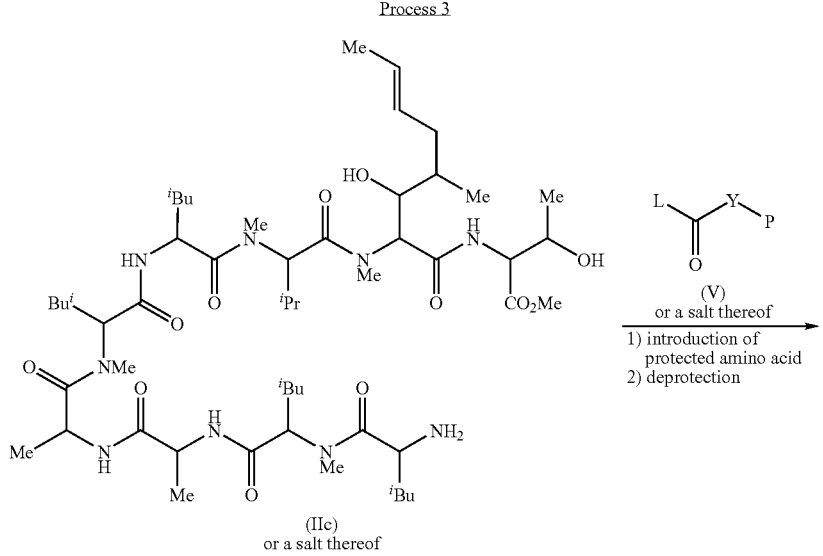
(IIc) or a salt thereof
(V) or a salt thereof
1) introduction of protected amino acid
2) deprotection -continued
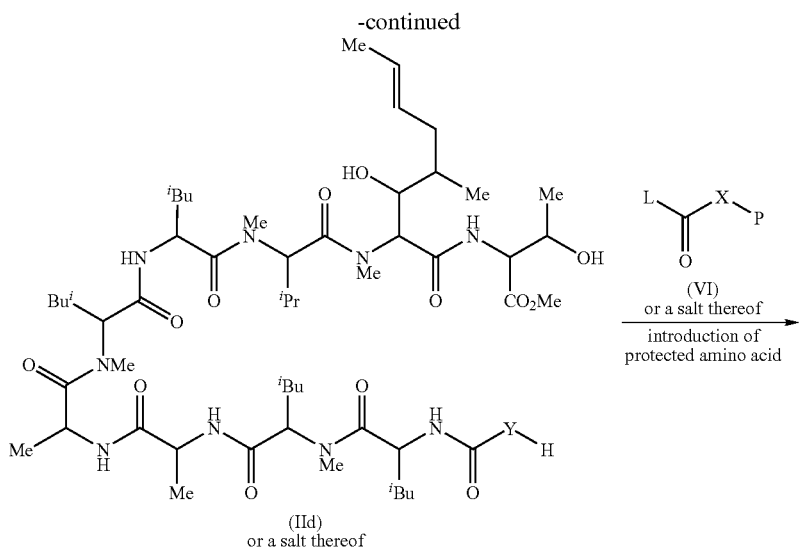
(IId) or a salt thereof
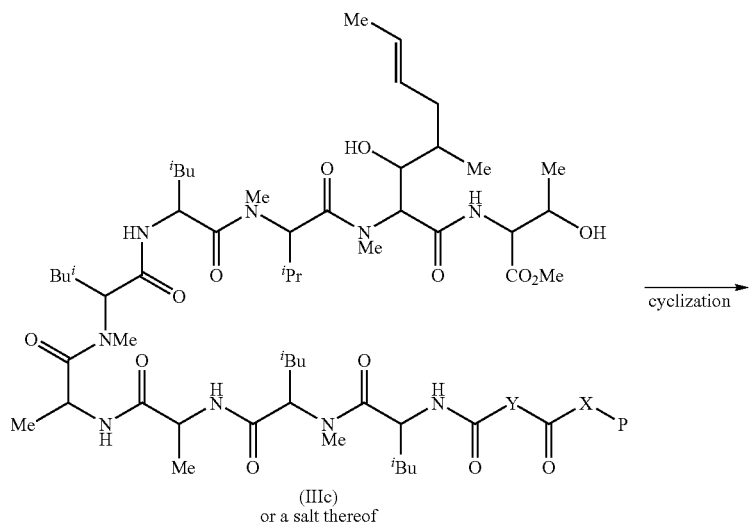
(IIIc) or a salt thereof
(Ic) or a salt thereof Process 4
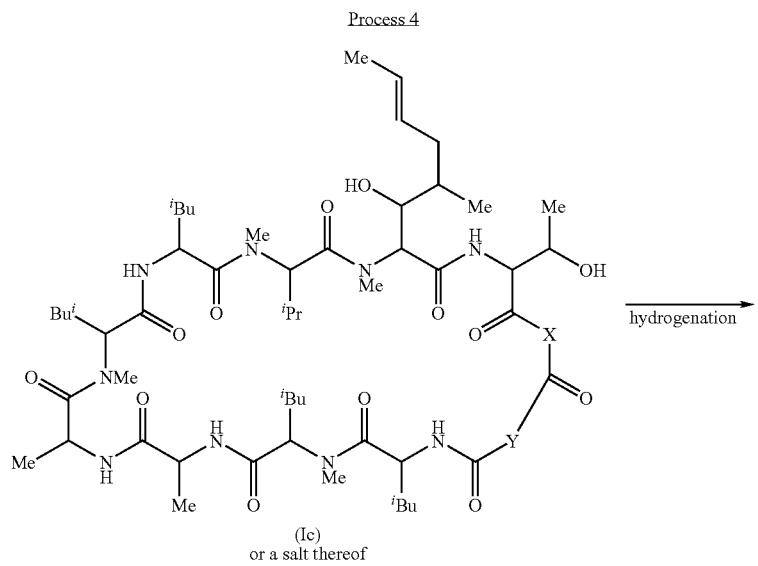
(Ic)
or a salt thereof
hydrogenation →
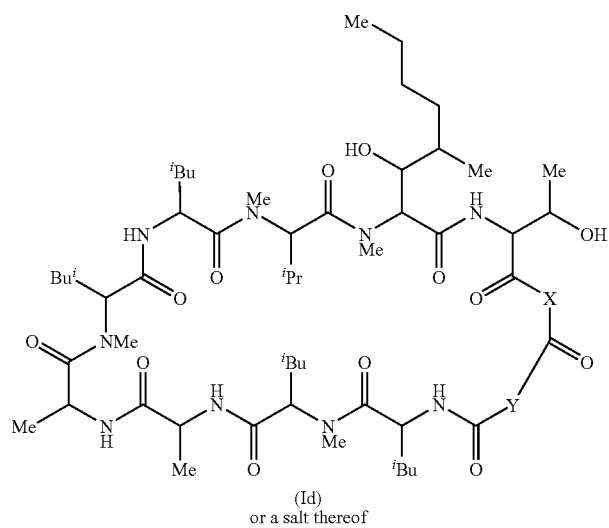
(Id)
or a salt thereof
The starting compounds or a salt thereof in the present invention can be prepared, for example, by the processes as illustrated in the following reaction schemes.

Process A
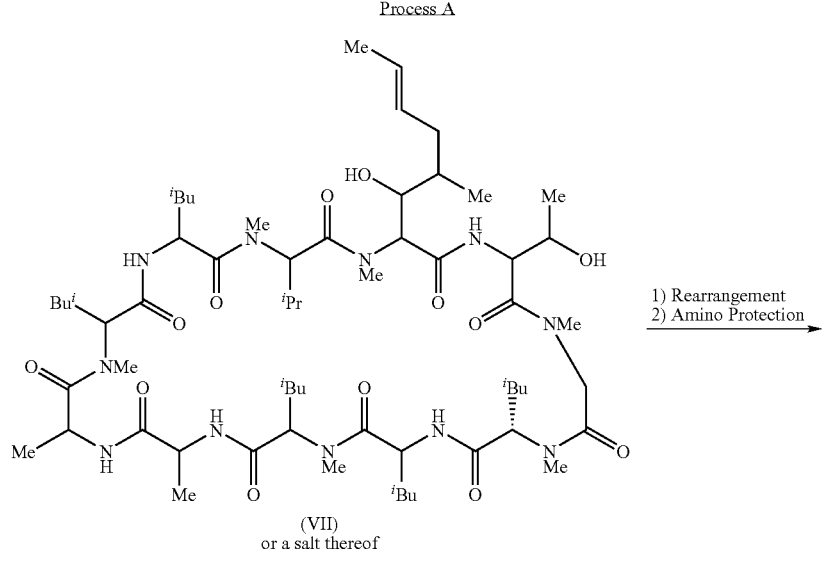
(VII)
or a salt thereof
1) Rearrangement
2) Amino Protection
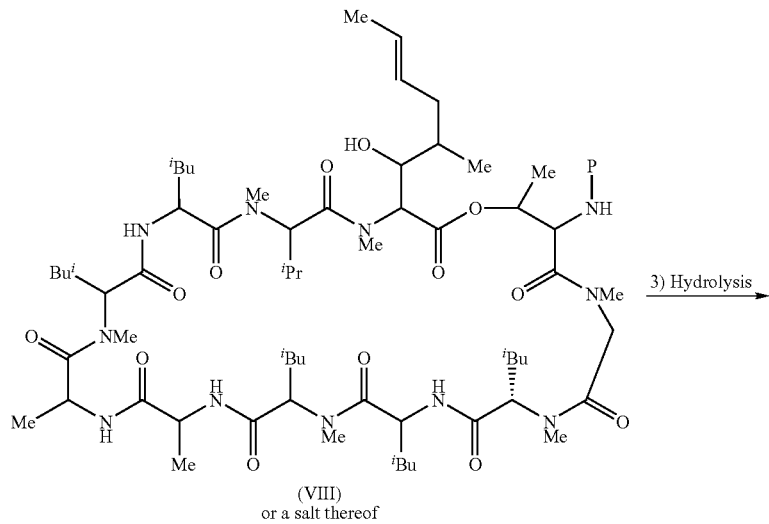
(VIII)
or a salt thereof
3) Hydrolysis
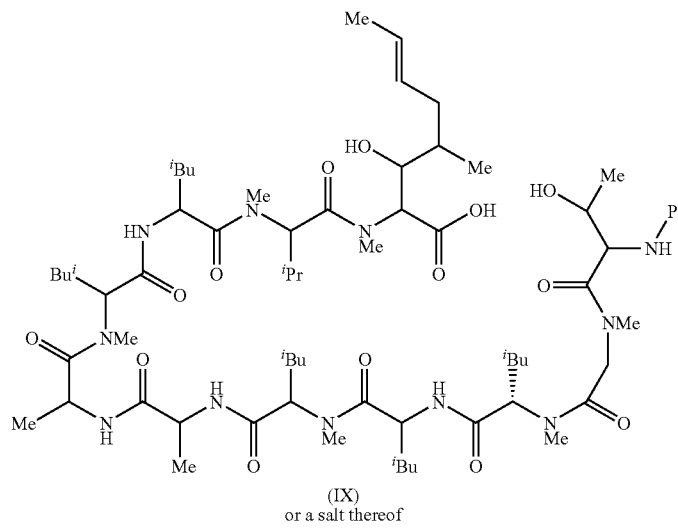
(IX)
or a salt thereof

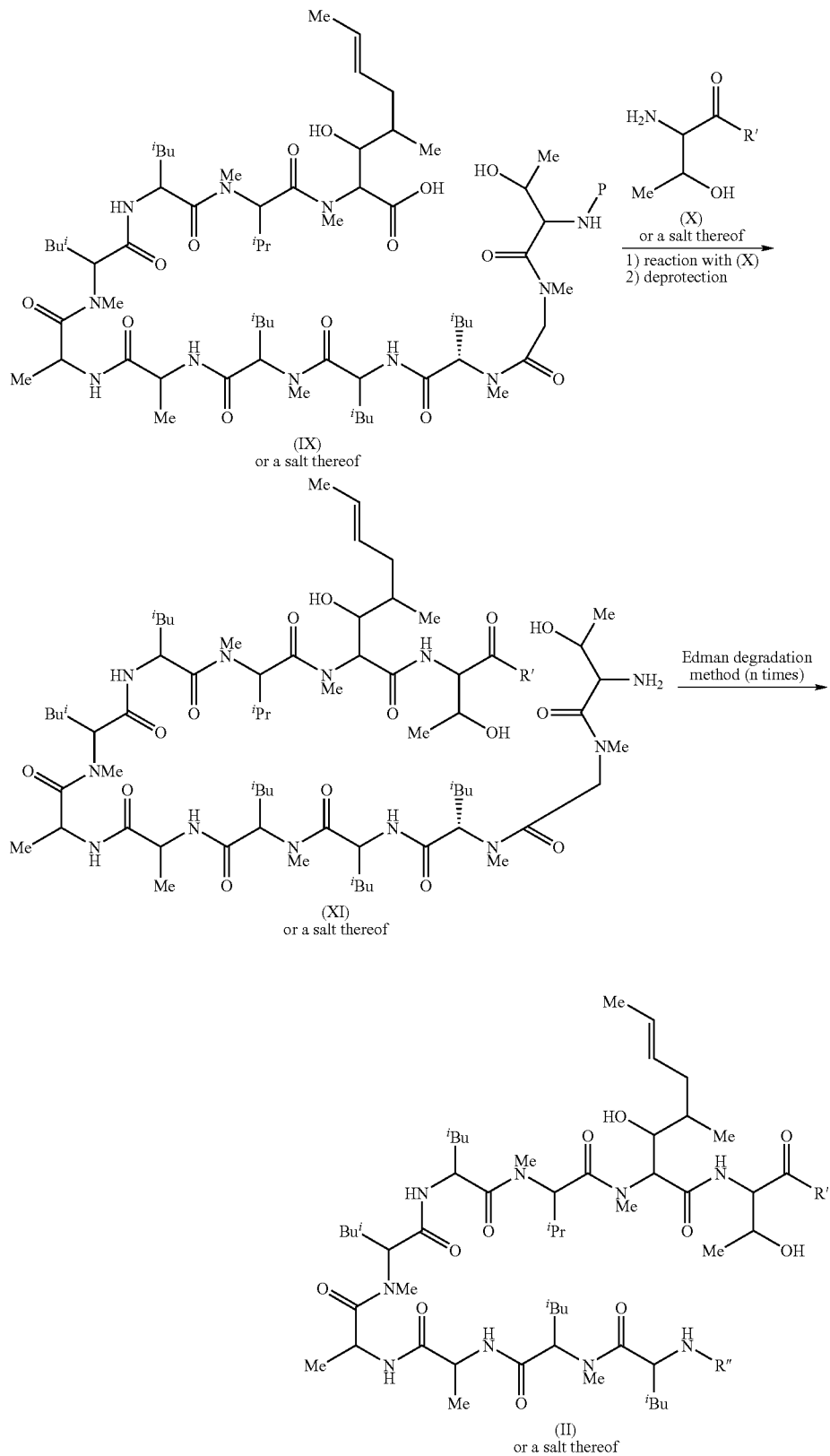

wherein

X and Y are as defined above,

L is a leaving group,

P is amino protective group,

R' is methoxy or

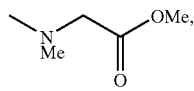

R" is H or

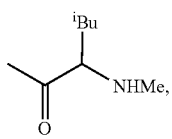

and n in the "n times" is 2 or 3.

The processes for the preparation of the object compounds and the starting compounds are described below.

Process 1

The object compound (Ia) or a salt thereof can be prepared from the compound (IIa) or a salt thereof by the following processes.

a) Introduction of Protected Amino Acid

This reaction is the amidation of the compound (IIa) with the compound (V).

Usually, the compound (V) is carboxylic acid (L is OH) or the reactive derivative thereof (including an acyl halide (e.g., carbonyl chloride, carbonyl bromide, and the like), an acid anhydride, an activated ester (e.g., vinyl ester, propargyl ester, 2,4-dinitrophenyl ester, pentafluorophenyl ester, methanesulfonylphenyl ester, dimethyliminomethyl ester, p-nitrophenyl thioester, an activated ester with a N-hydroxy compound (such as N-hydroxysuccinimide, N-hydroxybenzotriazole, and the like), and the like), or the like).

When the compound (V) is a free carboxylic acid compound, the reaction is preferably carried out in the presence of condensing agent (including carbodiimide (e.g., N,N-diisopropylcarbodiimide, N,N'-dicyclohexylcarbodiimide, 1-[3-(dimethylamino)propyl]-3-ethylcarbodiimide, and the like), diphenylphosphinic azido, diphenylphosphonic chloride, or the like).

And this reaction in the present reaction is usually carried out in the presence of an additive such as N-hydroxybenzotriazole (HOBt), 1-hydroxy-7-azabenzotriazole (HOAt), bis(2-oxo-3-oxazolydinyl)phosphinic chloride, and the like.

The reaction may be also be carried out in the presence of an organic or inorganic base such as an alkali metal bicarbonate, tri(lower)alkylamine, pyridine, N-(lower) alkylmorphorine, N,N-di(lower)alkylbenzylamine, or the like.

The reaction is usually carried out in a conventional solvent such as water, acetone, alcohol (e.g., methanol, ethanol, isopropyl alcohol, or the like), tetrahydrofuran, dioxane, toluene, methylene chloride, chloroform, N,N-dimethylformamide, or any other organic solvents which do not adversely affect the reaction or the mixture thereof.

The reaction temperature is not limited and the reaction is usually carried out under cooling to heating.

b) Deprotection

This reaction is elimination reaction of amino protective group of the compound (IIIa) or a salt thereof. And this reaction is also the reaction of methyl ester moiety of the compound (IIIa) or the salt thereof to carboxylic acid.

These two reactions are carried out at once (for example, referred to Preparation 68 or 161 described later) or in two divisional reactions (for example, referred to Preparations 7 and 171 or 153 and 169 described later) according to the reaction substrate or the reaction condition.

c) cyclization

This cyclization is carried out by the amidation of the compound (IVa), so this reaction can be carried out in the same manner as in the aforementioned Process 1-a), and therefore the reagents to be used and the reaction conditions (e.g., solvent, reaction temperature, etc.) can be referred to those of Process 1-a).

Process 2

The object compound (Ib) or a salt thereof can be prepared from the compound (IIb) by a series of reaction that contains introduction of protected amino acid, deprotection and cyclization as illustrated aforementioned. And each reaction can be carried out in the same manner as in the aforementioned Process 1, and therefore the reagents to be used and the reaction conditions (e.g., solvent, reaction temperature, etc.) can be referred to those of Process 1.

Process 3

The object compound (Ic) or a salt thereof can be prepared from the compound (IIc) by a series of reaction that contains introductions of protected amino acid and deprotection reactions each twice, and cyclization as illustrated aforementioned. And each reaction can be carried out in the same manner as in the aforementioned Process 1, and therefore the reagents to be used and the reaction conditions (e.g., solvent, reaction temperature, etc.) can be referred to those of Process 1.

Process 4

The object compound (Id) or a salt thereof can be prepared by subjecting the compound (Ic) to catalytic hydrogenation.

Suitable catalysts to be used in the catalytic hydrogenation are conventional ones such as platinum catalysts (e.g., platinum plate, spongy platinum, platinum black, colloidal platinum, platinum oxide, platinum wire, etc.), palladium catalysts (e.g., spongy palladium, palladium black, palladium oxide, palladium on carbon, palladium hydroxide on carbon, colloidal palladium, palladium on barium sulfate, palladium on barium carbonate, etc.), and the like.

The hydrogenation is usually carried out in a conventional solvent such as water, alcohol (e.g., methanol, ethanol, isopropyl alcohol, etc.), tetrahydrofuran, dioxane, toluene, methylene chloride, ethylene dichloride, chloroform, N,N-dimethylformamide, N,N-dimethylacetamide or any other organic solvents which do not adversely affect the reaction, or a mixture thereof.

The reaction temperature is not critical, and the reaction is usually carried out under cooling to warming.

Process A

The compound (IX) or a salt thereof can be prepared from the compound (VII) or a salt thereof by the following processes.

a) Rearrangement

This reaction is the rearrangement of the compound (VII).

The reaction is usually carried out in the presence of acid (such as trifluoroacetic acid, sulfuric acid, methanesulfonic acid, or the like).

The reaction is usually carried out in a conventional solvent such as water, acetone, alcohol (e.g., methanol, ethanol, isopropyl alcohol, or the like), tetrahydrofuran, dioxane, toluene, methylene chloride, chloroform, N,N-dimethylformamide, or any other organic solvents which do not adversely affect the reaction or the mixture thereof.

The reaction temperature is not limited and the reaction is usually carried out under cooling to heating.

This reaction of the present invention, because of and owing to the substrate, can be carried out under the mild condition such as mild acid (p-toluenesulfonic acid) and mild temperature (ambient temperature to warming) to give a compound selectively subjected the rearrangement reaction.

b) Amino Protection

This reaction is protection of amino moiety, which goes out by the rearrangement reaction.

The reaction is usually carried out in a conventional solvent such as water, alcohol (e.g., methanol, ethanol, isopropyl alcohol, or the like), tetrahydrofuran, dioxane, toluene, methylene chloride, chloroform, N,N-dimethylformamide, or any other organic solvents which do not adversely affect the reaction or the mixture thereof.

The reaction temperature is not limited and the reaction is usually carried out under cooling to heating.

These series of reactions (a) rearrangement and b) amino protection) can be carried out by the method disclosed in Preparation 156 mentioned later or the similar manners thereto.

c) Hydrolysis

The compound (IX) or a salt thereof can be prepared, from the compound (VIII) or a salt thereof by hydrolysis.

The hydrolysis is preferably carried out in the presence of a base (including an inorganic base and organic base such as alkali metal (e.g., sodium, potassium, etc.), alkaline earth metal (e.g., magnesium, calcium, etc.), the hydroxide or carbonate or bicarbonate of alkali metal or alkaline earth metal, trialkylamine (e.g., trimethylamine, etc.), hydrazine, picoline, 1,5-diazabicyclo [4.3.0]non-5-ene, 1,8-diazabicyclo[5.4.0]undec-7-ene, or the like) or an acid (including an organic acid (e.g., formic acid, acetic acid, propanoic acid, trifluoroacetic acid, etc.), an inorganic acid (e.g., hydrobromic acid, sulfuric acid, hydrochloric acid, etc.) and Lewis acid (e.g., boron tribromide, aluminum chloride, titanium trichloride, etc.)).

The reaction is usually carried out in a conventional solvent such as water, alcohol (e.g., methanol, ethanol, isopropyl alcohol, etc.), tetrahydrofuran, dioxane, toluene, methylene chloride, chloroform, N,N-dimethylformamide, or any other organic solvent which does not adversely affect the reaction or the mixture thereof.

A liquid base or acid can be also used as the solvent.

The reaction temperature is not limited and the reaction is usually carried out under cooling to heating.

This reaction can be carried oUt by the method disclosed in Preparation 167 mentioned later or the similar manners thereto.

Process B

The compound (II) or a salt thereof can be prepared from the compound (IX) or a salt thereof by the following processes.

a) Reaction with (X)

This reaction is the amidation of the compound (IX) with the compound (X), so this reaction can be carried out in the same manner as in the aforementioned Process 1-a), and therefore the reagents to be used and the reaction conditions (e.g., solvent, reaction temperature, etc.) can be referred to those of Process 1-a).

This reaction can be carried out by the method disclosed in Preparation 90 mentioned later or the similar manners thereto.

b) Deprotection

This reaction can be carried out in the same manner as in the aforementioned Process 1-b), and therefore the reagents to be used and the reaction conditions (e.g., solvent, reaction temperature, etc.) can be referred to those of Process 1-b).

This reaction can be carried out by the method disclosed in Preparation 152 mentioned later or the similar manners thereto.

c) Edman Degradation Method (n Times)

The reaction is usually carried out in a conventional solvent such as water, acetonitrile, acetone, alcohol (e.g., methanol, ethanol, isopropyl alcohol, or the like), tetrahydrofuran, dioxane, toluene, methylene chloride, chloroform, ethyl acetate, N,N-dimethylformamide, or any other organic solvent which does not adversely affect the reaction or the mixture thereof.

The reaction temperature is not limited and the reaction is usually carried out under cooling to heating.

And the reaction is carried out repeatedly until the object compound can be obtained.

This reaction can be carried out by the method disclosed in Preparations 138, a series of 2 and 3, etc. mentioned later or the similar manners thereto (e.g., M. K. Eberle et al., *J. Org. Chem.* 59, 7249-7258 (1994) described about this type Edman degradation method).

The compound (VII) or a salt thereof (FR901459 compound) can be produced by fermentation of fungus (*Stachybotrys chartarum* No. 19392: deposit number FERM BP-3364) according to the method described in Japanese Laid-open Patent Application Hei 5-271267, for example.

More specifically, the object compound can be prepared by the processes described in Examples in the present application or similar processes.

The compounds obtained by the above-mentioned processes 1 to 4, and A and B can be isolated and purified by a conventional method, such as pulverization, recrystallization, column chromatography, high performance liquid chromatography, reprecipitation and demineralized resin column chromatography.

Suitable salts of the object compound (I) are conventional pharmaceutically acceptable and non-toxic salts, and may be a salt with a base or an acid addition salt, for example, a salt with an inorganic base (such as an alkali metal salt, e.g. sodium salt, potassium salt, etc., an alkaline earth metal salt, e.g. calcium salt, magnesium salt, etc., an ammonium salt), a salt with an organic base (such as an organic amine salt, e.g. triethylamine salt, diisopropylethylamine salt, pyridine salt, picoline salt, ethanolamine salt, triethanolamine salt, dicyclohexylamine salt, N'N'-dibenzylethylenediamine salt, etc.), an inorganic acid addition salt (such as hydrochloride, hydrobromide, sulfate, phosphate, etc.), an organic carboxylic acid or sulfonic acid addition salt (such as formate, acetate, trifluoroacetate, maleate, tartrate, gluconate, fumarate, methanesulfonate, benzenesulfonate, toluenesulfonate, etc.), a salt with a basic or acidic amino acid (such as arginine, aspartic acid, glutamic acid, etc.) and the like.

In the above and subsequent descriptions of the present specification, suitable examples and illustrations of the various definitions to be included within the scope of the invention are explained in detail as follows.

The term "lower" is intended a group having 1 to 6, preferably 1 to 4, unless otherwise indicated.

Suitable examples of "lower alkyl" and "lower alkyl" moiety may include a straight or branched one having 1 to 6 carbon atom(s), such as methyl, ethyl, propyl, isopropyl, butyl, isobutyl, sec-butyl, tert-butyl, pentyl, tert-pentyl, neopentyl, hexyl, isohexyl, and the like.

Suitable examples of "lower alkoxy" and "lower alkoxy" moiety may include a straight or branched one having 1 to 6 carbon atom(s), such as methoxy, ethoxy, propoxy, isopropoxy, butoxy, isobutoxy, tert-butoxy, pentyloxy, tert-pentyloxy, neopentyloxy, hexyloxy, isohexyloxy, and the like.

Suitable examples of "cyclo(lower)alkyl" may include cyclic alkyl having 3 to 6 carbon atom, such as cyclopropyl, cyclobutyl, cyclopentyl and cyclohexyl, and the like.

Suitable examples of "aryl" and "aryl" moiety may include phenyl which may be substituted with lower alkyl (e.g., phenyl, mesityl, tolyl, etc.), naphthyl, anthryl, tetrahydronaphthyl, indenyl, tetrahydroindenyl, and the like.

Suitable examples of "optionally substituted amino" may include amino which is optionally substituted by one or two suitable substitutent(s) such as lower alkyl, amino protective group (e.g., benzyloxycarbonyl, t-butoxycarbonyl(Boc) and the like) and the like.

Suitable examples of "optionally substituted carbamoyloxy" may include carbamoyloxy which is optionally substituted by one or two suitable substitutent(s) such as lower alkyl, amino protective group (e.g., benzyloxycarbonyl, t-butoxycarbonyl(Boc) and the like) and the like.

Suitable examples of "heterocyclic group" may include:

unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), azepinyl, etc.;

saturated 3 to 8-membered (more preferably 5 or 6-membered) heteromonocyclic group containing 1 to 4 nitrogen atom(s), for example, aziridinyl, azetinyl, pyrrolidinyl, imidazolidinyl, piperidyl, piperazinyl, 2,5-methanopiperazinyl, hexahydroazepinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, tetrahydroquinolyl, tetrahydroisoquinolyl, tetrahydroindolyl, dihydroindazolyl, etc.;

unsaturated 3 to 8-membered (more preferably 5 or 6-membered) heteromonocyclic group containing 1 or 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 or 2 oxygen atom(s) and 1 to 3 nitrogen atom(s), for example, morpholinyl, sydnonyl, etc.;

unsaturated condensed heterocyclic group containing 1 or 2 oxygen atom(s), and 1 to 3 nitrogen atom(s), for example, benzoxazolyl, benzoxadiazolyl, etc.;

unsaturated 3 to 8-membered (more preferably 5 or 6-membered) heteromonocyclic group containing 1 or 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 or 2 sulfur atom(s) and 1 to 3 nitrogen atom(s), for example thiazolidinyl, etc.;

unsaturated 3 to 8-membered (more preferably 5 or 6-membered) heteromonocyclic group containing 1 or 2 sulfur atom(s), for example, thienyl, dihydrodithiinyl, dihydrodithionyl, etc.;

unsaturated condensed heterocyclic group containing 1 or 2 sulfur atom(s) and 1 to 3 nitrogen atom(s), for example, benzothiazolyl, benzothiadiazolyl, imidazothiadiazolyl, etc.;

unsaturated 3 to 8-membered (more preferably 5 or 6-membered) heteromonocyclic group containing an oxygen atom, for example, furyl etc.;

saturated 3 to 8-membered (more preferably 5 or 6-membered) heteromonocyclic group containing 1 or 2 oxygen atom(s), for example, oxiranyl, 1,3-dioxolanyl, tetrahydrofuranyl, tetrahydropyranyl, etc.;

unsaturated 3 to 8-membered (more preferably 5 or 6-membered) heteromonocyclic group containing an oxygen atom and 1 or 2 sulfur atom(s), for example, dihydrooxathiinyl, etc.;

unsaturated condensed heterocyclic group containing 1 or 2 sulfur atom(s), for example benzothienyl, benzodithiinyl, etc.; and unsaturated condensed heterocyclic group containing an oxygen atom and 1 or 2 sulfur atom(s), for example, benzoxathiinyl, etc.; saturated condensed heteromonocyclic group containing 1 to 3 nitrogen atom(s), for example, tetrahydropyridopyrrolidinyl, etc.;

and the like.

Suitable "N-containing heterocyclic group" can be referred to the ones as mentioned above, wherein the heterocyclic group is containing at least one nitrogen atom such as pyrrolidinyl, piperidyl, morpholinyl, thiazolyl, oxazolyl, and the like.

Suitable "optionally substituted heterocyclic group" may include the heterocyclic group as mentioned above, which is optionally substituted by a suitable substituent such as lower alkyl, lower alkoxy, aryl, amino, lower alkoxycarbonyl, and the like.

The term "halogen" means fluorine, chlorine, bromine and iodine.

V. Lohmann et al., *Science* 285, 110-113 (1999) reported that they prepared human hepatoma cell lines (Huh-7) in which subgenomic HCV RNA molecules were introduced, and found that subgenomic HCV RNA was replicated in the cells at a high rate. It is thought that the replication mechanism of the subgenomic HCV RNA in these cell lines is extremely similar to the replication of full length HCV RNA genome in hepatic cells infected with HCV. Hence, the method for evaluating the activity of the compound (I) for inhibiting RNA replication in accordance with the present invention is based on the cellular assay method that uses Huh-7 cells in which subgenomic HCV RNA is introduced.

In order to show the usefulness of the compound (I) or a salt thereof in the present invention, a pharmacological test example of representative compounds in the present application is shown as follows.

TEST EXAMPLE

1. HCV Replicon Reporter Assay

The inhibitory activity of the test compounds against the replication of HCV replicon was evaluated by quantified the activity of luciferase, a reporter gene product encoded in the replicon system reported by Yokota et al., *EMBO* 4: 602-608 (2003). The enzyme assay was carried out according to the technical manual of the Steady-Glo® luciferase assay system (Promega). The replicon assay was carried out with the modified method reported by Lohmann et al., *Science* 285: 110 (1999). The details are described in the following.

1) Addition of Agent to Cells $6 \times 10^3$ HCV replicon cells in D-MEM medium containing 5% fetal bovine serum were seeded in each well of a 96-well microtiter plate (Corning Inc.). After the cells were incubated at 37° C. for 16 hours in 5% $CO_2$, the test compound was added.

2) Luciferase Assay Procedure

After cultivation for two more days, the culture medium was removed and 25 μl of Glo Lysis buffer was added to each well and incubated for 5 minutes. Allowing lysis to occur, 25 μl of Steady-Glo® assay reagent was added to each well. After incubation for 5 minutes, the luminescence was measured with a luminometer, Mithras LB940 (BERTHOLD TECHNOLOGIES GmbH & Co. KG) following the manufacturer's instructions.

3) Test Result

The luciferase activities in replicon cells treated at each concentrations of the compound were employed for the calculation of EC50 value of the each compound, which gave the compound concentration indicating 50% enzyme activity level to the control (no drug group, containing only DMSO).

| Test compound | HCV replicon replication inhibitory activity: EC50 (μg/ml) |
| --- | --- |
| Object compound of Example 9 | <0.5 |
| Object compound of Example 12 | <0.5 |
| Object compound of Example 14 | <0.5 |
| Object compound of Example 15 | <0.5 |
| Object compound of Example 16 | <0.5 |
| Object compound of Example 25 | <0.5 |
| Object compound of Example 31 | <0.5 |
| Object compound of Example 32 | <0.5 |
| Object compound of Example 52 | <0.5 |

From the result of the above-mentioned test example, it is realized that the compound (I) or a salt thereof of the present invention possesses an anti-hepatitis C virus activity.

The anti-HCV agent in the present invention, containing the compound (I) or a salt thereof as an active ingredient, can be used in the form of a pharmaceutical preparation, for example, in a solid, semisolid or liquid form, in admixture with an organic or inorganic carrier or excipient suitable for oral; sublingual; buccal; nasal; respiratory; parenteral (intracutaneous, intraorgan, subcutaneous, intradermal, intramuscular, intra-articular, central-venous, hepatic-venous, peripheral-venous, lymphatic, cardiovascular, arterial, ocular including injection around eye or intravenous drip around eye); intravenous drip into eyeball, augen structure or augen layer; aural including auditory canal, papillary chamber, external and internal auditory canals, drum membrane, tympanum, internal-auditory including spiralis cochleae ganglion, labyrinth, etc.; intestinal; rectal; vaginal; ureteral; and vesical administration. With respect to intrauterine and perinatal adaptation diseases, parenteral administration is preferable since administration is carried out in maternal blood vessels, or in vacancies, such as maternal organs including uterus, uterine cervix and vagina; fetal embryo, fetus, neonate, and combination tissue; and amnion, umbilical cord, umbilical artery and vein; placenta, and the like. Use of these passages is changed depending on the condition of each patient.

The compound (I) or a salt thereof can be administered independently as a therapeutic agent or may be desired to be used as part of prescribed drugs. The "anti-HCV agent" in accordance with the present invention can be used in the form of a pharmaceutical preparation, for example, in a solid, semisolid or liquid form, in admixture with at least one or some suitable organic or inorganic carriers or excipients, or other pharmacological therapeutic agents. The active ingredient can be compounded with, for example, usual pharmacologically acceptable and non-toxic carriers in a solid form, such as granules, tablets, pellets, troches, capsules or suppositories; creams; ointments: aerosols; powders for insufflation; in a liquid form, such as solutions, emulsions or suspensions for injection; oral ingestion; eye drops; and any other forms suitable for use. And, if necessary, there may be included in the above preparations auxiliary substances, such as stabilizing, thickening, wetting, hardening and coloring agents; perfumes or buffers; or any other additives used commonly.

The compound (I) or a pharmaceutically acceptable salt thereof is/are included in the pharmaceutical composition in an amount sufficient to produce the desired anti-hepatitis C effect upon the process or condition of diseases.

The combination use of IFN and/or ribavirin with the compound (I) or a salt thereof is effective against hepatitis C.

For applying the composition to humans, it is preferable to apply it by intravenous, intramuscular, pulmonary, oral administration, eye drop administration or insufflation. While the dosage of therapeutically effective amount of the compound (I) varies from and also depends upon the age and condition of each individual patient to be treated, in the case of intravenous administration, a daily dose of 0.001-400 mg of the compound (I) per kg weight of human being in the case of intramuscular administration, a daily dose of 0.1-20 mg of the compound (I) per kg weight of human being, in case of oral administration, a daily dose of 0.5-50 mg of the compound (I) per kg weight of human being is generally given for treating or preventing hepatitis C. However, these doses may be required to exceed the limit thereof to obtain therapeutic results.

The amount of the lipopeptide compound (I) or its pharmaceutically acceptable salt contained in the composition for a single unit dosage of the present invention is 0.1 to 400 mg, more preferably 1 to 200 mg, still more preferably 5, to 100 mg, specifically 5, 10, 15, 20, 25, 30, 35, 40, 45, 50, 55, 60, 65, 70, 75, 80, 85, 90, 95 and 100 mg.

The present invention may include an article of manufacture, comprising packaging material and the compound (I) identified in the above contained within said packaging material, wherein said the compound (I) is therapeutically effective for preventing or treating hepatitis C, and wherein said packaging material comprises a label or a written material which indicates that said compound (I) can or should be used for preventing or treating hepatitis C.

The present invention may include a commercial package comprising the pharmaceutical composition-containing the compound (I) identified in the above and a written matter associated therewith, wherein the written matter states that the compound (I) can or should be used for preventing or treating hepatitis C.

It is to be noted that the compound (I) or a salt thereof may include one or more stereoisomer(s), such as optical isomer(s) and geometrical isomer(s), due to asymmetric carbon atom(s) and double bond(s), and that all such isomers and the mixture thereof are included within the scope of the present invention.

The compound (I) or a salt thereof may include solvated compound (e.g. hydrate, ethanolate, etc.).

The compound (I) or a salt thereof may include both the crystal form and non-crystal form.

The compound (I) or a salt thereof may include the prodrug form.

The patent specifications and publications cited herein are incorporated in this specification by reference.

The following Preparations and Examples are given for the purpose of illustrating the present invention. However, the present invention is not limited to these Preparations and Examples.

The Starting Compounds used and the Object Compounds obtained in the following Examples 1 to 83 are given as mentioned below.

The abbreviations, symbols and terms used in the Preparations, Examples, and Formulae in the above and subsequent descriptions of the present specification (including the tables) have the following meanings.

AcOEt Ethyl acetate
Bop-Cl Bis(2-oxo-3-oxazolidinyl)phosphinic chloride
$CHCl_3$ Chloroform
$CH_2Cl_2$ Dichloromethane
$Et_2O$ Diethyl ether
HCl Hydrochloric acid
HOAt 1-Hydroxy-7-azabenzotriazole
LiOH Lithium hydroxide
MeCN Acetonitrile
MeOH Methanol
$MgSO_4$ Magnesium sulfate
$NaHCO_3$ Sodium hydrogencarbonate
NaOH Sodium hydroxide
$Na_2SO_4$ Sodium sulfate
TFA Trifluoroacetic acid
WSCD 1-[3-(Dimethylamino)propyl]-3-ethylcarbodiimide
$^nBu$ n-Butyl
$^iBu$ Isobutyl
$^tBu$ tert-Butyl
Cy.Hex. Cyclohexyl
Et Ethyl
Me Methyl
Ph phenyl
$^iPr$ Isopropyl
Bn Benzyl
Boc tert-Butoxycarbonyl
Fmoc 9H-Fluoren-9-ylmethoxycarbonyl
Ex. Example number
Prep. Preparation number
MS Mass spectrometry data Prep. 1

To a solution of the object compound of Prep. 158 below (crude 78 g, theoretical 76.9 g) in MeCN (555 ml) was added 1N HCl (555 ml) under ice bath cooling. The mixture was warmed to 30° C., and stirred at 30° C. for 3 hrs. The resulting mixture was neutralized with $Na_2CO_3$ solution (29.48 g in $H_2O$ 300 ml), and concentrated in vacuo. The pH value of residual solution was adjusted to 8 with saturated $NaHCO_3$ aqueous solution, and the solution was extracted with AcOEt. The organic phase was washed with saturated $NaHCO_3$ aqueous solution and brine, and dried over $Na_2SO_4$. Solvent was removed in vacuo to give methyl (3S,6S,9S,12S,15R,18S,21S,24S,27S,30S)-30-[(1R)-1-hydroxyethyl]-27-[(1R,2R,4E)-1-hydroxy-2-methyl-4-hexen-1-yl]-3,6,9,18,21-pentaisobutyl-24-isopropyl-8,12,15,17,23,26-hexamethyl-4,7,10,13,16,19,22,25,28-nonaoxo-2,5,8,11,14,17,20,23,26,29-decaazahentriacontan-31-oate (crude 70 g, theoretical 65.5 g) as pale brown powder. Obtained crude product was used in next reaction without further purification.

Prep. 2

To a solution of the object compound of Prep. 1 (crude 70 g, theoretical 65.5 g) in AcOEt (660 ml) was added isothiocyanatobenzene (10 ml) at ambient temperature, and the pH value of the mixture was added to 7.5 with diisopropylethylamine. The reaction mixture was stirred at ambient temperature for 1.5 hrs. To the resulting solution was added N,N-dimethylpropanediamine (9.1 g) and stirred for 5 minutes. The reaction mixture was poured into 0.5N HCl (1 l) and extracted with AcOEt. The organic phase was washed with 0.5N HCl, saturated $NaHCO_3$ aqueous solution, and brine, and dried over $Na_2SO_4$. Solvent was removed in vacuo and the residue was purified with Silica-gel column chromatography eluting with Hexane:AcOEt (2:1-1:1-1:2) to give-methyl (3S,6S,9S,12S,15R,18S,21S,24S,27S,30S)-1-anilino-30-[(1R)-1-hydroxyethyl]-27-[(1R,2R,4E)-1-hydroxy-2-methyl-4-hexen-1-yl]-3,6,9,18,21-pentaisobutyl-24-isopropyl-2,8,12,15,17,23,26-heptamethyl-4,7,10,13,16,19,22,25,28-nonaoxo-1-thioxo-2,5,8,11,14,17,20,23,26,29-decaazahentriacontan-31-oate (44.3 g) as pale yellow powder.

Prep. 3

To a solution of the object compound of Prep. 2 (44.3 g) in MeCN (337 ml) was added 1N HCl (337 ml) and the mixture was stirred at 30° C. for 2 hrs. The resulting mixture was neutralized with $Na_2CO_3$ solution (58.8 g in $H_2O$ 300 ml), and concentrated in vacuo. The pH value of residual solution was adjusted 8 with saturated $NaHCO_3$ aqueous solution, and the solution was extracted with AcOEt. The organic phase was washed with saturated $NaHCO_3$ and brine, and dried over $Na_2SO_4$. Solvent was removed in vacuo and the residue was purified with Silica-gel column chromatography eluting $CHCl_3$:MeOH (100:0-97:3) to give methyl (2S,5S,8S,11S,14S,17R,20S,23S,26S)-26-amino-2-[(1R)-1-hydroxyethyl-]-5-[(1R,2R,4E)-1-hydroxy-2-methyl-4-hexen-1-yl]-11,14,23-triisobutyl-8-isopropyl-6,9,15,17,20,24,28-heptamethyl-4,7,10,13,16,19,22,25-octaoxo-3,6,9,12,15,18,21,24-octaazanonacosan-1-oate (29.1 g) as pale yellow form.

$^1H$-NMR (chloroform-d, δ ppm): 10.27 (0.5H, d, J=9.0 Hz), 7.38 (0.5H, d, J=8.5 Hz), 7.00 (0.5H, d, J=8.5 Hz), 6.93 (0.5H, d, J=8.5 Hz), 6.89 (1H, d, J=8.5 Hz), 6.84 (0.5H, d, J=8.0 Hz), 6.80 (0.5H, d, J=8.0 Hz), 5.14-5.51 (5H, m), 4.86-5.04 (1H, m), 4.66-4.81 (2H, m), 4.55 (2H, m), 4.31 (1H, m), 4.00 (1H, m), 3.77 (1H, m), 3.76 (1.5H, s), 3.75 (1.5H, s), 3.25 (1.5H, s), 3.14 (1.5H, s), 3.06 (1.5H, s), 3.02 (1.5H, s), 3.01 (1.5H, s), 3.00 (3H, s), 2.71 (1.5H, s), 2.35 (2H, m), 2.03-1.24 (61H, m)

Prep. 4

To a solution of the object compound of Prep. 59 below (3.2 g) in CH$_2$Cl$_2$ (38.5 ml) was added TFA (9.6 ml) under ice bath cooling, and the mixture was stirred for 2 hrs under ice bath cooling. To the mixture was added TFA (7 ml) and the mixture was additionally stirred for 1 hour under ice bath cooling. Resulting mixture was neutralized with Na$_2$CO$_3$ aqueous solution (6.6 g in 100 ml H$_2$O) under ice bath cooling, and concentrated in vacuo. To the residual solution was added saturated NaHCO$_3$ aqueous solution to adjust pH=8, and the mixture was extracted with AcOEt. The organic phase was washed with saturated NaHCO$_3$ aqueous solution and brine, and dried over NaSO$_4$. Solvent was removed in vacuo to give methyl (3S,6S,9S,12S,15R,18S,21S,24S,27S,30S)-3-sec-butyl-30-[(1R)-1-hydroxyethyl]-27-[(1R,2R,4E)-1-hydroxy-2-methyl-4-hexen-1-yl]-6,9,18,21-tetraisobutyl-24-isopropyl-8,12,15,17,23,26-hexamethyl-4,7,10,13,16,19,22,25,28-nonaoxo-2,5,8,11,14,17,20,23,26,29-decaazahentriacontan-31-oate (3.0 g) as colorless solid.

The compounds of Prep. 5-19 were obtained in a similar manner to that of Prep. 4.

Prep. 20

To a solution of the object compound of Prep. 208 below (1.20 g) in dioxane (10 ml) was added 1N LiOH (3.1 ml) under ice-bath cooling. After being stirred for 3 hrs at the same temperature, the solution was acidified with 5% citric acid to be pH 5, concentrated in vacuo to remove dioxane, and extracted with AcOEt (50 ml). The organic layer was washed with brine, dried over MgSO$_4$, and concentrated in vacuo. The resulting residue was triturated with Et$_2$O to give (3R, 16S,9S,12S,15S,18R,21S,24S,27S,30S,33S)-6-(1-tert-butoxyethyl)-33-[(1R)-1-hydroxyethyl]-30-[(1R,2R,4E)-1-hydroxy-2-methyl-4-hexen-1-yl]-9,12,21,24-tetraisobutyl-27-isopropyl-3,5,11,15,18,20,26,29-octamethyl-4,7,10,13,16,19,22,25,28,31-decaoxo-2,5,8,11,14,17,20,23,26,29,32-undecaazatetratriacontan-34-oic acid (790 mg) as a solid.

The compounds of Prep. 21-24 were obtained in a similar manner to that of Prep. 20.

Prep. 25

To a solution of the object compound of Prep. 4 (81 mg) was added (2R)-2-{[(9H-fluoren-9-ylmethoxy)carbonyl](methyl)amino}propanoic acid (33.5 mg), Bop-Cl (26.2 mg), and diisopropylethylamine (36 µl) under ice bath cooling. The mixture was stirred for 13 hrs at ambient temperature, and extracted with AcOEt. The organic phase was washed with 10% citric acid aqueous solution, saturated NaHCO$_3$ aqueous solution, and brine, and dried over Na$_2$SO$_4$. Solvent was removed in vacuo, and the residue was purified by preparative thin layer chromatography (CHCl$_3$:MeOH=90:10) to give methyl-(5R,8S,11S,14S,17S,20R,23S,26S,29S,32S,35S)-8-sec-butyl-1-(9H-fluoren-9-yl)-35-[(1R)-1-hydroxyethyl]-32-[(1R,2R,4E)-1-30-hydroxy-2-methyl-4-hexen-1-yl]-11,14,23,26-tetraisobutyl-29-isopropyl-4,5,7,13,17,20,22,28,31-nonamethyl-3,6,9,12,15,18,21,24,27,30,33-undecaoxo-2-oxa-4,7,10,13,16,19,22,25,28,31,34-undecaazahexatriacontan-36-oate (74 mg) as colorless solid.

The compounds of Prep. 26-40 were obtained in a similar manner to that of Prep. 25.

Prep. 41

To a solution of the object compound of Prep. 25 (73 mg) in dioxane (1.9 ml) was added 1N NaOH (0.49 ml) at ambient temperature and the mixture was stirred for 2 hrs. To the reaction mixture was added 10% citric acid aqueous solution to adjust pH=4, and the solution was extracted with AcOEt. The organic phase was washed with brine, and was dried over Na$_2$SO$_4$. Solvent was removed in vacuo and the residue was triturated with Et$_2$O to give (3R,6S,9S,12S,15S,18R,21S,24S,27S,30S,33S)-6-sec-butyl-33-[(1R)-1-hydroxyethyl]-30-[(1R,2R,4E)-1-hydroxy-2-methyl-4-hexen-1-yl]-9,12,21,24-tetraisobutyl-27-isopropyl-3,5,11,15,18,20,26,29-octamethyl-4,7,10,13,16,19,22,25,28,31-decaoxo-2,5,8,11,14,17,20,23,26,29,32-undecaazatetratriacontan-34-oic acid (56 mg) as colorless powder.

The compounds of Prep. 42-56 were obtained in a similar manner to that of Prep. 41.

Prep. 57

To a solution of the object compound of Prep. 93 below (1.60 g) in N,N-dimethylformamide (16 ml) was added piperidine (1.1 ml) at room temperature. After being stirred at the same temperature for 2 hrs, the reaction mixture was concentrated in vacuo. The residue was dissolved in AcOEt (60 ml) and the solution was washed with 5% citric acid aqueous solution, saturated NaHCO$_3$, and brine, dried over MgSO$_4$, and concentrated in vacuo. The crude product was purified by Silica-gel column (eluent 2% MeOH in CHCl$_3$) to give methyl (2S,5S,8S,11S,14S,17R,20S,23S,26S,29S)-2-[(1R)-1-hydroxyethyl]-5-[(1R,2R,4E)-1-hydroxy-2-methyl-4-hexen-1-yl]-11,14,23,26-tetraisobutyl-8-isopropyl-6,9,15,17,20,24,30,32,32-nonamethyl-29-(methylamino)-4,7,10,13,16,19,22,25,28-nonaoxo-31-oxa-3,6,9,12,15,18,21,24,27-nonaazatritriacontan-1-oate (1.34 g) as a powder.

The compound of Prep. 58 was obtained in a similar manner to that of Prep. 57.

Prep. 59

To a solution of the object compound of Prep. 3 (3.0 g) in CH$_2$Cl$_2$ (60 ml) was added (2S,3S)-2-[(tert-butoxycarbonyl)(methyl)amino]-3-methylpentanoic acid (839 mg) and HOAt (466 mg), and WSCD (531 mg) under ice bath cooling, and the mixture was stirred for 1.5 hrs under ice bath cooling. The resulting mixture was concentrated in vacuo and the residue was extracted with AcOEt. The organic phase was washed with saturated NaHCO$_3$ aqueous solution, and brine, and dried over Na$_2$SO$_4$. Solvent was removed in vacuo to give methyl (6S,9S,12S,15S,18R,21S,24S,27S,30S,33S)-6-sec-butyl-33-[(1R)-1-hydroxyethyl]-30-[(1R,2R,4E)-1-hydroxy-2-methyl-4-hexen-1-yl]-9,12,21,24-tetraisobutyl-27-isopropyl-2,2,5,11,15,18,20,26,29-nonamethyl-4,7,10,13,16,19,22,25,28,31-decaoxo-3-oxa-5,8,11,14,17,20,23,26,29,32-decaazatetratriacontan-34-oate (3.22 g) as pale yellow powder. Obtained product was used in next reaction without further purification.

The compounds of Prep. 60-67 were obtained in a similar manner to that of Prep. 59.

Prep. 68

Methyl-(6R,9S,12S,15S,18R,21S,24S,27S,30S,33S)-6-sec-butyl-33-[(1R)-1-hydroxyethyl]-30-[(1R,2R,4E)-1-hydroxy-2-methyl-4-hexen-1-yl]-9,12,21,24-tetraisobutyl-27-isopropyl-2,2,11,15,18,20,26,29,35-nonamethyl-4,7,10,13,16,19,22,25,28,31,34-undecaoxo-3-oxa-5,8,11,14,17,20,23,26,29,32,35-undecaazaheptatriacontan-37-oate (80 mg) was dissolved in 20% TFA/CH$_2$Cl$_2$ (2 ml) under ice-bath cooling. After being stirred at the same temperature for 4 hrs, to the solution was added saturated NaHCO$_3$ aqueous solution to be pH 8. The mixture was extracted with CHCl$_3$ (20 ml) and the organic layer was washed with saturated NaHCO$_3$ and brine, dried over MgSO$_4$, and concentrated in vacuo. The resulting residue was dissolved in MeOH (4 ml). To the solution was added 1N LiOH (0.60 ml) under ice-bath cooling. After being stirred for 1 hr at the same temperature, the solution was acidified with 5% citric acid aqueous solution to be pH5, concentrated in vacuo to remove MeOH, and extracted with CHCl$_3$ (20 ml). The organic layer was washed with brine, dried over MgSO$_4$, and concentrated in vacuo. The resulting residue was triturated with Et$_2$O to give (5S,8S,11S,14S,17S,20R,23S,26S,29S,32R)-32-amino-5-[(1R)-1-hydroxyethyl]-8-[(1R,2R,4E)-1-hydroxy-2-methyl-4-hexen-1-yl]-14,17,26,29-tetraisobutyl-11-isopropyl-3,9,12,18,20,23,27,33-octamethyl-4,7,10,13,16,19,22,25,28,31-decaoxo-3,6,9,12,15,18,21,24,27,30-decaazapentatriacontan-1-oic acid (45 mg) as a solid.

The compounds of Prep. 69-74 were obtained in a similar manner to that of Prep. 68.

Prep. 75

To a solution of the object compound of Prep. 193 below (53 mg) in dioxane (0.64 ml) was added 1N NaOH (0.16 ml) at ambient temperature and the mixture was stirred for 2 hrs. To the reaction mixture was added 10% citric acid aqueous solution to adjust pH=4, and the solution was extracted with AcOEt. The organic phase was washed with brine, and was dried over Na$_2$SO$_4$. Solvent was removed in vacuo and the residue was triturated with Et$_2$O to give (3R,6S,9S,12S,15S,18R,21S,24S,27S,30S,33S)-33-[(1R)-1-hydroxyethyl]-30-[(1R,2R,4E)-1-hydroxy-2-methyl-4-hexen-1-yl]-3,6,9,12,21,24-hexaisobutyl-27-isopropyl-5,11,15,18,20,26,29-heptamethyl-4,7,10,13,16,19,22,25,28,31-decaoxo-2,5,8,11,14,17,20,23,26,29,32-undecaazatetratriacontan-34-oic acid (18 mg) as colorless powder.

The compounds of Prep. 76-89 were obtained in a similar manner to that of Prep. 75.

Prep. 90

To a solution of the object compound of Prep. 167 below (5.40 g), methyl {[(2S,3R)-2-amino-3-hydroxybutanoyl](methyl)amino}acetate hydrochloride (1.46 g) and HOAt (0.550 g) in CH$_2$Cl$_2$ (8.0 ml) was added a solution of WSCD (0.627 g) in CH$_2$Cl$_2$ (4 ml) under ice-bath cooling. After being stirred at the same temperature for 3 hrs, the reaction mixture was concentrated in vacuo. The residue was dissolved in AcOEt (200 ml) and the solution was washed with 0.5N HCl, 1M NaHCO$_3$, and brine, dried over anhydrous MgSO$_4$, and concentrated in vacuo to give methyl (6S,12S,15S,18S,21S,24R,27S,30S,33S,36S,39S)-6,39-bis[(1R)-1-hydroxyethyl]-36-[(1R,2R,4E)-1-hydroxy-2-methyl-4-hexen-1-yl]-12,15,18,27,30-pentaisobutyl-33-isopropyl-2,2,8,11,17,21,24,26,32,35,41-undecamethyl-4,7,10,13,16,19,22,25,28,31,34,37,40-tridecaoxo-3-oxa-5,8,11,14,11,20,23,26,29,32,35,38,41-tridecaazatritetracontan-43-oate (6.00 g) as a powder.

Prep. 91

To a solution of the object compound of Prep. 3 (120 mg), (2S)-2-[{(2R)-2-[(tert-butoxycarbonyl)(methyl)amino]propanoyl}(ethyl)amino]-3-methylpentanoic acid (59 mg), and HOAt (19 mg) in CH$_2$Cl$_2$ (6 ml) was added a solution of WSCD (0.21 mg) in CH$_2$Cl$_2$ (1 ml) under ice-bath cooling. After being stirred at the same temperature for 1 hr and at room temperature for 5 hrs, the reaction solution was concentrated in vacuo. The residue was dissolved in AcOEt (20 ml) and the solution was washed with 0.5N HCl, 1M NaHCO$_3$, and brine, dried over MgSO$_4$, and concentrated in vacuo to give methyl (6R,9S,12S,15S,18S,21R,24S,27S,30S,33S,36S)-9-sec-butyl-8-ethyl-36-[(1R)-1-hydroxyethyl]-33-[(1R,2R,4E)-1-hydroxy-2-methyl-4-hexen-1-yl]-12,15,24,27-tetraisobutyl-30-isopropyl-2,2,5,6,14,18,21,23,29,32-decamethyl-4,7,10,13,16,19,22,25,28,31,34-undecaoxo-3-oxa-5,8,11,14,17,20,23,26,29,32,35-undecaazaheptatriacontan-37-oate (155 mg) as an amorphous powder.

The compound of Prep. 92 was obtained in a similar manner to that of Prep. 91.

Prep. 93

To a solution of the object compound of Prep. 3 (1.20 g), (2S,3R)-3-tert-butoxy-2-{[(9H-fluoren-9-ylmethoxy)carbonyl](methyl)amino}butanoic acid (516 mg), and HOAt (171 mg) in CH$_2$Cl$_2$ (20 ml) was added a solution of WSCD (195 mg) in CH$_2$Cl$_2$ (1 ml) under ice-bath cooling. After being stirred at the same temperature for 1 hr and at room temperature for 4 hrs, the reaction solution was concentrated in vacuo. The residue was dissolved in AcOEt (50 ml) and the solution was washed with 0.5N HCl, 1M NaHCO$_3$, and brine, dried over MgSO$_4$, and concentrated in vacuo. to give methyl (5S,8S,11S,14S,17R,20S,23S,26S,29S,32S)-5-(1-tert-butoxyethyl)-1-(9H-fluoren-9-yl)-32-[(1R)-1-hydroxyethyl]-29-[(1R,2R,4E)-1-hydroxy-2-methyl-4-hexen-1-yl]-8,11,20,23-tetraisobutyl-26-isopropyl-4,10,14,17,19,25,28-heptamethyl-3,6,9,12,15,18,21,24,27,30-decaoxo-2-oxa-4,7,10,13,16,19,22,25,28,31-decaazatritriacontan-33-oate (1.6 g) as an amorphous powder.

The compound of Prep. 94 was obtained in a similar manner to that of Prep. 93.

Prep. 95

To a solution of the object compound of Prep. 166 below (1.20 g), (2S,3R)-3-tert-butoxy-2-{[(9H-fluoren-9-ylmethoxy)carbonyl](methyl)amino}butanoic acid (527 mg), and HOAt (174 mg) in CH$_2$Cl$_2$ (20 ml) was added a solution of WSCD (199 mg) in CH$_2$Cl$_2$ (1 ml) under ice-bath cooling. After being stirred at the same temperature for 1 hr and at room temperature for 4 hrs, the reaction solution was concentrated in vacuo. The residue was dissolved in AcOEt (50 ml) and the solution was washed with 0.5N HCl, 1M NaHCO$_3$, and brine, dried over MgSO$_4$, and concentrated in vacuo. The resulting residue was purified by Silica-gel column (eluent: 2% MeOH in CHCl$_3$) to give methyl (5S,8S,11S,14S,17R, 20S,23S,26S,29S,32S)-5-(1-tert-butoxyethyl)-1-(9H-fluoren-9-yl)-32-[(1R)-1-hydroxyethyl]-29-[(1R,2R,4E)-1-hydroxy-2-methyl-4-hexen-1-yl]-8,11,20,23-tetraisobutyl-26-isopropyl-4,10,14,17,19,25,28,34-octamethyl-3,6,9,12,15,18,21,24,27,30,33-undecaoxo-2-oxa-4,7,10,13,16,19,22,25,28,31,34-undecaazahexatriacontan-36-oate (1.58 g) as an amorphous powder.

The compounds of Prep. 96-109 and 111-116 were obtained in a similar manner to that of Prep. 95.

Prep 110

To a solution of the object compound of Ex. 25 below (190 mg) in pyridine (1.2 ml) were added acetic anhydride (280 μl). After the mixture was stirred overnight, the mixture was diluted with AcOEt, washed with 1N aqueous hydrochloric acid and aqueous NaHCO$_3$, dried over MgSO$_4$ and concentrated. The residue was chromatographed on silica gel (hexane/AcOEt=1/4 and then CH$_2$Cl$_2$/MeOH=9/1) to give (1R)-1-{(2S,5R,8S,11S,14S,17S,20R,23S,26S,29S,32S)-8-(1-tert-butoxyethyl)-32-[(1R,2R,4E)-1-hydroxy-2-methylhex-4-en-1-yl]-11,14,23,26-tetraisobutyl-29-isopropyl-4,5,7,13,17,20,22,28,31-nonamethyl-3,6,9,12,15,18,21,24,27,30,33-undecaoxo-1,4,7,10,13,16,19,22,25,28,31-undecaazacyclotritriacontan-2-yl}ethyl acetate (193 mg).

Prep. 117

To a solution of the object compound of Prep. 154 below (crude 84 g, theoretical 82.5 g) in MeCN (1 l) was added 1N HCl (1.11 l) under ice bath cooling. The mixture was warmed to 30° C., and stirred at 30° C. for 4 hrs. The resulting mixture was neutralized with Na$_2$CO$_3$ solution (58.8 g in H$_2$O 300 ml), and concentrated in vacuo. The pH value of residual solution was adjusted 8 with saturated NaHCO$_3$ aqueous solution, and the solution was extracted with AcOEt. The organic phase was washed with saturated NaHCO$_3$ aqueous solution and brine, and dried over Na$_2$SO$_4$. Solvent was removed in vacuo to give methyl (6S,9S,12S,15S,18R,21S,24S,27S,30S,33S)-33-[(1R)-1-hydroxyethyl]-30-[(1R,2R,4E)-1-hydroxy-2-methyl-4-hexen-1-yl]-6,9,12,21,24-pentaisobutyl-27-isopropyl-5,11,15,18,20,26,29-heptamethyl-4,7,10,13,16,19,22,25,28,31-decaoxo-2,5,8,11,14,17,20,23,26,29,32-undecaazatetratriacontan-34-oate (crude 78 g, theoretical 69.4 g) as pale brown powder. Obtained crude product was used in next reaction without further purification.

Prep. 118

To a solution of the object compound of Prep. 4 (100 mg) was added (2R)-2-[(tert-butoxycarbonyl)(methyl)amino]butanoic acid (27.6 mg), Bop-Cl (43.2 mg), and diisopropylethylamine (59 μl) under ice bath cooling. The mixture was stirred for 13 hrs at ambient temperature, and extracted with AcOEt. The organic phase was washed with 10% citric acid aqueous solution, saturated NaHCO$_3$ aqueous solution, and brine, and dried over Na$_2$SO$_4$. Solvent was removed in vacuo, and the residue was purified by preparative thin layer chromatography (CHCl$_3$:MeOH=90:10) to give methyl (6R,9S,12S,15S,18S,21R,24S,27S,30S,33S,36S)-9-sec-butyl-6-ethyl-36-(1-hydroxyethyl)-33-[(1R,2R,4E)-1-hydroxy-2-methyl-4-hexen-1-yl]-12,15,24,27-tetraisobutyl-30-isopropyl-2,2,5,8,14,18,21,23,29,32-decamethyl-4,7,10,13,16,19,22,25,28,31,34-undecaoxo-3-oxa-5,8,11,14,17,20,23,26,29,32,35-undecaazaheptatriacontan-37-oate (64.8 mg) as colorless solid.

The compounds of Prep. 119-127 were obtained in a similar manner to that of Prep. 118.

Prep. 128

To a solution of the object compound of Prep. 118 (64.8 mg) in CH$_2$Cl$_2$ (1.2 ml) was added TFA (0.36 ml) under ice bath cooling, and the mixture was stirred for 2 hrs under ice bath cooling. To the resulting solution was added saturated NaHCO$_3$ aqueous solution to adjust pH=8. The mixture was extracted with AcOEt, and the organic phase was washed with saturated NaHCO$_3$ aqueous solution and brine. Solvent was removed in vacuo to give methyl (3R,6S,9S,12S,15S,18R,21S,24S,27S,30S,33S)-6-sec-butyl-3-ethyl-33-(1-hydroxyethyl)-30-[(1R,2R,4E)-1-hydroxy-2-methyl-4-hexen-1-yl]-9,12,21,24-tetraisobutyl-27-isopropyl-5,11,15,18,20,26,29-heptamethyl-4,7,10,13,16,19,22,25,28,31-decaoxo-2,5,8,11,14,17,20,23,26,29,32-undecaazatetratriacontan-34-oate (58.6 mg). Obtained product was used in next reaction without further purification.

The compounds of Prep. 129-137 were obtained in a similar manner to that of Prep. 128.

Preparation 138

To a solution of the object compound of Prep. 168 below (3.70 g) in AcOEt (40 ml) was added a solution of isothiocyanatobenzene (757 mg) in AcOEt (10 ml) at room temperature. After being stirred for 30 minutes at the same temperature, N,N-dimethylaminopropylamine (752 mg) was added to the solution. The solution was stirred for 15 minutes, washed with 0.2N HCl, NaHCO$_3$, and brine, dried over MgSO$_4$, and concentrated in vacuo to give a powder. The resulting powder was dissolved in MeCN (100 ml) and 1N HCl (60 ml) was added under ice-bath cooling. After being stirred at room temperature for 6 hrs, the solution was neutralized with 1N Na$_2$CO$_3$ (50 ml), concentrated in vacuo to remove MeCN, and extracted with AcOEt (200 ml). The organic layer was washed with NaHCO$_3$ and brine, dried over MgSO$_4$, and concentrated in vacuo. The residue was purified by Silica-gel column (eluent:2% MeOH in CHCl$_3$) to give methyl (3S,6S,9S,12S,15R,18S,21S,24S,27S,30S)-30-[(1R)-1-hydroxyethyl]-27-[(1R,2R,4E)-1-hydroxy-2-methyl-4-hexen-1-yl]-3,6,9,18,21-pentaisobutyl-24-isopropyl-8,12,15,17,23,26,32-heptamethyl-4,7,10,13,16,19,22,25,28,31-decaoxo-2,5,8,11,14,17,20,23,26,29,32-undecaazatetriacontan-34-oate (3.19 g) as a powder.

Prep. 139

To a solution of the object compound of Prep. 128 (58.6 mg) in MeOH (1.2 ml) was added 1N NaOH (0.23 ml) at ambient temperature and the mixture was stirred for 2 hrs. To the reaction mixture was added 10% citric acid aqueous solution to adjust pH=4, and the solution was extracted with AcOEt. The organic phase was washed with brine, and was dried over Na2SO$_4$. Solvent was removed in vacuo and the residue was triturated with Et$_2$O to give (3R,6S,9S,12S,15S,18R,21S,24S,27S,30S,33S)-6-sec-butyl-3-ethyl-33-(1-hydroxyethyl)-30-[(1R,2R,4E)-1-hydroxy-2-methyl-4-hexen-1-yl]-9,12,21,24-tetraisobutyl-27-isopropyl-5,11,15,18,20,26,29-heptamethyl-4,7,10,13,16,19,22,25,28,31-decaoxo-2,5,8,11,14,17,20,23,26,29,32-undecaazatetratriacontan-34-oic acid (58.6 mg) as colorless powder.

The compounds of Prep. 140-148 were obtained in a similar manner to that of Prep. 139.

Prep. 149

Methyl (6R,9S,12S,15S,18S,21R,24S,27S,30S,33S,36S)-9-(1-tert-butoxyethyl)-6-ethyl-36-[(1R)-1-hydroxyethyl]-33-[(1R,2R,4E)-1-hydroxy-2-methyl-4-hexen-1-yl]-12,15,24,27-tetraisobutyl-30-isopropyl-2,2,5,8,14,18,21,23,29,32-decamethyl-4,7,10,13,16,19,22,25,28,31,34-undecaoxo-3-oxa-5,8,11,14,17,20,23,26,29,32,35-undecaazaheptatriacontan-37-oate (110 mg) was dissolved in 20% TFA/CH$_2$Cl$_2$ (3 ml) under ice-bath cooling. After being stirred at the same temperature for 4 hrs, to the solution was added saturated NaHCO$_3$ aqueous solution to be pH 8. The mixture was extracted with CHCl$_3$ (20 ml) and the organic layer was washed with saturated NaHCO$_3$ and brine, dried over MgSO$_4$, and concentrated in vacuo. The resulting residue was dissolved in MeOH (4 ml). To the solution was added 1N LiOH (0.77 ml) under ice-bath cooling. After being stirred for 1 hr at the same temperature, the solution was acidified with 5% citric acid aqueous solution to be pH 5, concentrated in vacuo to remove MeOH, and extracted with AcOEt (20 ml). The organic layer was washed with brine, dried over MgSO$_4$, and concentrated in vacuo. The resulting residue was triturated with Et$_2$O to give (3R,6S,9S,12S,15S,18R,21S,24S,27S,30S,33S)-3-ethyl-33-[(1R)-1-hydroxyethyl]-6-(1-hydroxyethyl)-30-[(1R,2R,4E)-1-hydroxy-2-methyl-4-hexen-1-yl]-9,12,21,24-tetraisobutyl-27-isopropyl-5,11,15,18,20,26,29-heptamethyl-4,7,10,13,16,19,22,25,28,31-decaoxo-2,5,8,11,14,17,20,23,26,29,32-undecaazatetratriacontan-34-oic acid (70 mg) as a solid.

The compounds of Prep. 150 and 151 were obtained in a similar manner to that of Prep. 149.

Prep. 152

The object compound of Prep. 90 (6.00 g) was dissolved in 20% TFA in CH$_2$Cl$_2$ (80 ml) under ice-bath cooling and the mixture was stirred at the same temperature for 4 hrs. To the solution was added saturated NaHCO$_3$ aqueous solution to be pH 0.8 and the mixture was extracted with CHCl$_3$ (200 ml). The organic layer was washed with saturated NaHCO$_3$ and brine, dried over MgSO$_4$, and concentrated to give methyl (5S,8S,11S,14S,17S,20R,23S,26S,29S,32S,38S,39R)-38-amino-39-hydroxy-5-[(1R)-1-hydroxyethyl]-8-[(1R,2R,4E)-1-hydroxy-2-methyl-4-hexen-1-yl]-14,17,26,29,32-pentaisobutyl-11-isopropyl-3,9,12,18,20,23,27,33,36-nonamethyl-4,7,10,13,16,19,22,25,28,31,34,37-dodecaoxo-3,6,9,12,15,18,21,24,27,30,33,36-dodecaazatetracontan-1-oate (5.70 g) as an amorphous powder.

The compound of Prep. 153 was obtained in a similar manner to that of Prep. 152.

Preparation 154

To a solution of the object compound of Prep. 155 below (crude 75.0 g, theoretical 71.8 g) in a mixed solvent (AcOEt 750 ml and pyridine 67.5 ml) was added isothiocyanatobenzene (19.8 ml), and the mixture was stirred for 13 hrs. To the mixture was added pyridine (67.5 ml) and diisopropylethylamine, and the pH value of the mixture was adjusted to 8. The mixture was stirred for 3 hrs. To the resulting solution was added N,N-dimethylpropanediamine (19.8 g) and stirred for 5 minutes. The reaction mixture was poured into 0.5N HCl (1 l) and extracted with AcOEt. The organic phase was washed with 0.5N HCl, saturated NaHCO$_3$ aqueous solution, and brine, and dried over Na$_2$SO$_4$. Solvent was removed in vacuo to give methyl (3S,9S,12S,15S,18S,21R,24S,27S,30S,33S,36S)-1-anilino-3,36-bis[(1R)-1-hydroxyethyl]-33-[(1R,2R,4E)-1-hydroxy-2-methyl-4-hexen-1-yl]-9,12,15,24,27-pentaisobutyl-30-isopropyl-5,8,14,18,21,23,29,32-octamethyl-4,7,10,13,16,19,22,25,28,31,34-undecaoxo-1-thioxo-2,5,8,11,14,17,20,23,26,29,32,35-dodecaazaheptatriacontan-37-oate (crude 84 g, theoretical 82.5 g) as brown form. Obtained crude product was used in next reaction without further purification.

Prep. 155

To a solution of the object compound of Prep. 157 below (crude 80.2 g theoretical 77.1 g) in CH$_2$Cl$_2$ was added TFA (205 ml) under ice bath cooling. The mixture was stirred for 2 hrs under ice bath cooling. The pH value of the solution was adjusted with a solution of Na$_2$CO$_3$ (147 g/500 ml H$_2$O) and saturated NaHCO$_3$ aqueous solution under ice bath cooling. The resulting solution was extracted with CHCl$_3$. The organic phase was washed with saturated NaHCO$_3$ solution and brine, and dried over Na$_2$SO$_4$. Solvent was removed in vacuo to give methyl (2S,5S,8S,11S,14S,17R,20S,23S,26S,29S,35S,36R)-35-amino-36-hydroxy-2-[(1R)-1-hydroxyethyl]-5-[(1R,2R,4E)-1-hydroxy-2-methyl-4-hexen-1-yl]-11,14,23,26,29-pentaisobutyl-8-isopropyl-6,9,15,17,20,24,30,33-octamethyl-4,7,10,13,16,19,22,25,28,31,34-undecaoxo-3,6,9,12,15,18,21,24,27,30,33-undecaazaheptatriacontan-1-oate (75 g, crude) as brown powder. Obtained crude product was used in next reaction without further purification.

Prep. 156

To a solution of (3S,6S,9S,12R,15S,18S,21S,24S,30S,33S)-30-[(1R)-1-hydroxyethyl]-33-[(1R,2R,4E)-1-hydroxy-2-methyl-4-hexen-1-yl]-6,9,18,21,24-pentaisobutyl-3-isopropyl-1,4,10,12,15,19,25,28-octamethyl-1,4,7,10,13,16,19,22,25,28,31-undecaazacyclotritriacontane-2,5,8,11,14,17,20,23,26,29,32-undecone (100 g) in tetrahydrofuran (1 l) was added 4-methylbenzenesulfonic acid (70.6 g) and the mixture was stirred at 50° C. for 14 hrs. To the mixture was added 1N NaOH and neutralized under ice bath cooling, and was added Boc$_2$O (17.9 g). The pH value of the mixture was adjusted to 8 with 1N NaOH under ice bath cooling. The mixture was stirred at ambient temperature for 2.5 hrs. Resulting mixture was concentrated in vacuo and extracted with AcOEt. The organic phase was washed with saturated Na$_2$CO$_3$ aqueous solution, 0.1N HCl, and brine, and dried over Na$_2$SO$_4$. Solvent was removed in vacuo to give tert-butyl {(3S,6S,9S,12S,15R,18S,21S,24S,27S,33S,34R)-3-[(1R,2R,4E)-1-hydroxy-2-methyl-4-hexen-1-yl]-9,12,21,24,27-pentaisobutyl-6-isopropyl-4,7,13,15,18,22,28,31,34-nonamethyl-2,5,8,11,14,17,20,23,26,29,32-undecaoxo-1-oxa-4,7,10,13,16,19,22,25,28,31-decaazacyclotetratriacontan-33-yl}carbamate (167.2 g) as brown form. Obtained crude product was used in next reaction without further purification.

Prep. 157

To a solution of the object compound of Prep. 167 below (71.0 g) in CH$_2$Cl$_2$ (1 l) was added methyl (2S,3R)-2-amino-37-hydroxybutanoate hydrochloride (10.8 g) and HOAt (10.8 g) at ambient temperature. To the mixture was added WSCD (9.9 g) under ice bath cooling. The mixture was stirred for 1.5 hrs at ambient temperature. The resulting mixture was concentrated in vacuo and extracted with AcOEt. The organic phase was washed with 0.5N HCl, saturated NaHCO$_3$, and brine, and dried over Na$_2$SO$_4$. Solvent was removed in vacuo to give methyl (6S,12S,15S,18S,21S,24R,27S,30S,33S,36S, 39S)-6,39-bis[(1R)-1-hydroxyethyl]-36-[(1R,2R,4E)-1-hydroxy-2-methyl-4-hexen-1-yl]-12,15,18,27,30-pentaisobutyl-33-isopropyl-2,2,8,11,17,21,24,26,32,35-decamethyl-4, 7,10,13,16,19,22,25,28,31,34,37-dodecaoxo-3-oxa-5,8,11, 14,17,20,23,26,29,32,35,38-dodecaazatetracontan-40-oate (80.2 g, crude) as brown form. Obtained-crude product was used in next reaction without further purification.

Prep. 158

To a solution of the object compound of Prep. 117 (crude 78 g, theoretical 69.4 g) in AcOEt (690 ml) was added isothiocyanatobenzene (11.3 g) at ambient temperature, and the mixture was stirred for 1 hr. To the solution was added diisopropylethylamine (5 ml), and the mixture was additionally stirred for 1.5 hrs. To the resulting solution was added N,N-dimethylpropanediamine (9.1 g) and stirred for 5 minutes. The reaction mixture was poured into 0.5N HCl (1 l) and extracted with AcOEt. The organic phase was washed with 0.5N HCl, saturated NaHCO$_3$ aqueous solution, and brine, and dried over Na$_2$SO$_4$. Solvent was removed in vacuo to give methyl (6S,9S,12S,15S,18R,21S,24S,27S,30S,33S)-1-anilino-33-[(1R)-1-hydroxyethyl]-30-[(1R,2R,4E)-1-hydroxy-2-methyl-4-hexen-1-yl]-6,9,12,21,24-pentaisobutyl-27-isopropyl-2,5,11,15,18,20,26,29-octamethyl-4,7,10,13, 16,19,22,25,28,31-decaoxo-1-thioxo-2,5,8,11,14,17,20,23, 26,29,32-undecaazatetratriacontan-34-oate (crude 78 g, theoretical 76.9 g) as brown form. Obtained crude product was used in next reaction without further purification.

Prep. 159

To a solution of the object compound of Prep. 1 (87 mg) was added (2R)-2-{[(9H-fluoren-9-ylmethoxy)carbonyl] (methyl)amino}propanoic acid (36 mg), Bop-Cl (28.2 mg), and diisopropylethylamine (39 µl) under ice bath cooling. The mixture was stirred for 13 hrs at ambient temperature, and extracted with AcOEt. The organic phase was washed with 10% citric acid aqueous solution, saturated NaHCO$_3$ aqueous solution, and brine, and dried over Na$_2$SO$_4$. Solvent was removed in vacuo, and the residue was purified by preparative thin layer chromatography (CHCl$_3$:MeOH=90' 10) to give methyl (5R,8S,11S,14S,17S,20R,23S,26S,29S,32S, 35S)-1-(9H-fluoren-9-yl)-35-[(1R)-1-hydroxyethyl]-32-[(1R,2R,4E)-1-hydroxy-2-methyl-4-hexen-1-yl]-8,11,14, 23,26-pentaisobutyl-29-isopropyl-4,5,7,13,17,20,22,28,31-nonamethyl-3,6,9,12,15,18,21,24,27,30,33-undecaoxo-2-oxa-4,7,10,13,16,19,22,25,28,31,34-undecaazahexatriacontan-36-oate (110 mg) as colorless solid.

The compound of Prep. 160 was obtained in a similar manner to that of Prep. 159.

Prep. 161

To a solution of the object compound of Prep. 95 (1.55 g) in dioxane (30 ml) was added 1N LiOH (10 ml) under ice-bath cooling. After being stirred for 3 hrs at the same temperature, the solution was acidified with 5% citric acid to be pH 5, concentrated in vacuo to remove dioxane, and extracted with AcOEt (50 ml). The organic layer was washed with brine, dried over MgSO$_4$, and concentrated in vacuo. The resulting residue was triturated with Et$_2$O to give (5S,8S,11S,14S,17S, 20R,23S,26S,29S,32S)-5-[(1R)-1-hydroxyethyl]-8-[(1R, 2R,4E)-1-hydroxy-2-methyl-4-hexen-1-yl]-14,17,26,29-tetraisobutyl-11-isopropyl-3,9,12,18,20,23,27,33,35,35-decamethyl-32-(methylamino)-4,1,10,13,16,19,22,25,28, 31-decaoxo-34-oxa-3,6,9,12,15,18,21,24,27,30-decaazahexatriacontan-1-oic acid as a solid.

The compounds of Prep. 162-165 were obtained in a similar manner to that of Prep. 161.

Prep. 166

To a solution of the object compound of Prep. 138 (3.15 g) in AcOEt (40 ml) was added a solution of isothiocyanatobenzene (511 mg) in AcOEt (10 ml) at room temperature. After being stirred for 30 minutes at the same temperature, N,N-dimethylaminopropylamine (527 mg) was added to the solution. The solution was stirred for 15 minutes, washed with 0.2N HCl, NaHCO$_3$, and brine, dried over MgSO$_4$, and concentrated in vacuo to give a powder. The resulting powder was dissolved in MeCN (100 ml) and 1N HCl (50 ml) was added under ice-bath cooling. After being stirred at room temperature for 6 hrs, the solution was neutralized with 1N Na$_2$CO$_3$ (25 ml), concentrated in vacuo to remove MeCN, and extracted with AcOEt (150 ml). The organic layer was washed with NaHCO$_3$ and brine, dried over MgSO$_4$, and concentrated in vacuo. The residue was purified by Silica-gel column (eluent:2% MeOH in CHCl$_3$) to give methyl (5S,8S, 11S,14S,17S,20R,23S,26S,29S)-29-amino-5-[(1R)-1-hydroxyethyl]-8-[(1R,2R,4E)-1-hydroxy-2-methyl-4-hexen-1-yl]-14,17,26-triisobutyl-11-isopropyl-3,9,12,18,20,23,27, 31-octamethyl-4,7,10,13,16,19,22,25,28-nonaoxo-3,6,9,12, 15,18,21,24,27-nonaazadotriacontan-1-oate (2.72 g) as a powder.

Prep. 167

To a solution of the object compound of Prep. 156 (crude 167 g, theoretical 108 g) in MeOH (1 l) was added 1N NaOH (819 ml) under ice bath cooling. The mixture was stirred at ambient temperature for 8 hrs. To the mixture was added 1N NaOH (82 ml) and the mixture was stirred for 2 hrs. The resulting mixture was neutralized with 1N HCl and concentrated in vacuo. The residual solution was acidified (pH=3) with 1N HCl and extracted with AcOEt. The organic phase was washed with 0.1N HCl and brine, and dried over MgSO$_4$. The solvent was removed in vacuo. The resulting oil was triturated with AcOEt:hexane=450 ml: 1500 ml to give (6S, 12S,15S,18S,21S,24R,27S,30S,33S,36S)-6-[(1R)-1-hydroxyethyl]-36-[(1R,2R,4E)-1-hydroxy-2-methyl-4-hexen-1-yl]-12,15,18,27,30-pentaisobutyl-33-isopropyl-2,2,8,11, 17,21,24,26,32,35-decamethyl-4,7,10,13,16,19,22,25,28, 31,34-undecaoxo-3-oxa-5,8,11,14,17,20,23,26,29,32,35-undecaazaheptatriacontan-37-oic acid (80.4 g).

Prep. 168

To a solution of the object compound of Prep. 152 (5.70 g) in AcOEt (100 ml) was added a solution of isothiocyanatobenzene (1.08 g) in AcOEt (10 ml) at room temperature. After being stirred for 2 hrs at the same temperature, N,N-dimethylaminopropylamine (820 mg) was added to the solution. The solution was stirred for 15 minutes, washed with 0.2N HCl, NaHCO$_3$, and brine, dried over MgSO$_4$, and concentrated in vacuo to give a powder. The resulting powder was dissolved in MeCN (100 ml) and 1N HCl (100 ml) was added under ice-bath cooling. After being stirred at room temperature for 6 hrs, the solution was neutralized with 1N Na$_2$CO$_3$ (50 ml), concentrated in vacuo to remove MeCN, and extracted with AcOEt (200 ml). The organic layer was washed with NaHCO$_3$ and brine, dried over MgSO$_4$, and concentrated in vacuo. The residue was purified by Silica-gel column (eluent: 2% MeOH in CHCl$_3$) to give methyl (6S,9S,12S,15S,18R, 21S,24S,27S,30S,33S)-33-[(1R)-1-hydroxyethyl]-30-[(1R, 2R,4E)-1-hydroxy-2-methyl-4-hexen-1-yl]-6,9,12,21,24-pentaisobutyl-27-isopropyl-5,11,15,18,20,26,29,35-octamethyl-4,7,10,13,16,19,22,25,28,31,34-undecaoxo-2,5,8,11,14,17,20,23,26,29,32,35-dodecaazaheptatriacontan-37-oate (3.77 g) as a powder.

Prep. 169

To a solution of methyl (3S,6S,9S,12S,15R,18S,21S,24S,27S,30S)-3-sec-butyl-30-[(1R)-1-hydroxyethyl]-27-[(1R,2R,4E)-1-hydroxy-2-methyl-4-hexen-1-yl]-6,9,18,21-tetraisobutyl-24-isopropyl-8,12,15,17,23,26,32-heptamethyl-4,7,10,13,16,19,22,25,28,31-decaoxo-2,5,8,11,14,17,20,23,26,29,32-undecaazatetratriacontan-34-oate (230 mg) in MeOH (4 ml) was added 1N LiOH (1.84 ml) under ice-bath cooling. After being stirred for 1 hr at the same temperature, the solution was acidified with 5% citric acid to be pH 5, concentrated in vacuo to remove MeOH, and extracted with AcOEt (20 ml). The organic layer was washed with brine, dried over MgSO$_4$, and concentrated in vacuo. The resulting residue was triturated with Et$_2$O to give (3S,6S,9S,12S,15R,18S,21S,24S,27S,30S)-3-sec-butyl-30-[(1R)-1-hydroxyethyl]-27-[(1R,2R,4E)-1-hydroxy-2-methyl-4-hexen-1-yl]-6,9,18,21-tetraisobutyl-24-isopropyl-8,12,15,17,23,26,32-heptamethyl-4,7,10,13,16,19,22,25,28,31-decaoxo-2,5,8,11,14,17,20,23,26,29,32-undecaazatetratriacontan-34-oic acid (188 mg) as a solid.

The compounds of Prep. 170-177 were obtained in a similar manner to that of Prep. 169.

Prep. 178

To a solution of the object compound of Prep. 1 (66 mg) in CH$_2$Cl$_2$ (2.5 ml) was added (2R)-2-[(tert-butoxycarbonyl) (methyl)amino]-4-methylpentanoic acid (16.5 mg) and HOAt (9.1 mg), and WSCD (10.4 mg) under ice bath cooling, and the mixture was stirred for 1.5 hrs under ice bath cooling. The resulting mixture was concentrated in vacuo and the residue was extracted with AcOEt. The organic phase was washed with saturated NaHCO$_3$ aqueous solution, and brine, and dried over Na$_2$SO$_4$. Solvent was removed in vacuo to give methyl (6R,9S,12S,15S,18S,21R,24S,27S,30S,33S,36S)-36-[(1R)-1-hydroxyethyl]-33-[(1R,2R,4E)-1-hydroxy-2-methyl-4-hexen-1-yl]-6,9,12,15,24,27-hexaisobutyl-30-isopropyl-2,2,5,8,14,18,21,23,29,32-decamethyl-4,7,10,13,16,19,22,25,28,31,34-undecaoxo-3-oxa-5,8,11,14,17,20,23,26,29,32,35-undecaazaheptatriacontan-37-oate (57 mg) as pale yellow powder. Obtained product was used in next reaction without further purification.

The compounds of Prep. 179-192 were obtained in a similar manner to that of Prep. 178

Prep. 193

To a solution of the object compound of Prep. 178 (57 mg) in CH$_2$Cl$_2$ (1.2 ml) was added TFA (0.3 ml) under ice bath cooling, and the mixture was stirred for 2 hrs under ice bath cooling. Resulting mixture was neutralized with NaHCO$_3$ aqueous solution (430 mg in 20 ml H2O) under ice bath cooling, and concentrated in vacuo. To the residual solution was added saturated NaHCO$_3$ aqueous solution to adjust pH=8, and the mixture was extracted with AcOEt. The organic phase was washed with saturated NaHCO$_3$ aqueous solution and brine, and dried over NaSO$_4$. Solvent was removed in vacuo to give methyl (3R,6S,9S,12S,15S,18R,21S,24S,27S,30S,33S)-33-[(1R)-1-hydroxyethyl]-30-[(1R,2R,4E)-1-hydroxy-2-methyl-4-hexen-1-yl]-3,6,9,12,21,24-hexaisobutyl-27-isopropyl-5,11,15,18,20,26,29-heptamethyl-4,7,10,13,16,19,22,25,28,31-decaoxo-2,5,8,11,14,17,20,23,26,29,32-undecaazatetratriacontan-34-oate (53 mg) as colorless solid.

The compounds of Prep. 194-207 were obtained in a similar manner to that of Prep. 193.

Prep. 208

To a solution of the object compound of Prep. 57 (1.00 g), (2S)-2-{[(9H-fluoren-9-ylmethoxy)carbonyl](methyl) amino}propanoic acid (399 mg), and Bop-Cl (416 mg) in CH$_2$Cl$_2$ (20 ml) was added N-ethyl-N-isopropyl-2-propanamine (422 mg) under ice-bath cooling. After being stirred at room temperature over night, the reaction solution was concentrated in vacuo. The residue was dissolved in AcOEt (50 ml) and the solution was washed with 0.5N HCl, 1M NaHCO$_3$, and brine, dried over MgSO$_4$, and concentrated in vacuo. The resulting residue was purified by Silica-gel column (eluent:2% MeOH in CHCl$_3$) to give methyl (5R,8S,11S,14S,17S,20R,23S,26S,29S,32S,35S)-8-(1-tert-butoxyethyl)-1-(9H-fluoren-9-yl)-35-[(1R)-1-hydroxyethyl]-32-[(1R,2R,4E)-1-hydroxy-2-methyl-4-hexen-1-yl]-11,14,23,26-tetraisobutyl-29-isopropyl-4,5,7,13,17,20,22,28,31-nonamethyl-3,6,9,12,15,18,21,24,27,30,33-undecaoxo-2-oxa-4,7,10,13,16,19,22,25,28,31,34-undecaazahexatriacontan-36-oate (1.25 g) as an amorphous powder.

The compounds of Prep. 209-212 were obtained in a similar manner to that of Prep. 208.

Prep. 213

To a solution of the object compound of Prep. 159 (110 mg) in dioxane (2.4 ml) was added 1N NaOH (0.6 ml) at ambient temperature and the mixture was stirred for 2-hrs. To the reaction mixture was added 10% citric acid aqueous solution to adjust pH=4, and the solution was extracted with AcOEt. The organic phase was washed with brine, and was dried over Na$_2$SO$_4$. Solvent was removed in vacuo and the residue was triturated with Et$_2$O to give (3R,6S,9S,12S,15S,18R,21S,24S,27S,30S,33S)-33-[(1R)-1-hydroxyethyl]-30-[(1R,2R,4E)-1-hydroxy-2-methyl-4-hexen-1-yl]-6,9,12,21,24-pentaisobutyl-27-isopropyl-3,5,11,15,18,20,26,29-octamethyl-4,7,10,13,16,19,22,25,28,31-decaoxo-2,5,8,11,14,17,20,23,26,29,32-undecaazatetratriacontan-34-oic acid (79 mg) as colorless powder.

The compound of Prep. 214 was obtained in a similar manner to that of Prep. 213.

Prep. 215

To a solution of the object compound of Prep. 110 (193 mg) was dissolved in 10% TFA in CH$_2$Cl$_2$ (6 ml) under ice-bath cooling. After being stirred at the same temperature for 2 hrs, to the reaction solution was added 1M NaHCO$_3$ aqueous solution to be pH=8. The reaction mixture was extracted with CHCl$_3$ (50 ml) and the organic layer was washed with saturated NaHCO$_3$ aqueous solution and brine, dried over MgSO$_4$, and concentrated in vacuo. The resulting residue was purified by Silica-gel column (eluent: 2% MeOH in CHCl$_3$) to give (1R)-1-{(2S,5R,8S,11S,14S,17S,20R,23S,26S,29S,32S)-8-(1-hydroxyethyl)-32-[(1R,2R,4E)-1-hydroxy-2-methylhex-4-en-1-yl]-11,14,23,26-tetraisobutyl-29-isopropyl-4,5,7,13,17,20,22,28,31-nonamethyl-3,6,9,12,15,18,21,24,27,30,33-undecaoxo-1,4,7,10,13,16,19,22,25,28,31-undecaazacyclotritriacontan-2-yl}ethyl acetate (183 mg) as an amorphous powder.

Prep. 216

To a solution of the object-compound of Prep. 215 (187 mg) in CH$_2$Cl$_2$ (1.2 ml) were added 4-nitrophenyl chloroformate (54 mg) and N-methylmorpholine (29 µl). After the mixture was stirred overnight, three further portions of 4-nitrophenyl chloroformate (54 mg) and N-methylmorpholine (29 µl) were added at intervals of 1 hour. After the starting compound was consumed, the mixture was diluted with AcOEt, washed with 1 N aqueous hydrochloric acid and aqueous NaHCO$_3$, dried over MgSO$_4$ and concentrated. The residue was chromatographed on silica gel (hexane/AcOEt=1/4 and then CH$_2$Cl$_2$/MeOH=9/1) to give (1R)-1-[(2S,5R,8S,11S,14S,17S,20R,23S,26S,29S,32S)-32-[(1R,2R,4E)-1-hydroxy-2-methylhex-4-en-1-yl]-11,14,23,26-tetraisobutyl-29-isopropyl-4,5,7,13,17,20,22,28,31-nonamethyl-8-(1-{[(4-nitrophenoxy)carbonyl]oxy}ethyl)-3,6,9,12,15,18,21,24,27,30,33-undecaoxo-1,4,7,10,13,16,19,22,25,28,31-undecaazacyclotritriacontan-2-yl]ethyl acetate (87 mg).

Prep. 217

To a solution of the object compound of Prep. 216 (27 mg) in tetrahydrofuran (1 ml) was added morpholine (4.9 µl), and the mixture was stirred at room temperature overnight. The residue was chromatographed on silica gel (CH$_2$Cl$_2$/MeOH=97/3 to 90/10) to give 1-{(2S,5S,8S,11S,14R,17S,20S,23S,26S,29S,32R)-29-[(1R)-1-acetoxyethyl]-26-[(1R,2R,4E)-1-hydroxy-2-methylhex-4-en-1-yl]-5,8,17,20-tetraisobutyl-23-isopropyl-1,7,11,14,16,22,25,31,32-nonamethyl-3,6,9,12,15,18,21,24,27,30,33-undecaoxo-1,4,7,10,13,16,19,22,25,28,31-undecaazacyclotritriacontan-2-yl}ethyl morpholine-4-carboxylate (22 mg).

The compounds of Prep. 218-220 were obtained in a similar manner to that of Prep. 217, and the compound of Ex. 1 was obtained in a similar manner to that of Prep. 4.

Ex. 2

To a solution of the object compound of Prep. 139 (42.7 mg) in CH$_2$Cl$_2$ (43 ml) was added HOAt (5.5 mg) and WSCD (6.3 mg) under ice bath cooling, and the mixture was stirred at 5° C. for 13 hrs. The reaction mixture was concentrated in vacuo and the residue was extracted with AcOEt. The organic phase was washed with H$_2$O, 10% citric acid aqueous solution, saturated NaHCO$_3$ aqueous solution, and brine, and was dried over Na$_2$SO$_4$. Solvent was removed in vacuo, and the residue was purified by preparative thin layer chromatography (CHCl$_3$:MeOH=95:5) to give (3R,6S,9S,12S,15S,18S,21R,24S,27S,30S,33S)-33-sec-butyl-3-ethyl-6-(1-hydroxyethyl)-9-[(1R,2R,4E)-1-hydroxy-2-methyl-4-hexen-1-yl]-15,18,27,30-tetraisobutyl-12-isopropyl-1,4,10,13,19,21,24,28-octamethyl-1,4,7,10,13,16,19,22,25,28,31-undecaazacyclotritriacontane-2,5,8,11,14,17,20,23,26,29,32-undecone (29 mg) as colorless powder.

The compounds of Ex. 3-11 were obtained in a similar manner to that of Ex. 2.

Ex. 12

The object compound of Ex. 25 below (1.00 g) was dissolved in 10% TFA in CH$_2$Cl$_2$ (10 ml) under ice-bath cooling. After being stirred at the same temperature for 2 hrs, to the reaction solution was added 1M NaHCO$_3$ aqueous solution to be pH 8. The reaction mixture was extracted with CHCl$_3$ (50 ml) and the organic layer was washed with saturated NaHCO$_3$ aqueous solution and brine, dried over MgSO$_4$, and concentrated in vacuo. The resulting residue was purified by Silica-gel column (eluent:2% MeOH in CHCl$_3$) to give (3R,6S,9S,12S,15S,18S,21R,24S,27S,30S,33S)-6-[(1R)-1-hydroxyethyl]-33-(1-hydroxyethyl)-9-[(1R,2R,4E)-1-hydroxy-2-methyl-4-hexen-1-yl]-15,18,27,30-tetraisobutyl-12-isopropyl-1,3,4,10,13,19,21,24,28-nonamethyl-1,4,7,10,13,16,19,22,25,28,31-undecaazacyclotritriacontane-2,5,8,11,14,17,20,23,26,29,32-undecone (62.5 mg) as an amorphous powder.

The compound of Ex. 13 was obtained in a similar manner to that of Ex. 12.

Ex. 14

To a solution of the object compound of Prep. 41 (42.7 mg) in CH$_2$Cl$_2$ (48 ml) was added HOAt (7.3 mg) and WSCD (8.3 mg) under ice bath cooling, and the mixture was stirred at 5° C. for 13 hrs. The reaction mixture was concentrated in vacuo and the residue was extracted with AcOEt. The organic phase was washed with H$_2$O, 10% citric acid aqueous solution, saturated NaHCO$_3$ aqueous solution, and brine, and was dried over Na$_2$SO$_4$. Solvent was removed in vacuo, and the residue was purified by preparative thin layer chromatography (CHCl$_3$:MeOH=95:5) to give (3R,6S,9S,12S,15S,18S,21R,24S,27S,30S,33S)-33-sec-butyl-6-[(1R)-1-hydroxyethyl]-9-[(1R,2R,4E)-1-hydroxy-2-methyl-4-hexen-1-yl]-15,18,27,30-tetraisobutyl-12-isopropyl-1,3,4,10,13,19,21,24,28-nonamethyl-1,4,7,10,13,16,19,22,25,28,31-undecaazacyclotritriacontane-2,5,8,11,14,17,20,23,26,29,32-undecone (29 mg) as colorless powder.

The compounds of Ex. 15-24 were obtained in a similar manner to that of Ex. 14.

Example 25

To a solution of the object compound of Prep. 20 (785 mg) and HOAt (99 mg) in CH$_2$Cl$_2$ (785 ml) was added a solution of WSCD (113 mg) in CH$_2$Cl$_2$ (10 ml) for 3 hrs under ice-bath cooling. After being stirred at 5° C. overnight, the solution was concentrated in vacuo. The residue was dissolved in AcOEt (40 ml)-H$_2$O (40 ml), the solution was washed with 0.2N HCl, saturated NaHCO$_3$, and brine, dried over MgSO$_4$, and concentrated in vacuo to give a powder. The crude powder was purified by Silica-gel column chromatography (eluent Hexane:Acetone, 2:1) to give (3R,6S,9S,12S,15S,18S,21R,24S,27S,30S,33S)-33-(1-tert-butoxyethyl)-6-[(1R)-1-hydroxyethyl]-9-[(1R,2R,4E)-1-hydroxy-2-methyl-4-hexen-1-yl]-15,18,27,30-tetraisobutyl-12-isopropyl-1,3,4,10,13,19,21,24,28-nonamethyl-1,4,7,10,13,16,19,22,25,28,31-undecaazacyclotritriacontane-2,5,8,11,14,17,20,23,26,29,32-undecone (365 mg) as an amorphous powder.

The compounds of Ex. 26-35 were obtained in a similar manner to that of Ex. 25.

Ex. 36

To a solution of the object compound of Prep. 75 (48 mg) in CH$_2$Cl$_2$ (37 ml) was added HOAt (6.0 mg) and WSCD (6.9 mg) under ice bath cooling, and the mixture was stirred at 5° C. for 13 hrs. The reaction mixture was concentrated in vacuo and the residue was extracted with AcOEt. The organic phase was washed with H$_2$O, 10% citric acid aqueous solution, saturated NaHCO$_3$ aqueous solution, and brine, and was dried over Na$_2$SO$_4$. Solvent was removed in vacuo, and the residue was purified by preparative thin layer chromatography (CHCl$_3$:MeOH=95:5) to give, (3R,6S,9S,12S,15S,18S,21R,24S,27S,30S,33S)-6-[(1R)-1-hydroxyethyl]-9-[(1R,2R,4E)-1-hydroxy-2-methyl-4-hexen-1-yl]-3,15,18,27,30,33-hexaisobutyl-12-isopropyl-1,4,7,10,13,16,19,22,25,28,31-undecaazacyclotritriacontane-2,5,8,11,14,17,20,23,26,29,32-undecone (34 mg) as colorless powder.

The compounds of Ex. 37-51 were obtained in a similar manner to that of Ex. 36

Ex. 52

To a solution of the object compound of Prep. 161 (920 mg) and HOAt (489 mg) in CH$_2$Cl$_2$ (1000 ml) was added a solution of WSCD (558 mg) in CH$_2$Cl$_2$ (10 ml) and the mixture was stirred under ice-bath cooling. After being stirred at 5° C. overnight, the solution was concentrated in vacuo. The residue was dissolved in AcOEt (100 ml)-H$_2$O (100 ml), the solution was washed with 0.2N HCl, saturated NaHCO$_3$, and brine, dried over MgSO$_4$, and concentrated in vacuo to give a powder. The crude powder was purified by Silica-gel column chromatography (eluent: 4% MeOH in CHCl$_3$) to give (3S,6S,9S,12R,15S,18S,21S,24S,30S,33S)-24-(1-tert-butoxyethyl)-30-[(1R)-1-hydroxyethyl]-33-[(1R,2R,4E)-1-hydroxy-2-methyl-4-hexen-1-yl]-6,9,18,21-tetraisobutyl-3-isopropyl-1,4,10,12,15,19,25,28-octamethyl-1,4,7,10,13,16,19,22,25,28,31-undecaazacyclotritriacontane-2,5,8,11,14,17,20,23,26,29,32-undecone (448 mg) as an amorphous powder.

The compounds of Ex. 53-73 were obtained in a similar manner to that of Ex. 52.

Ex. 74

To a solution of the object compound of Prep. 213 (79 mg) in CH$_2$Cl$_2$ (63 ml) was added HOAt (10.3 mg) and WSCD (11.7 mg) under ice bath cooling, and the mixture was stirred at 5° C. for 13 hrs. The reaction mixture was concentrated in vacuo and the residue was extracted with AcOEt. The organic phase was washed with H$_2$O, 10% citric acid aqueous solution, saturated NaHCO$_3$ aqueous solution, and brine, and was dried over Na$_2$SO$_4$. Solvent was removed in vacuo, and the residue was purified by preparative thin layer chromatography (CHCl$_3$:MeOH=95:5) to give (3R,6S,9S,12S,15S,18S,21R,24S,27S,30S,33S)-6-[(1R)-1-hydroxyethyl]-9-[(1R,2R,4E)-1-hydroxy-2-methyl-4-hexen-1-yl]-15,18,27,30,33-pentaisobutyl-12-isopropyl-1,3,4,10,13,19,21,24,28-nonamethyl-1,4,7,10,13,16,19,22,25,28,31-undecaazacyclotritriacontane-2,5,8,11,14,17,20,23,26,29,32-undecone (43 mg) as colorless powder.

Ex. 75

(3R,6S,9S,12S,15S,18S,21R,24S,27S,30S,33S)-3-[(Benzyloxy)methyl]-6-[(1R)-1-hydroxyethyl]-9-[(1R,2R)-1-hydroxy-2-methylhexyl]-15,18,27,30,33-pentaisobutyl-12-isopropyl-1,4,10,13,19,21,24,28-octamethyl-1,4,7,10,13,16,19,22,25,28,31-undecaazacyclotritriacontane-2,5,8,11,14,17,20,23,26,29,32-undecone (22 mg) are dissolved in MeOH (1 ml) and hydrogenated at room temperature and atmospheric pressure over 5% Pd on charcoal. After 2 hrs, the catalyst was filtered off and the filtrate was concentrated in vacuo under reduced pressure. The residue was purified by silica-gel column chromatography (hexane-acetone, 1:1) to yield (3R,6S,9S,12S,15S,18S,21R,24S,27S,30S,33S)-6-[(1R)-1-hydroxyethyl]-3-(hydroxymethyl)-9-[(1R,2R)-1-hydroxy-2-methylhexyl]-15,18,27,30,33-pentaisobutyl-12-isopropyl-1,4,10,13,19,21,24,28-octamethyl-1,4,7,10,13,16,19,22,25,28,31-undecaazacyclotritriacontane-2,5,8,11,14,17,20,23,26,29,32-undecone (18 mg).

Ex. 76

(3R,6S,9S,12S,15S,18S,21R,24S,27S,30S,33S)$_{7-3}$-[(Benzyloxy)methyl]-6-[(1R)-1-hydroxyethyl]-9-[(1R,2R,4E)-1-hydroxy-2-methyl-4-hexen-1-yl]-15,18,27,30-tetraisobutyl-12-isopropyl-33-(1-methoxyethyl)-1,4,10,13,19,21,24,28-octamethyl-1,4,7,10,13,16,19,22,25,28,31-undecaazacyclotritriacontane-2,5,8,11,14,17,20,23,26,29,32-undecone (20 mg) are dissolved in MeOH (2 ml) and hydrogenated at room temperature and atmospheric pressure over Pd on charcoal. After 40 minutes, the catalyst was filtered off and the filtrate was concentrated in vacuo under reduced pressure. The residue was purified by silica-gel preparative thin layer chromatography (CHCl$_3$:MeOH=95:5) to yield (3R,6S,9S,12S,15S,18S,21R,24S,27S,30S,33S)-6-[(1R)-1-hydroxyethyl]-3-(hydroxymethyl)-9-[(1R,2R)-1-hydroxy-2-methylhexyl]-15,18,27,30-tetraisobutyl-12-isopropyl-33-(1-methoxyethyl)-1,4,10,13,19,21,24,28-octamethyl-1,4,7,10,13,16,19,22,25,28,31-undecaazacyclotritriacontane-2,5,8,11,14,17,20,23,26,29,32-undecone (12 mg) as colorless powder.

Ex. 77

To a solution of the object compound of Prep. 217 (11.5 mg) in tetrahydrofuran (1 ml) was added sodium methanolate (25 mmol) in MeOH (1 ml), and the mixture was stirred at room temperature overnight. The mixture was submitted by ODS purification to give 1-{(2S,5S,8S,11S,14R,17S,20S,23S,26S,29S,32R)-29-[(1R)-1-hydroxyethyl]-2,6-[(1R,2R,4E)-1-hydroxy-2-methylhex-4-en-1-yl]-5,8,17,20-tetraisobutyl-23-isopropyl-1,7,11,14,16,22,25,31,32-nonamethyl-3,6,9,12,15,18,21,24,27,30,33-undecaoxo-1,4,7,10,13,16,19,22,25,28,31-undecaazacyclotritriacontan-2-yl}ethyl morpholine-4-carboxylate (9 mg).

The compounds of Ex. 78-80 were obtained in a similar manner to that of Ex. 77.

Ex. 81

A solution of (3R,6S,9S,12S,15S,18S,21R,24S,27S,30S,33S)-6-[(1R)-1-hydroxyethyl]-9-[(1R,2R,4E)-1-hydroxy-2-methylhex-4-en-1-yl]-15,18,27,30-tetraisobutyl-12-isopropyl-33-(1-methoxyethyl)-1,3,4,10,13,19,21,24,28-nonamethyl-1,4,7,10,13,16,19,22,25,28,31-undecaazacyclotritriacontane-2,5,8,11,14,17,20,23,26,29,32-undecone (60 mg) in MeOH (6.0 ml) was hydrogenated over 20% Pd/C (50% wet; 30 mg) at room temperature for 2 hrs. The mixture was filtered and the filtrate was concentrated. The residue was evaporated to give (3R,6S,9S,12S,15S,18S,21R,24S,27S,30S,33S)-6-[(1R)-1-hydroxyethyl]-9-[(1R,2R)-1-hydroxy-2-methylhexyl]-15,18,27,30-tetraisobutyl-12-isopropyl-33-(1-methoxyethyl)-1,3,4,10,13,19,21,24,28-nonamethyl-1,4,7,10,13,16,19,22,25,28,31-undecaazacyclotritriacontane-2,5,8,11,14,17,20,23,26,29,32-undecone (56 mg).

The compounds of Ex. 82 and 83 were obtained in a similar manner to that of Ex. 81.

The structure and the mass spectrometry data (ESI-MS [(M+H)$^+$] unless otherwise-indicated) for the compounds of Examples and Preparations are shown in Table 1~42, and the peak δ ppm of $^1$H-NMR data (chloroform-d, TMS internal standard) for the compounds of Examples are shown in Table 43.

Table 1~11: Example Compounds represented by following formula

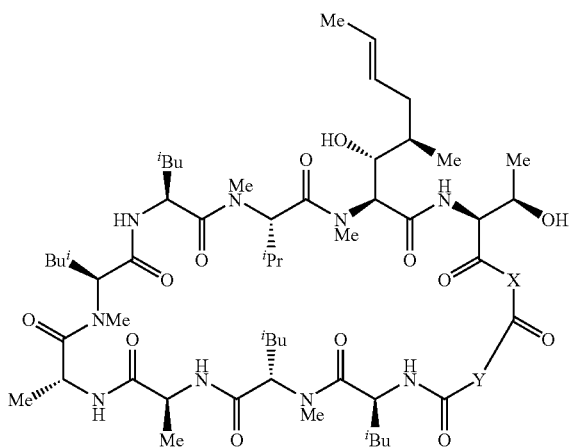

TABLE 1

| Ex. | R² | MS |
|---|---|---|
| 1 | —CH₂NHMe | 1263.5 |
| 6 | —CH₂OC(O)NMe₂ | 1321.4 |
| 9 | —CH₂OMe | 1264.5 |
| 11 | —CH₂OBn | 1340.7 |
| 16 | Et | 1249.1 |
| 18 | —CH₂NMeBoc | 1363.5 |
| 32 | Me | 1234.7 |
| 34 | Bn | 1310.5 |
| 69 | H | 1220.7 |
| 76 | —CH₂OH | 1252.6 |

TABLE 2

| Ex. | R² | MS |
|---|---|---|
| 5 | —CH₂OMe | 1282.9 |
| 15 | Me | 1253.4 |
| 19 | $^i$Bu | 1294.5 |
| 63 | H | 1239 |

TABLE 3

| Ex. | R² | R⁵ | MS |
|---|---|---|---|
| 2 | Et | Me | 1246.6 |
| 3 | $^n$Bu | | 1292.5 |
| 4 | —(CH₂)₃NMeCO₂Bn | | 1424.1 |
| 7 | —(CH₂)₄NMeCO₂Bn | | 1437.1 |
| 8 | —CH₂OC(O)NMe₂ | | 1319.7 |
| 10 | —CH₂OMe | | 1262.7 |
| 14 | Me | | 1232.7 |
| 21 | $^i$Bu | | 1274.8 |
| 23 | —CH₂O$^t$Bu | | 1304.8 |
| 62 | H | | 1219 |
| 27 | Me | Et | Negative (ESI⁻): 1246 [M − H] |

TABLE 4

| Ex. | R² | MS |
|---|---|---|
| 12 | Me | 1221 |
| 26 | Et | 1256 |
| 71 | H | 1206.6 |

TABLE 5

| Ex. | R³ | MS |
|---|---|---|
| 59 | $^t$BuOCH₂— | 1249 |
| 60 | Cy. Hex.-CH₂— | 1259 |
| 73 | Bn | 1252 |

TABLE 6
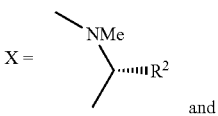
| Ex. | R² | R³ | R⁵ | MS |
|---|---|---|---|---|
| 13 | Me | ᶦPr | Et | 1233 |
| 31 |  | ⋮ | Me | 1218.6 |
| 17 | —CH₂-Cy. Hex. | ᵗBu |  | 1314.69 |
| 24 | Me | ⋮ |  | 1232.7 |
| 65 | H | ⋮ |  | 1218.6 |
| 20 | ᶦBu | Cy. Hex. |  | 1301.0 |
| 30 | Me | ⋮ |  | 1259 |
| 64 | H | ⋮ |  | 1245 |
| 25 | Me | BuᵗO⋯Me |  | 1277 |
| 29 | ᶦPr |  |  | 1305 |
| 35 | Et |  |  | 1291 |
| 52 | H |  |  | 1263 |
| 28 | Me | BnO⋯Me |  | 1310.5 |
| 57 | H |  |  | 1297 |
| 33 | Me | EtO⋯Me |  | 1248.3 |
| 53 | H | (CH₂)₂NMeCO₂Bn |  | 1353.7 |
| 54 | H | Et⋯Me | H | 1205 |
TABLE 7
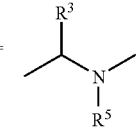
| Ex. | Y | MS |
|---|---|---|
| 22 | 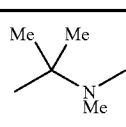 | 1190.8 |
| 72 | 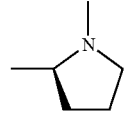 | 1188.6 |
TABLE 8
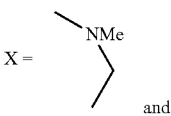
| Ex. | R³ | MS |
|---|---|---|
| 55 | 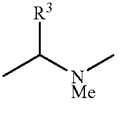 | 1318 |
| 61 | 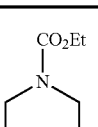 | 1219 |
| 66 | 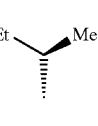 | 1247 |
TABLE 9
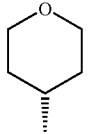
| Ex. | Rᵃ | R² | MS |
|---|---|---|---|
| 56 | EtHN(O)C— | H | 1277.2 |
| 58 | 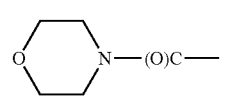 |  | 1297 |
| 67 | Et |  | 1235 |
| 68 | MeO(CH₂)₂— |  | 1264.6 |
| 70 | Me₂N(O)C— |  | 1277.7 |
| 77 | 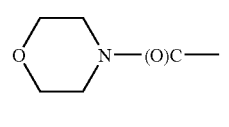 | Me | 1333.70 |
| 78 | Me₂N(O)C— |  | 1291.66 |
| 79 | EtHN(O)C— |  | 1291.66 |
| 80 | 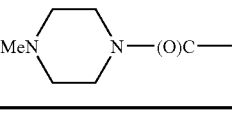 |  | 1346.73 |

TABLE 10

Y = (iBu)(Me)CH-N(Me)- [structure shown]

| Ex. | X | MS |
|---|---|---|
| 38 | (S)-2-methyl-N-methylpyrrolidinyl | 1244.7 |
| 40 | (R)-2-methyl-N-methylpyrrolidinyl | 1244.7 |
| 48 | N-methyl-tetrahydroisoquinolinyl (3-methyl) | 1306.8 |

TABLE 11

X = R¹R²N-CH(Me)- and Y = (iBu)(Me)CH-N(Me)-

| Ex. | R¹ | R² | MS |
|---|---|---|---|
| 36 | Me | ••••ιιιiBu | 1274.4 |
| 37 |  | ◂Bn | 1308.5 |
| 41 |  | ••••ιιι CH(Me)Et | 1274.5 |
| 42 |  | ••••ιιι(CH₂)₄NMeCO₂Bn | 1437.6 |
| 47 |  | ◂iBu | 1274.8 |
| 51 |  | ••••ιιιCH₂OBn | 1340.8 |
| 74 |  | ••••ιιιMe | 1232.5 |
| 75 |  | ••••ιιιCH₂OH | 1250.7 |
| 39 | H | ••••ιιι(CH₂)₄NHCO₂Bn | 1409.3 |
| 43 |  | ◂(CH₂)₄NHBoc | 1376.1 |
| 44 |  | ••••ιιιiBu | 1261.9 |

TABLE 11-continued

X = R¹R²N-CH(Me)- and Y = (iBu)(Me)CH-N(Me)-

| Ex. | R¹ | R² | MS |
|---|---|---|---|
| 45 |  | ◂iBu | 1260.7 |
| 46 |  | ••••ιιιCH₂OBn | 1324.6 |
| 49 |  | ◂Ph | 1280.7 |
| 50 | Et | H | 1232.7 |

TABLE 12

Example Compounds represented by following formula

[Macrocyclic peptide structure with Rᵃ-O group]

| Ex. | Rᵃ | MS |
|---|---|---|
| 81 | Me | 1237.48 |
| 82 | tBu | 1278.99 |
| 83 | H | 1223.53 |

Table 13~22 Preparation Compounds represented by following formula Type 1

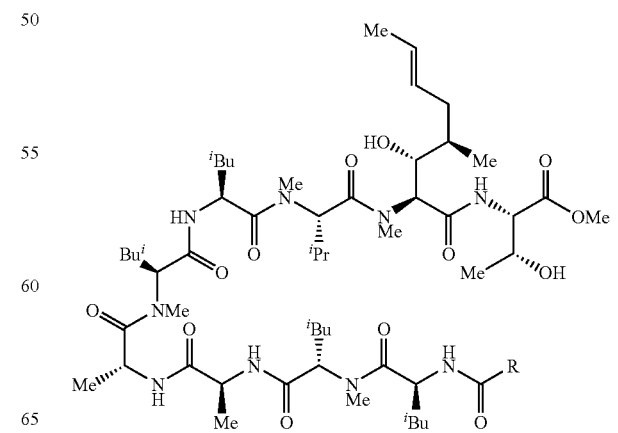

TABLE 13

(Type 1 - 1)

R = [structure with R³, R⁴, NHMe]

| Prep. | R³ | R⁴ | MS |
|---|---|---|---|
| 1 | iBu | H | 1179.6 |
| 4 | Et / Me | | 1179.7 |
| 5 | MeO / Me | | 1181 |
| 10 | iBu | | 1179 |
| 13 | iPr | | 1165 |
| 14 | Cy·Hex. | | 1206 |
| 15 | EtO / Me | | 1195 |
| 16 | Ph | | 1199.6 |
| 57 | ButO / Me | | 1224 |
| 58 | Me / OBn | | 1257.7 |
| 6 | Me | Me | 1151 |

TABLE 14

(Type 1 - 2)

R = [structure with R³, NMe, C=O, NMeFmoc, R²]

| Prep. | R² | R³ | MS |
|---|---|---|---|
| 25 | Me | Et / Me | 1486.9 |
| 33 | iBu | | 1529 |
| 34 | —CH₂OtBu | | 1559 |
| 26 | Me | MeO / Me | 1488 |
| 28 | —CH₂NMeBoc | | 1618 |
| 31 | Et | | 1502 |
| 38 | Bn | | 1565 |

TABLE 14-continued (Type 1 - 2)

R = [structure with R³, NMe, C=O, NMeFmoc, R²]

| Prep. | R² | R³ | MS |
|---|---|---|---|
| 27 | Me | iBu | 1487 |
| 32 | H | | 1472 |
| 35 | —CH₂-Cy.Hex. | | 1569 |
| 36 | Me | iPr | 1472 |
| 37 | | EtO / Me | 1502 |
| 159 | | iBu | 1486.9 |
| 211 | | Me / OBn | 1564.4 |
| 212 | | Cy·Hex. | 1513 |
| 39 | Me | Ph | 1506.7 |
| 40 | iBu | | 1548.5 |
| 208 | Me | ButO / Me | 1531 |
| 209 | iPr | | 1560 |
| 210 | Et | | 1560 |

TABLE 15

(Type 1 - 3)

R = [structure with R³, R⁴, NMe, C=O, R¹, NFmoc, R²]

| Prep. | R¹ | R² | R³ | R⁴ | MS |
|---|---|---|---|---|---|
| 29 | Me | iBu | Cy.Hex. | H | 1555.1 |
| 30 | H | Me | Me | | 1444 |
| 160 | H | —(CH₂)₄NHBoc | iBu | H | 1630 |

TABLE 16

(Type 1 - 4)

R = [structure with R³, R², Rᵇ, Me, N, O, NH]

| Prep. | Rᵇ | R² | R³ | MS |
|---|---|---|---|---|
| 117 | Me | H | ⁱBu | 1250.7 |
| 128 | | Et | Et⋯Me | 1278.7 |
| 129 | | ⁿBu | | 1306.5 |
| 130 | | —(CH₂)₃NMeCO₂Bn | | 1455.7 |
| 132 | | —(CH₂)₄NMeCO₂Bn | | 1470 |
| 135 | | —CH₂OC(O)NMe₂ | | 1351 |
| 136 | | —CH₂OMe | | 1294 |
| 131 | | —CH₂OMe | MeO⋯Me | 1296 |
| 133 | | —CH₂OC(O)NMe₂ | | 1253 |
| 137 | | —CH₂OBn | | 1372.8 |
| 134 | | —CH₂OMe | Ph | 1314.5 |
| 193 | Me | ⁱBu | ⁱBu | 1306.8 |
| 200 | H | | | 1292 |
| 197 | H | —CH₂OBn | | 1356.8 |
| 203 | Me | | | 1370.8 |
| 199 | Me | —(CH₂)₄NMeCO₂Bn | | 1469.9 |
| 202 | H | —(CH₂)₄NHCO₂Bn | | 1441.9 |
| 207 | Et | H | | 1264.7 |

TABLE 17

(Type 1 - 5)

R = [structure with ⁱBu, Me, N, O, Rᶜ, Rᵈ, R²]

| Prep. | Rᶜ | Rᵈ | R² | MS |
|---|---|---|---|---|
| 158 | Me | —C(O)NHPh | H | 1385.6 |
| 194 | Me | H | Bn | 1340.8 |
| 198 | Me | | Et⋯Me | 1306 |
| 201 | H | | ⁱBu | 1292 |
| 204 | Me | | | 1306.8 |
| 206 | H | | Ph | 1312.7 |

TABLE 18

(Type 1 - 6)

R = [structure with R³, R⁴, Me, N, Rᵉ]

| Prep. | Rᵉ | R³ | R⁴ | MS |
|---|---|---|---|---|
| 2 | —C(S)NHPh | ⁱBu | H | 1314.5 |
| 59 | Boc | Et⋯Me | | 1279.6 |
| 60 | | Ph | | 1299.4 |
| 61 | | MeO⋯Me | | 1281 |
| 62 | | EtO⋯Me | | 1295 |
| 65 | | ⁱBu | | 1279 |
| 66 | | ⁱPr | | 1265 |
| 67 | | Cy·Hex. | | 1306 |
| 63 | | Me | Me | 1251 |
| 93 | Fmoc | Buᵗ O⋯Me | H | 1446 |
| 94 | | Me⋯OBn | | 1479.9 |

TABLE 19

(Type 1 - 7)

R = [structure with R³, O, R¹, N, NBoc, R⁵, R²]

| Prep. | R¹ | R² | R³ | R⁵ | MS |
|---|---|---|---|---|---|
| 64 | Me | Et | Buᵗ O⋯Me | Me | 1439 |

TABLE 19-continued (Type 1 - 7)

R = [structure with R³, R¹, NBoc, R⁵, R²]

| Prep. | R¹ | R² | R³ | R⁵ | MS |
|---|---|---|---|---|---|
| 118 | | Et | Et,,,,Me | | 1379.5 |
| 119 | | —(CH₂)₄NMeCO₂Bn | | | 1570 |
| 121 | | —(CH₂)₃NMeCO₂Bn | | | 1556.6 |
| 123 | | ⁿBu | | | 1406.7 |
| 124 | | —CH₂OMe | | | 1394 |
| 125 | | —CH₂OC(O)NMe₂ | | | 1451 |
| 120 | | —CH₂OMe | MeO,,,,Me | | 1396 |
| 126 | | —CH₂OC(O)NMe₂ | | | 1453 |
| 127 | | —CH₂OBn | | | 1472.8 |
| 122 | | —CH₂OMe | Ph | | 1414.1 |
| 91 | | Me | Et,,,,Me | Et | 1379 |
| 92 | | | ⁱPr | | 1365 |
| 179 | H | —CH₂OBn | ⁱBu | Me | 1456.9 |
| 192 | Me | | | | 1470.9 |
| 178 | Me | ⁱBu | | | 1406.9 |
| 185 | H | | | | 1392 |
| 182 | H | —(CH₂)₄NHCO₂Bn | | | 1542 |
| 184 | Me | —(CH₂)₄NMeCO₂Bn | | | 1570.0 |
| 191 | Et | H | | | 1364.8 |

TABLE 20

(Type 1 - 8)

R = [structure with ⁱBu, N-Me, R¹, NBoc, R²]

| Prep. | R¹ | R² | MS |
|---|---|---|---|
| 186 | H | ⁱBu | 1392 |
| 188 | Me | ⁱBu | 1406.9 |
| 180 | Me | Et,,,Me | 1406.9 |
| 187 | Me | Bn | 1440.9 |
| 190 | H | Ph | 1412.8 |

TABLE 21

(Type 1 - 9)

R = [structure with ⁱBu, N-Me, Y]

| Prep. | Y | MS |
|---|---|---|
| 181 | Boc-N-pyrrolidine-2-yl-methyl | 1376.7 |
| 183 | Boc-N-pyrrolidine-2-yl-methyl | 1377.6 |
| 189 | Boc-N-tetrahydroisoquinoline-3-methyl | 1438.9 |
| 195 | HN-pyrrolidine-2-yl-methyl | 1276.8 |
| 196 | HN-pyrrolidine-2-yl-methyl | 1277.1 |
| 205 | HN-tetrahydroisoquinoline-3-methyl | 1324.7 |

TABLE 22

(Type 1 - 10)

R = [structure with ⁱBu, N-Me, Gly, N-Me, threonine with Rᶠ]

| Prep. | Rᶠ | MS |
|---|---|---|
| 154 | —C(S)NHPh | 1486.5 |
| 155 | H | 1351.6 |
| 157 | Boc | 1451.6 |

Table 23~31: Preparation Compounds represented by following formula Type 2
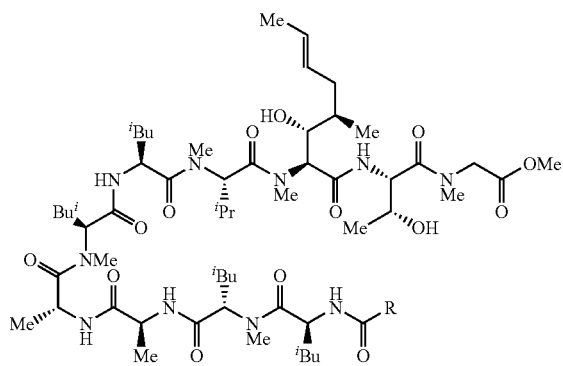
TABLE 23
(Type 2 - 1)
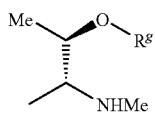
| Prep. | R$^g$ | MS |
|---|---|---|
| 7 | —C(O)-morpholino | 1351 |
| 8 | —C(O)NMe$_2$ | 1309 |
| 11 | —C(O)NHEt | 1309 |
| 12 | Me | 1252 |
| 17 | —(CH$_2$)$_2$OMe | 1296 |
| 18 | H | 1238.6 |
TABLE 24
(Type 2 - 2)
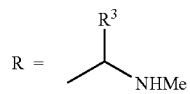
| Prep. | R$^3$ | MS |
|---|---|---|
| 9 | CH$_2$NMeCO$_2$Bn | 1385 |
| 138 | $^i$Bu | 1251 |
| 153 | Et, Me | 1251 |
TABLE 25
(Type 2 - 3)
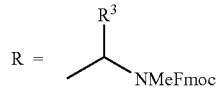
| Prep. | R$^3$ | MS |
|---|---|---|
| 95 | Bu$^t$O, Me | 1517 |
| 97 | N-piperidyl-CO$_2$Et (4-Me) | 1501 |
| 102 | Bu$^t$O | 1503 |
| 103 | 4-Me-tetrahydropyran | 1501 |
| 109 | BnO, Me | 1551 |
TABLE 26
(Type 2 - 4)
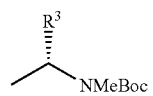
| Prep. | R$^3$ | MS |
|---|---|---|
| 96 | —(CH$_2$)$_2$NMeCO$_2$Bn | 1485 |
| 98 | Bn | 1385 |
| 105 | —CH$_2$-Cy.Hex. | 1391 |
| 108 | Ph | 1371 |
| 111 | Cy.Hex. | 1377 |

TABLE 27
(Type 2 - 5)
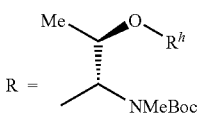
| Prep. | $R^h$ | MS |
|---|---|---|
| 99 | —(CH$_2$)$_2$OMe | 1396 |
| 101 | —C(O)—N(morpholine) | 1451 |
| 107 | Me | 1352 |
| 112 | —C(O)NHEt | 1409 |
| 113 | —C(O)NMe$_2$ | 1409 |
| 116 | H | 1338.7 |
TABLE 28
(Type 2-6)
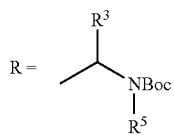
| Prep. | $R^3$ | $R^5$ | MS |
|---|---|---|---|
| 104 | Et—CH—Me | Me | 1351 |
| 106 | Et—CH—Me | | 1351 |
| 114 | EtO—CH—Me | | 1367 |
| 100 | Et—CH—Me | H | 1336 |
TABLE 29
(Type 2-7)
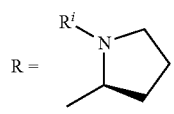
| Prep. | $R^i$ | MS |
|---|---|---|
| 19 | H | 1220.6 |
| 115 | Boc | 1320.7 |
TABLE 30
(Type 2-8)
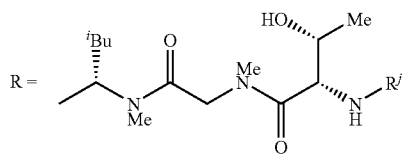
| Prep. | $R^j$ | MS |
|---|---|---|
| 90 | Boc | 1545 |
| 152 | H | 1423 |
TABLE 31
(Type 2-9)
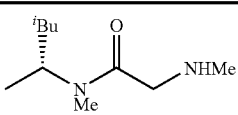
| Prep. | R | MS |
|---|---|---|
| 168 | (shown) | 1322 |
Table 32~36: Preparation Compounds represented by following formula Type 3
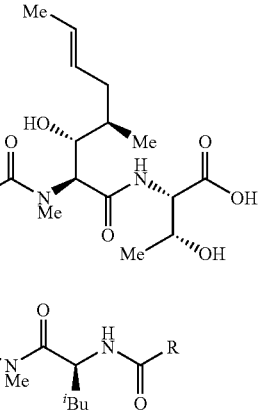
TABLE 32
(Type 3-1)
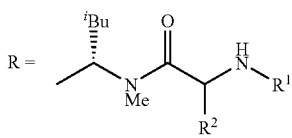
| Prep. | $R^1$ | $R^2$ | $R^3$ | MS |
|---|---|---|---|---|
| 55 | Me | | Cy. Hex. | 1318.9 |
| 79 | H | | $^i$Bu | 1278 |
| 86 | Me | $^i$Bu | | 1292.7 |
| 76 | | Bn | | 1326.7 |

TABLE 32-continued (Type 3-1)

R = [structure with iBu, Me, N, NHR¹, R²]

| Prep. | R¹ | R² | R³ | MS |
|-------|-----|------|-----|------|
| 84 | | Et⋯Me (stereo) | | 1292 |
| 85 | H | CH(Ph)— | | 1298.7 |
| 214 | | (CH₂)₄NHBoc | | 1393 |

TABLE 33

(Type 3-2)

R = [structure with R³, R⁴, R⁵, N, NHR¹, R²]

| Prep. | R¹ | R² | R³ | R⁴ | R⁵ | MS |
|-------|-----|-----------------|-----|-----|-----|------|
| 43 | Me | H | Me | Me | Me | 1208 |
| 77 | H | —(CH₂)₄NHCO₂Bn | iBu | | H | 1427.9 |
| 81 | | —CH₂OBn | iBu | | | 1342.7 |
| 83 | | iBu | | | | 1278 |
| 88 | Et | H | | | | 1250.7 |
| 150 | Me | Me | Et⋯Me | H | Et | 1265 |
| 151 | | iPr | | | | Negative (ESI⁻): 1249 [M − H] |

TABLE 34

(Type 3-3)

R = [structure with R³, N(Me), NHMe, R²]

| Prep. | R² | R³ | MS |
|-------|------------|-------|--------|
| 22 | Me | Cy. Hex. | 1277 |
| 44 | H | tBu | 1236 |
| 46 | Me | | 1250 |
| 47 | —CH₂-Cy. Hex. | | 1332 |
| 48 | Me | iPr | 1236 |
| 53 | Me | Ph | 1270.6 |
| 54 | iBu | | 1313.1 |
| 144 | CH₂OMe | | 1300.8 |

TABLE 34-continued (Type 3-3)

R = [structure with R³, N(Me), NHMe, R²]

| Prep. | R² | R³ | MS |
|-------|------------|-------|--------|
| 75 | iBu | iBu | 1292.7 |
| 80 | —(CH₂)₄NMeCO₂Bn | | 1455.9 |
| 89 | —CH₂OBn | | 1356.8 |
| 213 | Me | | 1250.7 |

TABLE 35

(Type 3-4)

R = [structure with R³, N(Me), NHMe, R²]

| Prep. | R² | R³ | MS |
|-------|------------------|-------------|--------|
| 20 | Me | BuʳO⋯Me | 1295 |
| 21 | Et | | 1309 |
| 24 | iPr | | 1323 |
| 23 | Me | Me⋯OBn | 1328.9 |
| 41 | Me | Et⋯Me | 1232.7 |
| 45 | —CH₂OtBu | | 1322 |
| 56 | iBu | | 1292 |
| 139 | Et | | 1264.7 |
| 140 | —CH₂OC(O)NMe₂ | | 1337 |
| 141 | —(CH₂)₃NMeCO₂Bn | | 1442.1 |
| 145 | nBu | | 1292.5 |
| 146 | —CH₂OMe | | 1280 |
| 147 | —(CH₂)₄NMeCO₂Bn | | 1455 |
| 42 | Bn | MeO⋯Me | 1328 |
| 49 | Et | | 1266 |
| 50 | Me | | 1252 |
| 52 | —CH₂NMeBoc | | 1381 |
| 142 | —CH₂OC(O)NMe₂ | | 1339 |
| 143 | —CH₂OMe | | 1282 |
| 148 | —CH₂OBn | | 1358.7 |
| 51 | Me | EtO⋯Me | 1266 |
| 149 | Et | HO⋯Me | 1253 |

TABLE 36

(Type 3-5)

R = 
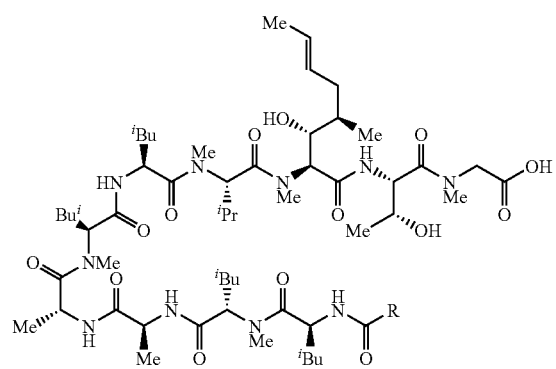

| Prep. | X | MS |
|---|---|---|
| 78 | (2-methylpyrrolidine) | 1262.5 |
| 82 | (2-methylpyrrolidine) | 1262.5 |
| 87 | (3-methyl-1,2,3,4-tetrahydroisoquinoline) | 1324.7 |

Table 37~40: Preparation Compounds represented by following formula Type 4

TABLE 37

(Type 4-1)

R = CH(R³)—NHMe (with Me)

| Prep. | R³ | MS |
|---|---|---|
| 69 | Bn | 1272 |
| 71 | Ph | 1257 |
| 72 | Cy. Hex. | 1263 |
| 73 | —CH₂-Cy. Hex. | 1277 |
| 163 | —CH₂OʳBu | 1267 |
| 170 | —(CH₂)₂NMeCO₂Bn | 1371 |

TABLE 38

(type 4-2)

R = CH(Me)CH(Me)(OR^k)(NHMe)

| Prep. | R^k | MS |
|---|---|---|
| 171 | —C(O)—N(morpholine) | 1337 |
| 172 | Me | 1238 |
| 173 | —C(O)NMe₂ | 1295 |
| 174 | —C(O)NHEt | 1295 |
| 175 | —(CH₂)₂OMe | 1282 |
| 176 | H | 1224.6 |

TABLE 39

(Type 4-3)

R = CH(R³)(NHR⁵) with Me

| Prep. | R³ | R⁵ | MS |
|---|---|---|---|
| 68 | Et,,,, | Me | H | 1223 |
| 70 | Et,,,, | Me | Me | 1237 |
| 74 | EtO,,,, | Me |  | 1253 |
| 161 | Buⁱ O,,,, | Me |  | 1281 |
| 162 | BnO,,,, | Me |  | 1315 |
| 164 | (tetrahydropyran-4-yl) |  |  | 1265 |
| 165 | (N-CO₂Et piperidin-4-yl) |  |  | 1336 |
| 169 | Et,,,, | Me |  | 1237 |

TABLE 40
(Type 4-4)
| Prep. | R | MS |
|---|---|---|
| 177 |  | 1206.6 |
TABLE 41
Preparation Compounds of the Other Type represented by following formula
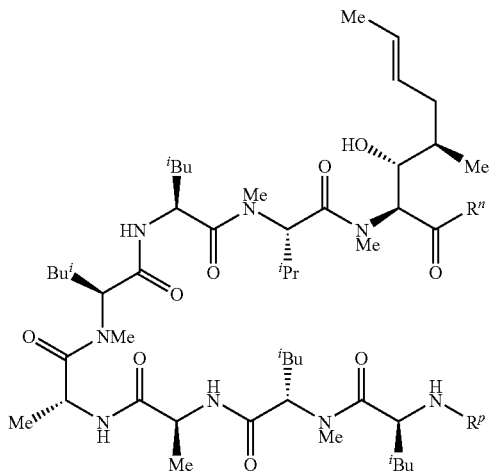
| Prep. | $R^n$ | $R^p$ | MS |
|---|---|---|---|
| 3 | 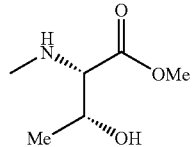 | H | 1052.6 |
| 166 | 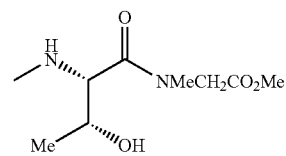 |  | 1123 |
| 167 | OH | 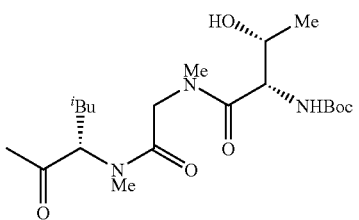 | 1336.6 |

TABLE 41-continued

Preparation Compounds of the Other Type represented by following formula

| Prep. | $R^n$ | $R^p$ | MS |
|---|---|---|---|
| 156 | (structure with OMe, Me, NHBoc, iBu, NMe, O) | | 1818.7 |

TABLE 42

Preparation Compounds of the Another Type represented by following formula

| Prep. | $R^a$ | MS |
|---|---|---|
| 110 | $Bu^t-$ | 1318.73 |
| 215 | HO— | 1262.73 |
| 216 | $O_2N$—C$_6$H$_4$—O(O)C— | 1427.72 |

TABLE 42-continued

Preparation Compounds of the Another Type represented by following formula

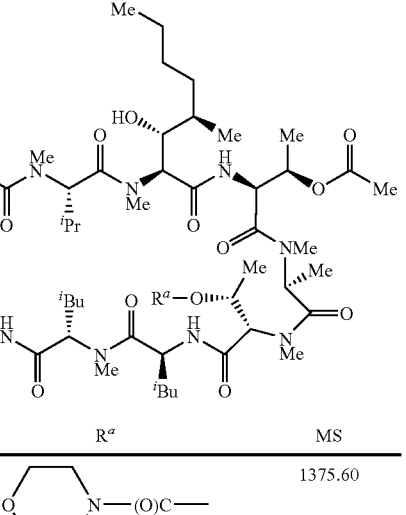

| Prep. | $R^a$ | MS |
|---|---|---|
| 217 | (morpholine)N—(O)C— | 1375.60 |
| 218 | Me₂N(O)C— | 1330.70 |
| 219 | EtHN(O)C— | 1375.77 |
| 220 | MeN(piperazine)N—(O)C— | 1430.73 |

TABLE 43

| Ex. | NMR Data |
|---|---|
| 1 | 9.10 (1H, brd, J = 9 Hz), 7.60 (1H, brd, J = 9 Hz), 7.20 (1H, d, J = 9 Hz), 7.0 (1H, d, J = 8 Hz), 6.58 (1H, d, J = 9 Hz), 5.67 (1H, d, J = 3 Hz), 5.6-5.4 (3H, m), 5.35-5.25 (2H, m), 5.12 (1H, m), 4.85-4.77 (2H, m), 4.75-7.60 (3H, m), 4.65-4.52 (2H, m), 4.31-4.10 (3H, m), 4.0-3.8 (2H, m), 3.72 (1H, brs), 3.45 (3H, s), 3.39 (3H, s), 3.20 (6H, s), 3.13 (6H, s), 3.10 (3H, s), 3.02 (3H, s), 2.51 (1H, brd, J = 5 Hz), 2.4-2.3 (2H, m), 2.2-1.9 (4H, m), 1.9-1.1 (10H, m), 1.66 (3H, d, J = 6 Hz), 1.40 (3H, d, J = 7.5 Hz), 1.13 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) (for a major conformer) |
| 2 | 8.30 (1H, d, J = 8.5 Hz), 7.80 (1H, d, J = 9.0 Hz), 6.95 (1H, d, J = 9.0 Hz), 6.68 (1H, d, J = 9.5 Hz), 6.57 (1H, d, J = 9.5 Hz), 5.65 (1H, d, J = 3.0 Hz), 5.37-5.56 (3H, m), 5.30 (1H, m), 5.13 (1H, m), 4.97 (2H, m), 4.86 (2H, m), 4.70 (2H, m), 4.53 (1H, m), 4.22 (1H, m), 3.99 (1H, m), 3.42 (1H, s), 3.13 (3H, s), 3.42 (3H, s), 3.05 (3H, s), 2.99 (3H, s), 2.97 (3H, s), 2.93 (3H, s), 2.57 (1H, d, J = 4.5 Hz), 2.33 (2H, m), 2.15-0.75 (64H, m), 1.65 (3H, d, J = 6.0 Hz), 1.32 (3H, d, J = 6.0 Hz), 0.75 (3H, d, J = 6.5 Hz) |
| 3 | 8.35 (1H, d, J = 8.5 Hz), 7.78 (1H, d, J = 8.8 Hz), 6.95 (1H, d, J = 8.9 Hz), 6.88 (1H, d, J = 8.1 Hz), 6.57 (1H, d, J = 8.9 Hz), 5.64 (1H, d, J = 3 Hz), 5.38-5.52 (3H, m), 5.30 (1H, m), 5.13 (1H, m), 4.95 (2H, m), 4.87 (2H, m), 4.70 (2H, m), 4.53 (1H, m), 4.23 (1H, m), 3.95 (1H, m), 3.41 (1H, s), 3.13 (3H, s), 3.11 (3H, s), 3.05 (3H, s), 2.99 (3H, s), 2.97 (3H, s), 2.93 (3H, s), 2.56 (1H, d, J = 5.5 Hz), 2.34 (2H, m), 0.75-2.15 (68H, m), 1.66 (3H, d, J = 6.0 Hz), 1.32 (3H, d, J = 6.5 Hz), 0.75 (3H, d, J = 6.5 Hz) |
| 4 | 8.14 (1H, d, J = 8.5 Hz), 7.70 (1H, d, J = 8.5 Hz), 7.34 (5H, m), 6.94 (1H, d, J = 8.5 Hz), 6.89 (1H, d, J = 8.5 Hz), 6.53 (1H, d, J = 8.5 Hz), 5.62 (1H, d, J = 2.5 Hz), 5.41 (3H, m), 5.26 (1H, m), 5.11 (2H, s), 5.11 (1H, m), 4.91 (2H, m), 4.86 (2H, m), 4.69 (2H, m), 4.52 (1H, m), 4.22 (1H, m), 3.97 (1H, m), 3.45 (1H, s), 3.20-3.41 (2H, m), 3.12 (3H, s), 3.09 (3H, s), 3.04 (3H, s), 3.02 (3H, s), 2.93 (3H, s), 2.91 (3H, s), 2.88 (3H, s), 2.70 (1H, s), 2.35 (2H, m), 0.75-21.15 (63H, m), 1.66 (3H, d, J = 6.0 Hz), 1.32 (3H, d, J = 6.5 Hz), 0.75 (3H, d, J = 6.5 Hz) |
| 5 | 9.24 (0.5H, d, J = 9.0 Hz), 8.89 (0.5H, d, J = 9.0 Hz), 8.33 (0.5H, d, J = 9.0 Hz), 7.55 (0.5H, d, J = 9.0 Hz), 7.06-7.42 (5H, m), 7.17 (1H, d, J = 9.0 Hz), 7.05 (0.5H, d, J = 9.0 Hz), 6.98 (0.5H, d, J = 9.0 Hz), 6.87 (1H, d, J = 9.0 Hz), 6.42 (0.5H, s), 6.14 (0.5H, s), 5.67 (1H, s), 5.29-5.49 (3H, m), 5.06 (1H, m), 4.89 (3H, m), 4.71 (1H, m), 4.57 (1H, m), 4.28 (2H, m), 3.48-3.81 (3H, m), 3.36 (1.5H, s), 3.33 (1.5H, s), 3.23 (1.5H, s), 3.20 (1.5H, s), 3.13 (3H, s), 3.08 (3H, s), 2.98 (1.5H, s), 2.96 (1.5H, s), 2.94 (1.5H, s), 2.90 (1.5H, s), 2.75 (1.5H, s), 2.69 (1.5H, s), 2.62 (0.5H, d, J = 5.5 Hz), 2.52 (0.5H, d, J = 5.5 Hz), 2.36 (2H, m), 0.60-2.10 (61H, m) |
| 6 | 8.20 (1H, brd, J = 9 Hz), 7.70 (1H, brd, J = 9 Hz), 6.95 (1H, d, J = 9 Hz), 6.86 (1H, d, J = 8 Hz), 6.55 (1H, d, J = 9 Hz), 5.67 (1H, d, J = 3 Hz), 5.6-5.4 (2H, m), 5.35-5.25 (2H, m), 5.12 (1H, dd, J = 10 and 4 Hz), 5.0-4.75 (5H, m), 4.75-4.65 (2H, m), 4.65-4.55 (2H, m), 4.31-4.10 (3H, m), 3.72 (1H, brs), 3.17 (3H, s), 3.12 (6H, s), 3.08 (3H, s), 3.05 (3H, s), 2.93 (6H, s), 2.89 (3H, s), 2.85 (3H, s), 2.55 (1H, brd, J = 5 Hz), 2.4-2.3 (2H, m), 2.2-1.9 (4H, m), 1.9-1.1 (10H, m), 1.66 (3H, d, J = 6 Hz), 1.35 (3H, d, J = 7.5 Hz), 1.13 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) (for a major conformer) |
| 7 | 7.75 (1H, brd, J = 9 Hz), 7.55 (1H, brd, J = 9 Hz), 6.95 (1H, d, J = 9 Hz), 6.80-6.70 (5H, m), 6.86 (1H, d, J = 8 Hz), 6.62 (1H, d, J = 9 Hz), 5.67 (1H, d, J = 3 Hz), 5.6-5.4 (2H, m), 5.30-5.25 (2H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.23 (1H, m), 4.21 (1H, m), 3.88 (1H, brs), 3.50-3.41 (3H, m), 3.17 (3H, s), 3.13 (3H, s), 3.05 (3H, s), 3.02 (3H, s), 2.98 (3H, s), 2.96 (3H, s), 2.90 (3H, s), 2.38 (1H, brd, J = 5 Hz), 2.4-2.3 (2H, m), 2.2-1.9 (5H, m), 1.9-0.80 (51H, m), 1.62 (3H, d, J = 6 Hz), 1.33 (3H, d, J = 6 Hz), 1.13 (3H, d, J = 6.5 Hz), 1.09 (3H, d, J = 6 Hz), 0.74 (3H, d, J = 7 Hz) (for a major conformer) |
| 8 | 8.98 (1H, brd, J = 9 Hz), 7.58 (1H, brd, J = 9 Hz), 6.95 (1H, d, J = 9 Hz), 6.80 (1H, d, J = 8 Hz), 6.72 (1H, d, J = 9 Hz), 5.67 (1H, d, J = 3 Hz), 5.6-5.4 (3H, m), 5.31 (1H, dd, J = 12 and 4 Hz), 5.12 (1H, dd, J = 10 and 4 Hz), 5.0-4.8 (4H, m), 4.75-4.55 (3H, m), 4.45-4.40 (1H, m), 4.38-4.25 (2H, m), 4.25-4.05 (1H, m), 3.73 (1H, brs), 3.39 (3H, s), 3.30 (3H, s), 3.18 (3H, s), 3.14 (3H, s), 3.06 (3H, s), 2.90 (6H, s), 2.85 (3H, s), 2.51 (1H, brd, J = 5 Hz), 2.4-2.3 (2H, m), 2.2-1.9 (5H, m), 1.9-1.1 (11H, m), 1.64 (3H, d, J = 6 Hz), 1.36 (3H, d, J = 7.5 Hz), 1.31 (3H, d, J = 6 Hz), 1.13 (3H, d, J = 6.5 Hz), 1.09 (3H, d, J = 7 Hz), 1.10-0.70 (34H, m), 0.74 (3H, d, J = 7 Hz) (for a major conformer) |
| 9 | 9.10 (1H, brd, J = 9 Hz), 7.60 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (2H, m), 5.4-5.2 (2H, m), 5.10-5.0 (2H, m), 5.0-4.60 (5H, m), 4.65-4.55 (1H, m), 4.31-4.10 (2H, m), 4.05-3.98 (1H, m), 3.85-3.50 (2H, m), 3.72 (1H, brs), 3.38 (3H, s), 3.33 (3H, s), 3.28 (3H, s), 3.20 (3H, s), 3.19 (3H, s), 3.05 (6H, s), 2.90 (3H, s), 2.54 (1H, brd, J = 5 Hz), 2.4-2.3 (2H, m), 2.2-1.9 (4H, m), 1.9-1.1 (10H, m), 1.66 (3H, d, J = 6 Hz), 1.35 (3H, d, J = 6 Hz), 1.13 (3H, d, J = 6.5 Hz), 0.97 (3H, d, J = 7 Hz), 0.90 (3H, d, J = 6 Hz), 1.0-0.8 (30H, m), 0.74 (3H, d, J = 7 Hz) (for a major conformer) |

TABLE 43-continued

| Ex. | NMR Data |
|---|---|
| 10 | 8.45 (1H, brd, J = 9 Hz), 7.78 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (3H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.27 (1H, m), 4.21 (1H, m), 3.88 (1H, brs), 3.75-3.70 (1H, m), 3.65-3.60 (1H, m), 3.37 (3H, s), 3.14 (3H, s), 3.12 (3H, s), 3.05 (3H, s), 3.02 (3H, s), 2.92 (3H, s), 2.92 (3H, s), 2.51 (1H, brd, J = 5 Hz), 2.4-2.3 (2H, m), 2.2-1.9 (5H, m), 1.9-1.1 (11H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.0-0.8 (34H, m), 0.74 (3H, d, J = 7 Hz) (for a major conformer) |
| 12 | 8.71 (1H, d, J = 9 Hz), 7.67 (1H, d, J = 9 Hz), 6.97 (1H, d, J = 9 Hz), 6.92 (1H, d, J = 8 Hz), 6.86 (1H, d, J = 7 Hz), 5.66 (1H, d, J = 3 Hz), 5.56-4.78 (11H, m), 4.32-4.15 (3H, m), 3.69 (1H, brs), 3.28 (3H, s), 3.19 (3H, s), 3.08 (3H, s), 3.06 (6H, s), 2.99 (1H, d, J = 5 Hz), 2.91 (3H, s), 2.51 (1H, brd, J = 6 Hz), 2.45-2.25 (2H, m), 2.20-1.50 (11H, m), 1.66 (3H, d, J = 6 Hz), 1.48-1.16 (9H, m), 1.45 (3H, d, J = 6 Hz), 1.14 (3H, d, J = 6 Hz), 1.10 (3H, d, J = 6 Hz), 1.05-0.80 (26H, m), 0.82 (3H, d, J = 6 Hz), 0.72 (3H, d, J = 7 Hz) |
| 14 | 8.45 (1H, brd, J = 9 Hz), 7.78 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (3H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.27 (1H, m), 4.21 (1H, m), 3.88 (1H, brs), 3.13 (3H, s), 3.11 (3H, s), 3.05 (3H, s), 3.01 (3H, s), 2.98 (3H, s), 2.92 (3H, s), 2.51 (1H, brd, J = 5 Hz), 2.4-2.3 (2H, m), 2.2-1.9 (5H, m), 1.9-1.1 (11H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.09 (3H, d, J = 6 Hz), 1.0-0.8 (34H, m), 0.74 (3H, d, J = 7 Hz) (for a major conformer) |
| 15 | 9.28 (1H, d, J = 8.5 Hz), 7.52 (1H, d, J = 8.0 Hz), 7.15-7.43 (5H, m), 7.12 (1H, d, J = 9.0 Hz), 6.97 (1H, d, J = 8.5 Hz), 6.86 (1H, d, J = 8.0 Hz), 6.42 (1H, s), 5.69 (1H, d, J = 2.5 Hz), 5.21-5.57 (4H, m), 5.08 (1H, m), 4.88 (4H, m), 4.72 (1H, m), 4.56 (1H, m), 4.27 (2H, m), 3.70 (1H, m), 3.24 (3H, s), 3.13 (3H, s), 3.09 (3H, s), 3.07 (3H, s), 2.92 (3H, s), 2.73 (3H, s), 2.52 (1H, d, J = 5.0 Hz), 2.36 (2H, m), 0.68-2.04 (62H, m) |
| 16 | 9.10 (1H, brd, J = 9 Hz), 7.60 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (2H, m), 5.35-5.25 (2H, m), 5.12 (1H, dd, J = 10 and 4 Hz), 5.0-4.8 (3H, m), 4.75-4.65 (2H, m), 4.73 (1H, m), 4.53 (1H, m), 4.31-4.10 (3H, m), 3.72 (1H, brs), 3.31 (3H, s), 3.22 (3H, s), 3.18 (3H, s), 3.06 (6H, s), 3.02 (3H, s), 2.90 (3H, s), 2.19 (1H, brd, J = 5 Hz), 2.4-2.3 (2H, m), 2.2-1.9 (4H, m), 1.9-1.1 (12H, m), 1.66 (3H, d, J = 6 Hz), 1.40 (3H, d, J = 6 Hz), 1.13 (3H, d, J = 6.5 Hz), 1.09 (3H, d, J = 7 Hz), 1.09 (3H, d, J = 6 Hz), 1.0-0.8 (33H, m), 0.74 (3H, d, J = 7 Hz) (for a major conformer) |
| 17 | 8.95 (1H, brd, J = 9 Hz), 7.72 (1H, brd, J = 9 Hz), 6.95 (1H, d, J = 9 Hz), 6.93 (1H, d, J = 9 Hz), 6.55 (1H, d, J = 9 Hz), 5.67 (1H, d, J = 3 Hz), 5.6-5.35 (3H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.25 (1H, m), 4.22 (1H, m), 3.88 (1H, brs), 3.15 (3H, s), 3.12 (3H, s), 3.06 (3H, s), 3.03 (6H, s), 2.92 (3H, s), 2.48 (1H, brd, J = 5 Hz), 2.4-2.3 (2H, m), 2.2-0.8 (63H, m), 1.66 (3H, d, J = 6 Hz), 1.38 (3H, d, J = 7.5 Hz), 1.13 (3H, d, J = 6.5 Hz), 1.09 (3H, d, J = 7 Hz), 1.08 (3H, d, J = 6 Hz), 0.74 (3H, d, J = 7 Hz) |
| 18 | 9.10 (1H, brd, J = 9 Hz), 7.60 (1H, brd, J = 9 Hz), 7.20 (1H, d, J = 9 Hz), 7.00 (1H, d, J = 8 Hz), 6.62 (1H, d, J = 9 Hz), 5.67 (1H, d, J = 3 Hz), 5.6-5.4 (2H, m), 5.35-5.25 (2H, m), 5.12 (1H, dd, J = 10 and 4 Hz), 4.9-4.8 (5H m), 4.65-4.52 (2H, m), 4.31-4.10 (3H, m), 4.0-3.8 (2H, m), 3.72 (1H, brs), 3.55 (3H, s), 3.39 (3H, s), 3.24 (3H, s), 3.13 (6H, s), 3.10 (3H, s), 3.05 (3H, s), 2.99 (3H, s), 2.51 (1H, brd, J = 5 Hz), 2.4-2.3 (2H, m), 2.2-1.9 (4H, m), 1.9-1.1 (10H, m), 1.66 (3H, d, J = 6 Hz), 1.40 (3H, d, J = 7.5 Hz), 1.46 (9H, s), 1.13 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) (for a major conformer) |
| 19 | 9.20 (1H, d, J = 8.5 Hz), 7.65 (1H, d, J = 9.0 Hz), 7.07-7.40 (5H, m), 7.14, 6.49 (1H, brd, J = 7.0 Hz), 6.90 (1H, d, J = 9.0 Hz), 6.43 (1H, s), 5.66 (1H, d, J = 3.0 Hz), 5.30-5.50 (3H, m), 5.25 (1H, m), 5.10 (1H, m), 4.93 (2H, m), 4.84 (3H, m), 4.70 (1H, m), 4.54 (1H, m), 4.27 (1H, m), 4.27 (1H, m), 3.77 (1H, s), 3.21 (3H, s), 3.09 (3H, s), 3.06 (3H, s), 3.03 (3H, s), 2.91 (3H, s), 2.65 (3H, s), 2.51 (1H, d, J = 5.0 Hz), 2.36 (2H, m), 0.75-2.15 (65H, m), 0.75 (3H, d, J = 6.5 Hz) |
| 20 | 8.34 (1H, d, J = 8.5 Hz), 7.80 (1H, d, J = 8.5 Hz), 6.95 (1H, d, J = 8.5 Hz), 6.87 (1H, d, J = 8.0 Hz), 6.55 (1H, d, J = 8.5 Hz), 5.65 (1H, d, J = 3.0 Hz), 5.40-5.56 (3H, m), 5.31 (1H, m), 5.06 (3H, m), 4.87 (2H, m), 4.71 (2H, m), 4.52 (1H, m), 4.27 (1H, m), 3.96 (1H, s), 3.48 (1H, d, J = 5.0 Hz), 3.12 (3H, s), 3.11 (3H, s), 3.05 (3H, s), 2.99 (3H, s), 2.95 (3H, s), 2.93 (3H, s), 2.55 (1H, d), 2.34 (2H, m), 0.80-2.15 (67H, m), 1.66 (3H, d, J = 6.0 Hz), 1.32 (3H, d, J = 7.5 Hz), 0.80 (3H, d, J = 6.5 Hz), 0.74 (3H, d, J = 6.5 Hz) |
| 21 | 8.45 (1H, brd, J = 9 Hz), 7.78 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (3H, m), 5.31 (1H, dd, J = 12 and 4 Hz), 5.0-4.8 (5H, m), 4.75-4.65 (2H, m), 4.53 (1H, m), 4.27 (1H, m), 4.21 (1H, m), 3.88 (1H, brs), 3.13 (3H, s), 3.11 (3H, s), 3.05 (3H, s), 3.01 (3H, s), 2.98 (3H, s), 2.92 (3H, s), 2.51 (1H, brd, J = 5 Hz), 2.4-2.3 (2H, m), 2.2-1.9 (5H, m), 1.9-1.1 (14H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.0-0.8 (40H, m), 0.74 (3H, d, J = 7 Hz) (for a major conformer) |
| 22 | 8.06 (1H, d, J = 9 Hz), 7.75 (1H, d, J = 9 Hz), 7.08 (1H, d, J = 9 Hz), 7.06 (1H, d, J = 9 Hz), 6.71 (1H, d, J = 8 Hz), 5.53-5.41 (4H, m), 5.32-5.30 (1H, m), 5.18-5.12 (1H, m), 4.96-4.85 (3H, m), 4.72-4.68 (1H, m), 4.68-4.55 (2H, m), 4.22-4.12 (2H, m), 3.71 (1H, brd, J = 5 Hz), 3.38 (1H, m), 3.25 (3H, s), 3.16 (3H, s), 3.06 (3H, s), 3.25-2.93 (2H, m), 3.02 (3H, s), 3.00 (3H, s), 2.98 (3H, m), 2.45-2.26 (2H, m), 2.13-1.97 (4H, m), 1.86-1.62 (3H, m), 1.63 (3H, brd, J = 6 Hz), 1.57-1.0 (6H, m), 1.49 (3H, s), 1.48 (3H, s), 1.33 (3H, d, J = 7 Hz), 1.16 (3H, d, J = 7 Hz), 1.13 (3H, d, J = 6 Hz), 1.11 (3H, d, J = 6 Hz), 1.00 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 23 | 8.58 (1H, brd, J = 9 Hz), 7.78 (1H, brd, J = 9 Hz), 6.95 (1H, d, J = 9 Hz), 6.90 (1H, d, J = 8 Hz), 6.62 (1H, d, J = 9 Hz), 5.67 (1H, d, J = 3 Hz), 5.6-5.4 (3H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.25 (1H, m), 4.22 (1H, m), 4.0-3.8 (1H, m), 3.83 (1H, brs), 3.75-3.70 (1H, m), 3.65-3.60 (1H, m), 3.14 (3H, s), 3.12 (3H, s), 3.09 (3H, s), 3.06 (3H, s), 3.03 (3H, s), 2.92 (3H, s), 2.51 (1H, brd, J = 5 Hz), 2.4-2.3 (2H, m), 2.2-1.9 (5H, m), 1.9-1.1 (11H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.0-0.8 (42H, m), 0.74 (3H, d, J = 7 Hz) (for a major conformer) |
| 24 | 9.00 (1H, brd, J = 9 Hz), 7.72 (1H, brd, J = 9 Hz), 6.95 (1H, d, J = 9 Hz), 6.62 (1H, d, J = 9 Hz), 5.67 (1H, d, J = 3 Hz), 5.6-5.35 (3H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.25 (1H, m), 4.22 (1H, m), 3.88 (1H, brs), 3.18 (3H, s), |

TABLE 43-continued

| Ex. | NMR Data |
|---|---|
| | 3.15 (3H, s), 3.06 (3H, s), 3.05 (6H, s), 2.91 (3H, s), 2.51 (1H, brd, J = 5 Hz), 2.4-2.3 (2H, m), 2.2-1.9 (5H, m), 1.9-1.1 (10H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.08 (3H, d, J = 6 Hz), 1.0-0.8 (35H, m), 0.74 (3H, d, J = 7 Hz) (for a major conformer) |
| 25 | 9.38 (1H, brd, J = 9 Hz), 7.52 (1H, brd, J = 9 Hz), 6.97 (1H, d, J = 9 Hz), 6.87 (1H, d, J = 8 Hz), 6.68 (1H, d, J = 9 Hz), 5.66 (1H, d, J = 3 Hz), 5.6-5.2 (4H, m), 5.04 (1H, m), 5.0-4.8 (5H, m), 4.71 (1H, m), 4.6-4.5 (2H, m), 4.3-4.2 (2H, m), 3.74 (1H, brs), 3.30 (3H, s), 3.21 (3H, s), 3.06 (3H, s), 3.05 (3H, s), 3.03 (3H, s), 2.89 (3H, s), 2.51 (1H, brd, J = 5 Hz), 2.45-2.25 (2H, m), 2.2-1.9 (4H, m), 1.9-1.1 (10H, m), 1.66 (3H, d, J = 6 Hz), 1.41 (3H, d, J = 7 Hz), 1.33 (3H, d, J = 7 Hz), 1.19 (9H, s), 1.12 (3H, d, J = 7 Hz), 1.09 (3H, d, J = 6 Hz), 1.09 (3H, d, J = 7 Hz), 1.04-0.85 (27H, m), 0.82 (3H, d, J = 6 Hz), 0.72 (3H, d, J = 7 Hz) (for a major conformer) |
| 26 | 8.85 (1H, brd, J = 9 Hz), 7.75 (1H, brd, J = 9 Hz), 6.98 (1H, brd, J = 9 Hz), 6.88 (2H, brs), 5.64 (1H, brs), 5.55-4.49 (13H, m), 4.32-4.17 (2H, m), 3.72 (1H, brs), 3.30 (3H, s), 3.19 (3H, s), 3.08 (6H, s), 3.05 (3H, s), 2.92 (3H, s), 2.51 (1H, brs), 2.42-0.65 (69H, m) |
| 27 | 8.42 (1H, brd, J = 9 Hz), 7.85 (1H, brd, J = 8 Hz), 6.96 (1H, d, J = 8 Hz), 6.76 (1H, d, J = 9 Hz), 6.76 (1H, d, J = 9 Hz), 5.65 (1H, d, J = 3 Hz), 5.54-5.10 (5H, m), 5.05-4.78 (4H, m), 4.75-4.60 (2H, m), 4.57-4.45 (1H, m), 4.32-4.28 (2H, m), 3.86 (1H, brs), 3.25-3.05 (2H, m), 3.14 (3H, s), 3.13 (3H, s), 3.05 (3H, s), 3.00 (3H, s), 2.94 (3H, s), 2.51 (1H, brd, J = 5 Hz), 2.43-2.23 (2H, m), 2.20-0.80 (56H, m), 1.66 (3H, d, J = 6 Hz), 1.42 (3H, d, J = 6 Hz), 1.33 (3H, d, J = 6 Hz), 1.14 (3H, d, J = 7 Hz), 1.09 (3H, d, J = 7 Hz), 0.76 (3H, d, J = 7 Hz) |
| 28 | 9.21 (1H, d, J = 9.0 Hz), 7.57 (1H, d, J = 9.0 Hz), 7.29 (5H, m), 6.97 (1H, d, J = 8.5 Hz), 6.87 (1H, d, J = 8.0 Hz), 6.80 (1H, d, J = 6.8 Hz), 5.66 (1H, d, J = 2.9 Hz), 5.29-5.53 (4H, m), 5.06 (1H, m), 4.81-4.98 (4H, m), 4.72 (1H, m), 4.57 (4H, m), 4.45 (1H, m), 4.24 (2H, m), 3.72 (1H, s), 2.90 (3H, s), 3.02 (3H, s), 3.07 (6H, s), 3.22 (3H, s), 3.23 (3H, s), 2.50 (1H, d, J = 3.0 Hz), 2.35 (2H, m), 0.75-2.10 (59H, m), 1.66 (3H, d, J = 6.5 Hz), 0.72 (3H, d, J = 7.0 Hz) |
| 29 | 8.48 (1H, d, J = 9 Hz), 8.20 (1H, d, J = 9 Hz), 7.67 (1H, d, J = 9 Hz), 7.37 (1H, d, J = 9 Hz), 7.12 (1H, d, J = 8 Hz), 6.60 (1H, brs), 5.60-3.85 (14H, m), 3.8-3.6 (1H, m), 3.19 (3H, s), 3.15 (3H, s), 3.11 (3H, s), 3.05 (3H, s), 3.00 (3H, s), 2.92 (3H, s), 2.55-1.90 (6H, m), 1.88-0.74 (58H, m), 1.37 (3H, d, J = 7 Hz), 1.30 (3H, d, J = 7 Hz), 1.07 (9H, s), 0.74 (3H, d, J = 7 Hz) |
| 30 | 8.54 (1H, brd, J = 9 Hz), 7.76 (1H, d, J = 9 Hz), 6.95 (1H, d, J = 9 Hz), 6.88 (1H, d, J = 8 Hz), 6.61 (1H, d, J = 9 Hz), 5.66 (1H, d, J = 3 Hz), 5.56-5.18 (4H, m), 5.15-5.05 (1H, m), 5.03-4.80 (4H, m), 4.76-4.64 (2H, m), 4.58-4.45 (1H, m), 4.30-4.15 (2H, m), 3.86 (1H, brs), 3.12 (3H, s), 3.09 (3H, s), 3.04 (3H, s), 3.02 (3H, s), 2.97 (3H, s), 2.92 (3H, s), 2.51 (1H, brd, J = 5 Hz), 2.42-2.25 (2H, m), 2.20-0.85 (52H, m), 1.62 (3H, d, J = 6 Hz), 1.38 (3H, d, J = 8 Hz), 1.32 (3H, d, J = 7 Hz), 1.13 (3H, d, J = 6.5 Hz), 1.09 (3H, d, J = 7 Hz), 0.80 (3H, d, J = 7 Hz), 0.73 (3H, d, J = 7 Hz) |
| 31 | 7.85 (1H, brd, J = 9 Hz), 7.48 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.55-5.4 (3H, m), 5.31 (1H, dd, J = 12 and 4 Hz), 5.12 (1H, dd, J = 10 and 4 Hz), 5.0-4.8 (4H, m), 4.75-4.55 (2H, m), 4.27-4.10 (2H, m), 3.88 (1H, brs), 3.13 (3H, s), 3.11 (3H, s), 3.05 (3H, s), 3.02 (3H, s), 2.98 (3H, s), 2.92 (3H, s), 2.51 (1H, brd, J = 5 Hz), 2.4-2.3 (2H, m), 2.2-1.9 (5H, m), 1.9-1.1 (10H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.09 (3H, d, J = 6 Hz), 1.0-0.8 (33H, m), 0.74 (3H, d, J = 7 Hz) |
| 32 | 9.10 (1H, brd, J = 9 Hz), 7.60 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (2H, m), 5.35-5.25 (2H, m), 5.12 (1H, dd, J = 10 and 4 Hz), 5.0-4.8 (3H, m), 4.75-4.65 (2H, m), 4.73 (1H, m), 4.53 (1H, m), 4.31-4.10 (3H, m), 3.72 (1H, brs), 3.32 (3H, s), 3.22 (3H, s), 3.20 (3H, s), 3.05 (6H, s), 3.03 (3H, s), 2.90 (3H, s), 2.51 (1H, brd, J = 5 Hz), 2.4-2.3 (2H, m), 2.2-1.9 (4H, m), 1.9-1.1 (10H, m), 1.66 (3H, d, J = 6 Hz), 1.40 (3H, d, J = 7.5 Hz), 1.35 (3H, d, J = 6 Hz), 1.13 (3H, d, J = 6.5 Hz), 1.09 (3H, d, J = 7 Hz), 1.09 (3H, d, J = 7 Hz), 1.0-0.8 (30H, m) 0.74 (3H, d, J = 7 Hz) (for a major conformer) |
| 33 | 9.10 (1H, brd, J = 9 Hz), 7.60 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (2H, m), 5.35-5.25 (2H, m), 5.12 (1H, dd, J = 10 and 4 Hz), 5.0-4.8 (3H, m), 4.75-4.65 (2H, m), 4.73 (1H, m), 4.53 (1H, m), 4.31-4.10 (3H, m), 3.72 (1H, brs), 3.60 (1H, m), 3.45 (1H, m), 3.29 (3H, s), 3.24 (3H, s), 3.06 (6H, s), 3.03 (3H, s), 2.90 (3H, s), 2.51 (1H, brd, J = 5 Hz), 2.4-2.3 (2H, m), 2.2-1.9 (4H, m), 1.9-1.1 (10H, m), 1.66 (3H, d, J = 6 Hz), 1.40 (3H, d, J = 7.5 Hz), 1.35 (3H, d, J = 6 Hz), 1.13 (3H, d, J = 6.5 Hz), 1.09 (3H, d, J = 7 Hz), 1.09 (3H, d, J = 6 Hz), 1.0-0.8 (33H, m), 0.74 (3H, d, J = 7 Hz) (for a major conformer) |
| 34 | 8.80 (1H, brd, J = 9 Hz), 7.45-7.25 (5H, m), 7.60 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.2 (4H, m), 5.12 (1H, dd, J = 10 and 4 Hz), 5.0-4.65 (5H, m), 4.58 (1H, m), 4.45 (1H, m), 4.31-4.10 (3H, m), 3.9-3.8 (2H, m), 3.55 (1H, brs), 3.32 (3H, s), 3.22 (3H, s), 3.05 (6H, s), 3.02 (3H, s), 2.90 (3H, s), 2.51 (1H, brd, J = 5 Hz), 2.4-2.3 (2H, m), 2.2-1.9 (4H, m), 1.9-1.1 (10H, m), 1.66 (3H, d, J = 6 Hz), 1.40 (3H, d, J = 7.5 Hz), 1.13 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) (for a major conformer) |
| 35 | 9.16 (1H, brd, J = 9 Hz), 7.61 (1H, brd, J = 9 Hz), 6.95 (1H, d, J = 8 Hz), 6.85 (1H, d, J = 8 Hz), 6.62 (1H, brd, J = 8 Hz), 5.64 (1H, d, J = 3 Hz), 5.52-4.44 (13H, m), 4.33-4.09 (2H, m), 3.74 (1H, brs), 3.32 (3H, s), 3.20 (3H, s), 3.07 (6H, s), 3.02 (3H, s), 2.92 (3H, s), 2.49 (1H, brs), 2.43-0.77 (57H, m), 1.68 (3H, d, J = 6 Hz), 1.62 (3H, d, J = 6 Hz), 1.35 (3H, d, J = 6 Hz), 1.18 (9H, s), 0.74 (3H, d, J = 7 Hz) |
| 36 | 8.45 (1H, brd, J = 9 Hz), 7.78 (1H, brd, J = 9 Hz), 6.95 (1H, d, J = 9 Hz), 6.86 (1H, d, J = 8 Hz), 6.62 (1H, d, J = 9 Hz), 5.67 (1H, d, J = 3 Hz), 5.6-5.4 (3H, m), 5.31 (1H, dd, J = 12 and 4 Hz), 5.12 (1H, dd, J = 10 and 4 Hz), 5.0-4.8 (4H, m), 4.75-4.65 (2H, m), 4.53 (1H, m), 4.27 (1H, m), 4.21 (1H, m), 3.88 (1H, brs), 3.13 (3H, s), 3.11 (3H, s), 3.05 (3H, s), 3.01 (3H, s), 2.98 (3H, s), 2.92 (3H, s), 2.51 (1H, brd, J = 5 Hz), 2.4-2.3 (2H, m), 2.2-1.9 (5H, m), 1.9-1.1 (11H, m), 1.66 (3H, d, J = 6 Hz), 1.38 (3H, d, J = 7.5 Hz), 1.33 (3H, d, J = 6 Hz), 1.13 (3H, d, J = 6.5 Hz), 1.09 (3H, d, J = 7 Hz), 1.09 (3H, d, J = 6 Hz), 1.0-0.8 (34H, m), 0.74 (3H, d, J = 7 Hz) (for a major conformer) |
| 37 | 7.83 (1H, brd, J = 9 Hz), 7.55 (1H, brd, J = 9 Hz), 7.32-7.20 (5H, m), 7.05 (1H, d, J = 9 Hz), 7.02 (1H, d, J = 9 Hz), 6.70 (1H, d, J = 8 Hz), 5.67 (1H, d, J = 3 Hz), 5.6-5.4 (2H, m), 5.39-5.32 (2H, m), 5.15-5.05 (2H, m), 4.95-4.90 (1H, m), 4.83-4.7 (4H, m), 4.63 (1H, m), 4.37-4.32 (4H, m), 3.65 (1H, m), 3.38 (3H, s), 3.33 (3H, s), 3.05 (3H, s), 3.02 (3H, s), 3.00 (3H, s), 2.62 (3H, s), 2.49 (1H, brd, J = 5 Hz), 2.4-2.3 (2H, m), 2.2-1.8 (4H, m), 1.9-0.8 (46H, m), 1.66 (3H, d, J = 6 Hz), 1.33 (3H, d, J = 6 Hz), 1.14 (3H, d, |

TABLE 43-continued

| Ex. | NMR Data |
|---|---|
| | J = 6.5 Hz), 1.09 (3H, d, J = 7 Hz), 1.08 (3H, d, J = 6 Hz), 0.74 (3H, d, J = 7 Hz) (for a major conformer) |
| 38 | 9.18 (1H, d, J = 8.5 Hz), 7.45 (1H, d, J = 9.0 Hz), 7.06 (1H, d, J = 9.0 Hz), 6.99 (1H, d, J = 9.0 Hz), 6.85 (1H, d, J = 7.5 Hz), 5.70 (1H, d, J = 3.5 Hz), 5.27 (4H, m), 5.17 (1H, m), 4.94 (3H, m), 4.69 (3H, m), 4.54 (1H, m), 4.29 (2H, m), 3.71 (1H, m), 3.60 (1H, m), 3.46 (1H, m), 3.21 (3H, s), 3.09 (3H, s), 3.07 (3H, s), 3.02 (3H, s), 2.89 (3H, s), 2.50 (1H, d, J = 5.0 Hz), 2.35 (2H, m), 0.80-2.20 (69H, m), 0.72 (3H, d, J = 7.0 Hz) |
| 39 | 7.72 (1H, brd, J = 9 Hz), 7.45-7.40 (5H, m), 7.30 (1H, d, J = 9 Hz), 7.15 (1H, d, J = 9 Hz), 7.05 (1H, d, J = 9 Hz), 6.90 (1H, d, J = 8 Hz), 6.70 (1H, d, J = 9 Hz), 5.67 (1H, d, J = 3 Hz), 5.56-5.4 (2H, m), 5.39-5.32 (2H, m), 5.15-5.05 (2H, m), 5.11-5.10 (2H, m), 4.95-4.90 (2H, m), 4.9-4.5 (3H, m), 4.4-4.3 (2H, m), 4.19-4.15 (1H, m), 4.00-3.95 (2H, m), 3.55 (1H, brs), 3.36 (3H, s), 3.25 (3H, s), 3.20 (3H, s), 3.05 (3H, s), 2.94 (3H, s), 2.50 (1H, brd, J = 5 Hz), 2.4-2.3 (2H, m), 2.2-1.8 (4H, m), 1.9-0.8 (53H, m), 1.66 (3H, d, J = 6 Hz), 1.50 (3H, d, J = 6 Hz), 1.35 (3H, d, J = 6.5 Hz), 1.25 (3H, d, J = 7 Hz), 1.08 (3H, d, J = 6 Hz), 0.74 (3H, d, J = 7 Hz) (for a major conformer) |
| 40 | 8.34 (1H, d, J = 8.0 Hz), 8.17 (1H, d, J = 8.5 Hz), 7.15 (1H, d, J = 7.5 Hz), 6.99 (1H, d, J = 8.5 Hz), 6.97 (1H, d, J = 7.0 Hz), 5.80 (1H, d, J = 9.0 Hz), 5.25-5.54 (5H, m), 4.95 (3H, m), 4.53-4.75 (4H, m), 4.14 (1H, m), 4.05 (1H, m), 3.92 (1H, m), 3.78 (1H, m), 3.59 (1H, m), 3.44 (3H, s), 3.16 (3H, s), 3.06 (6H, s), 2.70 (3H, s), 2.29 (3H, m), 0.75-2.15 (72H, m) |
| 41 | 8.00 (1H, brd, J = 9 Hz), 7.67 (1H, brd, J = 9 Hz), 7.18 (1H, d, J = 9 Hz), 6.90 (1H, d, J = 8 Hz), 6.80 (1H, d, J = 9 Hz), 5.72 (1H, d, J = 3 Hz), 5.6-5.4 (2H, m), 5.39-5.32 (2H, m), 5.25-5.15 (2H, m), 4.95-4.90 (1H, m), 4.85-4.75 (4H, m), 4.60 (1H, m), 4.32-4.30 (2H, m), 3.89 (1H, brs), 3.32 (3H, s), 3.07 (3H, s), 3.03 (6H, s), 3.00 (3H, s), 2.72 (3H, s), 2.50 (1H, brd, J = 5 Hz), 2.4-2.3 (2H, m), 2.2-1.8 (4H, m), 1.9-0.8 (55H, m), 1.61 (3H, d, J = 6 Hz), 1.30 (3H, d, J = 6 Hz), 1.12 (3H, d, J = 6.5 Hz), 1.02 (3H, d, J = 7 Hz), 1.01 (3H, d, J = 6 Hz), 0.74 (3H, d, J = 7 Hz) (for a major conformer) |
| 42 | 7.82 (1H, brd, J = 9 Hz), 7.6-7.5 (5H, m), 6.85 (1H, d, J = 9 Hz), 6.90 (2H, d, J = 8 Hz), 6.62 (1H, d, J = 9 Hz), 5.67 (1H, d, J = 3 Hz), 5.6-5.4 (2H, m), 5.39-5.32 (2H, m), 5.15-5.05 (2H, m), 5.11 (2H, m), 4.95-4.90 (1H, m), 4.9-4.7 (4H, m), 4.63 (1H, m), 4.37-4.32 (2H, m), 3.75-3.70 (4H, m), 3.88 (1H, brs), 3.36 (3H, s), 3.16 (6H, s), 3.06 (6H, s), 3.20 (3H, s), 3.19 (3H, s), 2.51 (1H, brd, J = 5 Hz), 2.4-2.3 (2H, m), 2.2-1.8 (4H, m), 1.9-0.8 (52H, m), 1.66 (3H, d, J = 6 Hz), 1.33 (3H, d, J = 6 Hz), 1.14 (3H, d, J = 6.5 Hz), 1.09 (3H, d, J = 7 Hz), 1.08 (3H, d, J = 6 Hz), 0.74 (3H, d, J = 7 Hz) (for a major conformer) |
| 43 | 8.15 (1H, brd, J = 9 Hz), 7.95 (1H, d, J = 9 Hz), 7.85 (1H, d, J = 9 Hz), 7.20 (1H, d, J = 9 Hz), 6.90 (2H, d, J = 8 Hz), 5.80 (1H, d, J = 3 Hz), 5.52-5.2 (4H, m), 5.1-4.85 (3H, m), 4.75-4.70 (2H, m), 4.65-4.51 (4H, m), 4.2-4.0 (4H, m), 3.55 (1H, brs), 3.13 (3H, s), 3.16 (6H, s), 3.06 (6H, s), 2.76 (3H, s), 2.4-2.2 (3H, m), 2.2-1.8 (4H, m), 1.9-0.8 (58H, m), 1.66 (3H, d, J = 6 Hz), 1.50 (3H, d, J = 6 Hz), 1.35 (3H, d, J = 6.5 Hz), 1.25 (3H, d, J = 7 Hz), 1.08 (3H, d, J = 6 Hz), 0.74 (3H, d, J = 7 Hz) (for a major conformer) |
| 44 | 8.62 (1H, brd, J = 9 Hz), 7.70 (1H, brd, J = 9 Hz), 7.50 (1H, brd, J = 9 Hz), 7.15 (1H, brd, J = 9 Hz), 7.05 (1H, d, J = 8 Hz), 6.62 (1H, d, J = 9 Hz), 5.71 (1H, d, J = 3 Hz), 5.55-5.45 (2H, m), 5.39-5.30 (2H, m), 5.20-5.15 (2H, m), 5.08-4.80 (4H, m), 4.73-4.60 (1H, m), 4.62-4.52 (1H, m), 4.45-4.25 (2H, m), 3.50 (1H, brs), 3.25 (3H, s), 3.06 (3H, s), 3.01 (3H, s), 2.95 (3H, |

TABLE 43-continued

| Ex. | NMR Data |
|---|---|
| | s), 2.93 (3H, s), 2.31 (1H, brd, J = 5 Hz), 2.2-2.0 (2H, m), 2.0-1.75 (4H, m), 1.9-0.8 (55H, m), 1.55 (3H, d, J = 6 Hz), 1.35 (3H, d, J = 7.5 Hz), 1.33 (3H, d, J = 6 Hz), 1.12 (3H, d, J = 6.5 Hz) 1.09 (3H, d, J = 7 Hz), 1.08 (3H, d, J = 6 Hz) (for a major conformer) |
| 45 | 8.13 (1H, brd, J = 9 Hz), 7.75 (1H, brd, J = 9 Hz), 7.32 (1H, d, J = 9 Hz), 7.25 (1H, d, J = 8 Hz)), 7.05 (2H, d, J = 8 Hz), 5.81 (1H, d, J = 3 Hz), 5.55-5.45 (2H, m), 5.42-5.28 (2H, m), 5.10-5.05 (1H, m), 5.03-4.90 (2H, m), 4.80-4.70 (3H, m), 4.65-4.51 (2H, m), 4.30-4.21 (2H, m), 3.55 (1H, brs), 3.52 (3H, s), 3.16 (3H, s), 3.08 (6H, s), 2.75 (3H, s), 2.39-2.05 (3H, m), 2.0-1.75 (4H, m), 1.9-0.8 (55H, m), 1.57 (3H, d, J = 6 Hz), 1.35 (3H, d, J = 7.5 Hz), 1.23 (3H, d, J = 6 Hz), 1.12 (3H, d, J = 6.5 Hz), 1.07 (3H, d, J = 7 Hz), 0.74 (3H, d, J = 6 Hz) (for a major conformer) |
| 46 | 8.50 (1H, brd, J = 9 Hz), 7.75 (1H, brd, J = 9 Hz), 7.35 (1H, d, J = 9 Hz), 7.35-7.25 (5H, m), 7.32 (1H, d, J = 8 Hz)), 7.20 (1H, d, J = 8 Hz), 7.02 (1H, d, J = 9 Hz), 5.71 (1H, d, J = 3 Hz), 5.55-5.45 (2H, m), 5.39-5.30 (2H, m), 5.20-5.15 (2H, m), 5.08-4.80 (4H, m), 4.73-4.60 (1H, m), 4.62-4.52 (1H, m), 4.3-4.48 (2H, m), 4.4-4.25 (2H, m), 3.75-3.50 (2H, m), 3.65 (1H, brs), 3.25 (3H, s), 3.15 (3H, s), 3.11 (3H, s), 3.05 (3H, s), 2.95 (3H, s), 2.31 (1H, brd, J = 5 Hz), 2.2-2.0 (2H, m), 2.0-1.75 (4H, m), 1.9-0.8 (46H, m), 1.55 (3H, d, J = 6 Hz), 1.35 (3H, d, J = 7.5 Hz), 1.33 (3H, d, J = 6 Hz), 1.12 (3H, d, J = 6.5 Hz), 1.09 (3H, d, J = 7 Hz), 0.74 (3H, d, J = 6 Hz) (for a major conformer) |
| 52 | 8.16 (1H, d, J = 9 Hz), 7.88 (1H, d, J = 9 Hz), 7.11 (1H, d, J = 7 Hz), 7.02 (1H, d, J = 9 Hz), 6.98 (1H, d, J = 8 Hz), 5.88 (1H, d, J = 11 Hz), 5.52-5.26 (5H, m), 5.04-4.91 (3H, m), 4.80 (1H, d, J = 15 Hz), 4.76-4.66 (2H, m), 4.57 (1H, m), 4.21 (1H, m), 4.00-3.88 (2H, m), 3.56 (1H, brd, J = 5 Hz), 3.48 (3H, s), 3.44 (3H, s), 3.15 (3H, s), 3.13-3.05 (2H, m), 3.08 (3H, s), 3.05 (3H, s), 2.78 (3H, s), 2.38-2.26 (2H, m), 2.10-1.90 (4H, m), 1.86-1.56 (3H, m), 1.63 (3H, brd, J = 6 Hz), 1.54-1.0 (7H, m), 1.35 (3H, d, J = 7 Hz), 1.19 (3H, d, J = 7 Hz), 1.14 (3H, d, J = 6 Hz), 1.10 (3H, d, J = 6 Hz), 1.09 (9H, s), 1.01 (3H, d, J = 6 Hz), 1.00 (3H, d, J = 6 Hz), 0.99 (3H, d, J = 7 Hz), 0.93 (3H, d, J = 7 Hz), 0.91 (3H, d, J = 7 Hz), 0.88 (3H, d, J = 7 Hz), 0.84 (3H, d, J = 7 Hz), 0.84 (3H, d, J = 7 Hz), 0.78 (3H, d, J = 6 Hz), 0.78 (3H, d, J = 7 Hz), 0.76 (3H, d, J = 7 Hz) |
| 53 | 8.06 (1H, d, J = 9 Hz), 7.57 (1H, d, J = 9 Hz), 7.35-7.20 (5H, m), 6.98 (1H, d, J = 7 Hz), 6.92 (1H, d, J = 9 Hz), 6.78 (1H, d, J = 8 Hz), 5.58 (1H, d, J = 11 Hz), 5.46-5.21 (5H, m), 5.05-4.87 (4H, m), 5.02-4.75 (2H, m), 4.67 (2H, m), 4.48-4.42 (1H, m), 4.22-4.15 (1H, m), 3.72 (1H, m), 3.45 (1H, m), 3.35-3.08 (2H, m), 3.12 (3H, s), 3.09 (3H, s), 3.02 (3H, s), 3.24-2.95 (2H, m), 3.00 (3H, s), 2.99 (3H, s), 2.83 (3H, m), 2.81 (3H, s), 2.58-2.22 (4H, m), 2.15-1.82 (3H, m), 1.86-1.62 (6H, m), 1.61 (3H, brd, J = 6 Hz), 1.68-1.05 (7H, m), 1.31 (3H, d, J = 7 Hz), 1.16 (3H, d, J = 7 Hz), 1.13 (3H, d, J = 6 Hz), 1.11 (3H, d, J = 6 Hz), 1.09 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 55 | 8.15 (1H, d, J = 9 Hz), 8.07 (1H, d, J = 9 Hz), 7.07 (1H, d, J = 7 Hz), 6.99 (1H, d, J = 9 Hz), 6.87 (1H, d, J = 8 Hz), 5.88 (1H, d, J = 11 Hz), 5.54-5.75 (5H, m), 5.04-4.85 (3H, m), 4.80-4.50 (3H, m), 4.32-4.03 (6H, m), 3.46 (6H, s), 3.35-2.60 (6H, m), 3.15 (3H, s), 3.07 (3H, s), 3.04 (3H, s), 2.74 (3H, s), 2.42-2.22 (2H, m), 210-0.65 (58H, m), 1.68 (3H, d, J = 6 Hz), 1.63 (3H, d, J = 6 Hz), 1.18 (3H, d, J = 7 Hz) |
| 56 | 8.12 (1H, d, J = 9 Hz), 7.95 (1H, d, J = 9 Hz), 7.08 (1H, d, J = 7 Hz), 7.00 (1H, d, J = 9 Hz), 6.83 (1H, d, J = 8 Hz), 5.88 (1H, d, J = 11 Hz), 5.52-5.21 (5H, m), |

TABLE 43-continued

| Ex. | NMR Data |
|---|---|
|  | 5.05-4.91 (3H, m), 4.77 (1H, d, J = 15 Hz), 4.76-4.68 (2H, m), 4.57 (1H, m), 4.48 (1H, m), 4.23-4.20 (2H, m), 3.97-3.88 (1H, m), 3.48 (3H, s), 3.44 (3H, s), 3.28 (3H, s), 3.21-2.97 (2H, m), 3.12 (3H, s), 3.11-2.98 (2H, m,), 3.09 (3H, s), 2.78 (3H, s), 2.38-2.26 (2H, m), 2.17-1.92 (4H, m), 1.86-1.62 (3H, m), 1.63 (3H, brd, J = 6 Hz), 1.57-1.0 (11H, m), 1.33 (3H, d, J = 7 Hz), 1.21 (3H, d, J = 7 Hz), 1.13 (3H, d, J = 6 Hz), 1.11 (3H, d, J = 6 Hz), 1.09 (3H, d, J = 6 Hz), 1.00 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 57 | 8.12 (1H, d, J = 8 Hz), 7.92 (1H, d, J = 8 Hz), 7.35-7.25 (4H, m), 7.20 (2H, d, J = 6 Hz), 7.10 (1H, d, J = 6 Hz), 6.99 (1H, d, J = 8 Hz), 6.86 (1H, d, J = 7 Hz), 5.86 (1H, m), 5.54-5.25 (5H, m), 5.09-4.83 (3H, m), 4.79-4.65 (2H, m), 4.62-4.37 (3H, m), 4.32 (1H, d, J = 9 Hz), 4.28-4.17 (1H, m), 3.98-3.80 (2H, m), 3.45 (3H, s), 3.40-3.00 (3H, m), 3.38 (3H, s), 3.14 (3H, s), 3.05 (3H, s), 3.02 (3H, s), 2.63 (3H, s), 2.38-2.75 (1H, m), 2.12-1.89 (4H, m), 1.85-0.70 (52H, m), 1.63 (3H, d, J = 6 Hz), 1.34 (3H, d, J = 7 Hz) |
| 58 | 8.11 (1H, d, J = 9 Hz), 7.95 (1H, d, J = 9 Hz), 7.08 (1H, d, J = 7 Hz), 7.02 (1H, d, J = 9 Hz), 6.82 (1H, d, J = 8 Hz), 5.88 (1H, d, J = 11 Hz), 5.51-5.25 (5H, m), 5.01-4.82 (3H, m), 4.72 (1H, d, J = 15 Hz), 4.68-4.61 (2H, m), 4.55 (1H, m), 4.21 (2H, m), 3.97-3.92 (1H, m), 3.68-3.53 (4H, m), 3.48-3.45 (4H, m), 3.48 (3H, s), 3.47 (3H, s), 3.15 (3H, s), 3.21-2.97 (2H, m), 3.09 (3H, s), 3.07 (3H, m), 2.81 (3H, s), 2.35-2.26 (2H, m), 2.19-1.95 (4H, m), 1.86-1.62 (3H, m), 1.59 (3H, brd, J = 6 Hz), 1.57-1.0 (8H, m), 1.33 (3H, d, J = 7 Hz), 1.18 (3H, d, J = 7 Hz), 1.13 (3H, d, J = 6 Hz), 1.11 (3H, d, J = 6 Hz), 1.09 (3H, d, J = 6 Hz), 1.00 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 59 | 8.14 (1H, d, J = 9 Hz), 7.82 (1H, d, J = 9 Hz), 7.11 (1H, d, J = 7 Hz), 6.98 (1H, d, J = 9 Hz), 6.84 (1H, d, J = 8 Hz), 5.82 (1H, d, J = 11 Hz), 5.55-5.15 (5H, m), 5.06-4.65 (6H, m), 4.64-4.50 (1H, m), 4.32-4.15 (2H, m), 4.07-3.96 (1H, m), 3.76-3.53 (2H, m), 3.46 (3H, s), 3.42 (3H, s), 3.20-3.05 (2H, m), 3.15 (3H, s), 3.06 (3H, s), 3.03 (3H, s), 2.76 (3H, s), 2.38-2.22 (2H, m), 2.08-0.80 (44H, m), 1.63 (3H, d, J = 6 Hz), 1.34 (3H, d, J = 7 Hz), 1.13 (9H, s), 1.00 (3H, d, J = 7 Hz), 0.84 (3H, d, J = 7 Hz), 0.79 (3H, d, J = 7 Hz) |
| 60 | 9.03 (1H, d, J = 9 Hz), 7.67 (1H, d, J = 9 Hz), 6.98 (1H, d, J = 6 Hz), 6.90 (1H, d, J = 9 Hz), 6.84 (1H, d, J = 8 Hz), 5.83 (1H, d, J = 11 Hz), 5.55-5.26 (5H, m), 5.23-5.14 (1H, m), 5.08-4.49 (5H, m), 4.30-4.15 (2H, m), 4.05-3.94 (1H, m), 3.45 (3H, s), 3.30-3.03 (2H, m), 3.16 (3H, s), 3.15 (3H, s), 3.05 (3H, s), 2.96 (3H, s), 2.90 (3H, s), 2.45-2.24 (2H, m), 2.10-0.75 (61H, m), 1.19 (3H, d, J = 7 Hz), 1.05 (3H, d, J = 7 Hz), 0.80 (3H, d, J = 7 Hz), 0.72 (3H, d, J = 7 Hz) |
| 61 | 8.13 (1H, d, J = 8 Hz), 8.03 (1H, d, J = 8 Hz), 7.10 (1H, d, J = 6 Hz), 7.00 (1H, d, J = 8 Hz), 6.88 (1H, d, J = 7 Hz), 5.87 (1H, d, J = 9 Hz), 5.55-5.26 (5H, m), 5.09-4.84 (5H, m), 4.78-4.64 (2H, m), 4.62-4.50 (1H, m), 4.28-4.16 (2H, m), 3.99-3.89 (1H, m), 3.47 (3H, s), 3.45 (3H, s), 3.27-2.98 (4H, m), 3.15 (3H, s), 3.07 (3H, s), 3.04 (3H, s), 2.74 (3H, s), 2.43-2.16 (2H, m), 2.12-1.88 (4H, m), 1.85-0.70 (54H, m), 1.64 (3H, d, J = 6 Hz), 1.36 (3H, d, J = 7 Hz), 1.18 (3H, d, J = 7 Hz) |
| 62 | 8.13 (1H, d, J = 9 Hz), 8.05 (1H, d, J = 9 Hz), 7.11 (1H, d, J = 7 Hz), 7.00 (1H, d, J = 9 Hz), 6.91 (1H, d, J = 8 Hz), 5.90 (1H, d, J = 11 Hz), 5.53-5.28 (5H, m), 5.07-4.79 (4H, m), 4.77-4.66 (2H, m), 4.64-4.50 (2H, m), 4.21 (2H, brd, J = 11 Hz), 3.47 (3H, s), 3.45 (3H, s), 3.17 (3H, s), 3.07 (3H, s), 3.04 (3H, s), 2.82-2.75 (1H, m), 2.74 (3H, s), 2.39-2.26 (2H, m), 2.15-0.78 (57H, m), 1.63 (3H, d, J = 6 Hz), 1.18 (3H, d, J = 7 Hz) 1.14 (3H, d, J = 7 Hz), 0.78 (3H, d, J = 7 Hz), 0.76 (3H, d, J = 7 Hz) |
| 63 | 9.33 (1H, brd, J = 9 Hz), 8.14, 7.98 (1H, brd, J = 9 Hz), 7.52-7.15 (5H, m), 7.12 (1H, d, J = 7 Hz), 7.00 (1H, d, J = 9 Hz), 6.86 (1H, d, J = 8 Hz), 6.42 (1H, brs), 5.57-5.17 (5H, m), 5.07-4.82 (4H, m), 4.78-4.50 (3H, m), 4.34-4.15 (2H, m), 4.08-3.97 (1H, m), 3.75 (1H, brs), 3.47, 3.42 (3H, s), 3.24 (3H, s), 3.22-2.93 (2H, m), 3.16 (3H, s), 3.12 (3H, s), 3.06 (3H, s), 2.92 (3H, s), 2.55-2.22 (3H, m), 2.17-0.80 (45H, m), 1.67 (3H, d, J = 6 Hz), 1.34 (3H, d, J = 7 Hz), 0.82 (3H, d, J = 7 Hz), 0.72 (3H, d, J = 7 Hz) |
| 64 | 8.16 (1H, d, J = 9 Hz), 8.01 (1H, d, J = 9 Hz), 7.18 (1H, d, J = 7 Hz), 7.12 (1H, d, J = 9 Hz), 7.02 (1H, d, J = 8 Hz), 5.87 (1H, d, H, J = 11 Hz), 5.54-5.27 (5H, m), 5.06-4.87 (4H, m), 4.77-4.68 (2H, m), 4.61-4.54 (1H, m), 4.32-4.14 (2H, m), 3.98-3.92 (1H, m), 3.77-3.70 (1H, m), 3.47 (3H, s), 3.45 (3H, s), 3.17 (3H, s), 3.16-3.07 (2H, m), 3.09 (3H, s), 3.05 (3H, s), 2.75 (3H, s), 2.45-2.20 (3H, m), 2.10-0.75 (53H, m), 1.64 (3H, d, J = 6 Hz), 1.35 (3H, d, J = 7 Hz), 1.18 (3H, d, J = 7 Hz), 1.00 (3H, d, J = 7 Hz), 0.95 (3H, d, J = 7 Hz) |
| 65 | 8.15 (1H, d, J = 9 Hz), 7.99 (1H, d, J = 9 Hz), 7.08 (1H, d, J = 7 Hz), 7.00 (1H, d, J = 9 Hz), 6.92 (1H, d, J = 8 Hz), 5.89 (1H, d, J = 11 Hz), 5.51-5.28 (5H, m), 5.03-4.85 (3H, m), 4.76-4.68 (3H, m), 4.61-4.51 (1H, m), 4.21 (1H, m), 3.97-3.85 (1H, m), 3.71 (1H, brd, J = 5 Hz), 3.48 (3H, s), 3.46 (3H, s), 3.18 (3H, s), 18-3.02 (2H, m), 3.09 (3H, s), 3.07 (3H, s), 2.92 (3H, s), 2.38-2.24H, s), 2.17-1.92 (4H, m), 1.86-1.62 (3H, m), 1.65 (3H, brd, J = 6 Hz), 1.57-1.0 (7H, m), 1.33 (3H, d, J = 7 Hz), 1.16 (3H, d, J = 7 Hz), 1.13 (3H, d, J = 6 Hz), 1.09 (3H, d, J = 6 Hz), 1.05 (9H, s), 1.00 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 66 | 8.15 (1H, d, J = 9 Hz), 8.08 (1H, d, J = 9 Hz), 7.08 (1H, d, J = 7 Hz), 6.98 (1H, d, J = 9 Hz), 6.87 (1H, d, J = 8 Hz), 5.87 (1H, d, J = 11 Hz), 5.54-5.25 (5H, m), 5.04-4.84 (3H, m), 4.75-4.65 (2H, m), 4.60-4.50 (1H, m), 4.32-4.15 (2H, m), 4.03-3.88 (2H, m), 3.46 (6H, s), 3.45-2.85 (6H, m), 3.16 (3H, s), 3.07 (3H, s), 3.04 (3H, s), 2.75 (3H, s), 2.40-2.24 (2H, m), 2.08-1.86 (4H, m), 1.82-0.73 (48H, m), 1.65 (3H, d, J = 6 Hz), 1.61 (3H, d, J = 6 Hz), 1.33 (3H, d, J = 7 Hz), 1.17 (3H, d, J = 7 Hz) |
| 67 | 8.13 (1H, d, J = 9 Hz), 7.90 (1H, d, J = 9 Hz), 7.11 (1H, d, J = 7 Hz), 7.00 (1H, d, J = 9 Hz), 6.86 (1H, d, J = 8 Hz), 5.88 (1H, d, J = 11 Hz), 5.60-5.22 (5H, m), 5.08-4.50 (7H, m), 4.30-4.15 (1H, m), 4.00-3.89 (1H, m), 3.78-3.68 (1H, m), 3.65-3.53 (1H, m), 3.46 (3H, s), 3.42 (3H, s), 3.34-2.20 (1H, m), 3.17 (3H, s), 3.09 (3H, s), 3.06 (3H, s), 2.80 (3H, s), 2.42-2.22 (2H, m), 2.12-0.62 (59H, m), 1.64 (3H, d, J = 7 Hz), 1.35 (3H, d, J = 7 Hz) |
| 68 | 8.16 (1H, d, J = 9 Hz), 7.92 (1H, d, J = 9 Hz), 7.09 (1H, d, J = 7 Hz), 7.00 (1H, d, J = 9 Hz), 6.89 (1H, d, J = 8 Hz), 5.89 (1H, d, J = 11 Hz), 5.51-5.25 (5H, m), 5.05-4.89 (3H, m), 4.77 (1H, d, J = 15 Hz), 4.75-4.65 (2H, m), 4.59 (1H, m), 4.31-4.15 (3H, m), 3.97-3.89 (2H, m), 3.75-3.69 (1H, m), 3.68 (1H, m), 3.48 (3H, s), 3.44 (3H, s), 3.32-2.97 (2H, m), 3.32 (3H, s), 3.15 (3H, s), 3.07 (3H, m), 3.05 (3H, s), 2.81 (3H, s), 2.38-1.92 (6H, m), 1.86-1.65 (3H, m), 1.62 (3H, brd, J = 6 Hz), 1.59-1.03 (6H, m), 1.33 (3H, d, J = 7 Hz), 1.16 (3H, d, J = 7 Hz), 1.14 (3H, d, J = 6 Hz), 1.11 (3H, d, J = 6 Hz), 1.09 (3H, d, J = 6 Hz), 1.00 (3H, d, J = 6 Hz), 0.99 (3H, d, J = 7 Hz), 0.94 (3H, d, J = 7 Hz), 0.92 (3H, d, J = 7 Hz), 0.89 (3H, d, J = 7 Hz), 0.86 (3H, d, J = 7 Hz), 0.83 (3H, d, J = 7 Hz), 0.79 (3H, d, J = 6 Hz), 0.78 (3H, d, J = 7 Hz), 0.77 (3H, d, J = 7 Hz) |

TABLE 43-continued

| Ex. | NMR Data |
|---|---|
| 69 | 8.16 (1H, d, J = 9 Hz), 7.95 (1H, d, J = 9 Hz), 7.08 (1H, d, J = 7 Hz), 7.00 (1H, d, J = 9 Hz), 6.87 (1H, d, J = 8 Hz), 5.88 (1H, d, J = 11 Hz), 5.51-5.25 (5H, m), 5.05-4.87 (3H, m), 4.77 (1H, d, J = 15 Hz), 4.76-4.55 (2H, m), 4.57 (1H, m), 4.21 (1H, m), 3.97-3.88 (1H, m), 3.71 (1H, brd, J = 5 Hz), 3.70 (1H, m), 3.48 (3H, s), 3.44 (3H, s), 3.28 (3H, s), 3.21-2.97 (2H, m), 3.15 (3H, s), 3.07 (3H, s), 3.05 (3H, m), 2.81 (3H, s), 2.38-2.26 (2H, m), 2.17-1.92 (4H, m), 1.86-1.62 (3H, m), 1.63 (3H, brd, J = 6 Hz), 1.57-1.0 (7H, m), 1.33 (3H, d, J = 7 Hz), 1.16 (3H, d, J = 7 Hz), 1.13 (3H, d, J = 6 Hz), 1.11 (3H, d, J = 6 Hz), 1.09 (3H, d, J = 6 Hz), 1.00 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 70 | 8.12 (1H, d, J = 9 Hz), 7.93 (1H, d, J = 9 Hz), 7.07 (1H, d, J = 7 Hz), 7.01 (1H, d, J = 9 Hz), 6.87 (1H, d, J = 8 Hz), 5.88 (1H, d, J = 11 Hz), 5.51-5.27 (5H, m), 5.05-4.87 (3H, m), 4.77 (1H, d, J = 15 Hz), 4.76-4.65 (2H, m), 4.61-4.51 (1H, m), 4.25-4.18 (1H, m), 3.97-3.88 (1H, m), 3.71 (1H, brd, J = 5 Hz), 3.70 (1H, m), 3.50 (3H, s), 3.45 (3H, s), 3.16 (3H, s), 3.21-2.97 (2H, m), 3.07 (3H, s), 3.03 (3H, s), 2.95-2.92 (6H, m), 2.81 (3H, s), 2.38-2.26 (2H, m), 2.17-1.92 (4H, m), 1.86-1.62 (3H, m), 1.62 (3H, brd, J = 6 Hz), 1.57-1.0 (7H, m), 1.32 (3H, d, J = 7 Hz), 1.16 (3H, d, J = 7 Hz), 1.11 (3H, d, J = 6 Hz), 1.10 (3H, d, J = 6 Hz), 1.09 (3H, d, J = 6 Hz), 1.00 (3H, d, J = 6 Hz), 0.99 (3H, d, J = 7 Hz), 0.93 (3H, d, J = 7 Hz), 0.91 (3H, d, J = 7 Hz), 0.87 (3H, d, J = 7 Hz), 0.85 (3H, d, J = 7 Hz), 0.84 (3H, d, J = 7 Hz), 0.79 (3H, d, J = 6 Hz), 0.78 (3H, d, J = 7 Hz), 0.77 (3H, d, J = 7 Hz) |
| 74 | 9.15 (1H, brd, J = 9 Hz), 7.78 (1H, brd, J = 9 HZ), 6.95 (1H, d, J = 9 Hz), 6.90 (1H, d, J = 8 Hz), 6.72 (1H, d, J = 9 Hz), 5.67 (1H, d, J = 3 Hz), 5.6-5.4 (2H, m), 5.39-5.32 (2H, m), 5.15 (1H, dd, J = 10 and 4 Hz), 5.07 (1H, dd, J = 10 and 4 Hz), 4.95-4.90 (1H, m), 5.05-4.75 (3H, m), 4.73 (1H, m), 4.57 (1H, m), 4.32 (1H, m), 4.22 (1H, m), 3.88 (1H, brs), 3.17 (3H, s), 3.06 (3H, s), 3.04 (3H, s), 2.98 (3H, s), 2.90 (3H, s), 2.76 (3H, s), 2.51 (1H, brd, J = 5 Hz), 2.4-2.3 (2H, m), 2.2-1.8 (4H, m), 1.9-0.8 (46H, m), 1.66 (3H, d, J = 6 Hz), 1.38 (3H, d, J = 7.5 Hz), 1.33 (3H, d, J = 6 Hz), 1.14 (3H, d, J = 6.5 Hz), 1.09 (3H, d, J = 7 Hz), 1.08 (3H, d, J = 6 Hz), 0.74 (3H, d, J = 7 Hz) (for a major conformer) |
| 77 | 8.93 (1H, brd, J = 9 Hz), 7.66 (1H, brd, J = 9 Hz), 6.99 (1H, d, J = 9 Hz), 6.89 (1H, d, J = 8 Hz), 6.76 (1H, d, J = 9 Hz), 5.66 (1H, d, J = 3 Hz), 5.50-5.28 (4H, m), 5.13 (1H, dd, J = 10 and 4 Hz), 5.09-4.84 (5H, m), 4.70 (1H, m), 4.53 (1H, m), 4.28-4.20 (3H, m), 3.68 (1H, brs), 3.21-3.16 (6H, s), 3.11-3.00 (10H, m), 2.96-2.89 (7H, m), 2.79 (3H, s), 2.50 (1H, brd, J = 5 Hz), 2.45-2.31 (2H, m), 2.2-1.9 (4H, m), 1.9-1.1 (10H, m), 1.65 (3H, d, J = 6 Hz), 1.40 (3H, d, J = 7.5 Hz), 1.35 (3H, d, J = 6 Hz), 1.15 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) |
| 78 | 8.93 (1H, brd, J = 9 Hz), 7.66 (1H, brd, J = 9 Hz), 6.98 (1H, d, J = 9 Hz), 6.89 (1H, d, J = 8 Hz), 6.76 (1H, d, J = 9 Hz), 5.66 (1H, d, J = 3 Hz), 5.50-5.28 (4H, m), 5.13 (1H, dd, J = 10 and 4 Hz), 5.09-4.83 (5H, m), 4.71 (1H, m), 4.54 (1H, m), 4.28-4.20 (3H, m), 3.71 (1H, brs), 3.18-3.16 (6H, s), 3.07-3.01 (9H, m), 2.91-2.89 (6H, m), 2.79 (3H, s), 2.50 (1H, brd, J = 5 Hz), 2.45-2.31 (2H, m), 2.2-1.9 (4H, m), 1.9-1.1 (10H, m), 1.66 (3H, d, J = 6 Hz), 1.38 (3H, d, J = 7.5 Hz), 1.33 (3H, d, J = 6 Hz), 1.15 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) |
| 79 | 8.54 (1H, brd, J = 9 Hz), 7.71 (1H, brd, J = 9 Hz), 6.97 (1H, d, J = 9 Hz), 6.84 (1H, d, J = 8 Hz), 6.72 (1H, d, J = 9 Hz), 5.66 (1H, d, J = 3 Hz), 5.50-5.28 (4H, m), 5.09-4.84 (6H, m), 4.71 (1H, m), 4.59-4.42 (2H, m), 4.28-4.20 (3H, m), 3.65 (1H, brs), 3.16-3.14 (5H, s), 3.12-3.05 (12H, m), 2.95-2.90 (3H, m), 2.61 (1H, brd, J = 5 Hz), 2.45-2.31 (2H, m), 2.2-1.9 (4H, m), 1.9-1.1 (10H, m), 1.65 (3H, d, J = 6 Hz), 1.40 (3H, d, J = 7.5 Hz), 1.35 (3H, d, J = 6 Hz), 1.15 (3H, d, J = 6.5 Hz), 1.25-1.21 (3H, m), 1.09 (3H, d, J = 7 Hz), 1.09 (3H, d, J = 6 Hz), 1.0-0.8 (30H, m), 0.74 (3H, d, J = 7 Hz) |
| 80 | 8.50 (1H, brd, J = 9 Hz), 7.69 (1H, brd, J = 9 Hz), 6.95 (1H, d, J = 9 Hz), 6.81 (1H, d, J = 8 Hz), 6.61 (1H, d, J = 9 Hz), 5.65 (1H, d, J = 3 Hz), 5.50-4.80 (13H, m), 5.13 (1H, dd, J = 10 and 4 Hz), 4.70 (1H, m), 4.53 (1H, m), 4.28-4.20 (3H, m), 3.71 (1H, brs), 3.22-3.04 (17H, s), 2.99-2.89 (8H, m), 2.50 (1H, brd, J = 5 Hz), 2.45-2.31 (2H, m), 2.2-1.9 (4H, m), 1.9-1.1 (10H, m), 1.65 (3H, d, J = 6 Hz), 1.40 (3H, d, J = 7.5 Hz), 1.35 (3H, d, J = 6 Hz), 1.15 (3H, d, J = 6.5 Hz), 1.09 (3H, d, J = 7 Hz), 1.09 (3H, d, J = 6 Hz), 1.0-0.8 (30H, m), 0.74 (3H, d, J = 7 Hz) |
| 81 | 9.24 (1H, d, J = 9.3 Hz), 7.57 (1H, d, J = 9.1 Hz), 6.96 (1H, d, J = 8.8 Hz), 6.89 (1H, d, J = 7.5 Hz), 6.76 (1H, d, J = 8.4 Hz), 5.68 (1H, d, J = 3.2 Hz), 5.36-5.26 (2H, m), 5.08-5.00 (1H, m), 5.00-4.75 (5H, m), 4.74-4.65 (1H, m), 4.58-4.48 (1H, m), 4.28-4.19 (2H, m), 4.19-4.14 (2H, m), 3.32 (3H, s), 3.23 (3H, s), 3.20 (3H, s), 3.06 (3H, s), 3.04 (3H, s), 3.04 (3H, s), 2.91 (3H, s), 2.49 (1H, d, J = 4.8 Hz), 2.45-1.50 (18H, m), 1.50-1.00 (4H, m), 1.41 (3H, d, J = 7.3 Hz), 1.32 (3H, d, J = 6.9 Hz), 1.11 (3H, d, J = 7.0 Hz), 1.09 (3H, d, J = 6.4 Hz), 1.08 (3H, d, J = 6.5 Hz), 1.02-0.83 (30H, m), 0.81 (3H, d, J = 6.5 Hz), 0.81 (3H, d, J = 6.5 Hz), 0.71 (3H, d, J = 6.8 Hz) (for a major isomer) |
| 82 | 9.38 (1H, d, J = 9.2 Hz), 7.51 (1H, d, J = 9.1 Hz), 6.96 (1H, d, J = 8.8 Hz), 6.86 (1H, d, J = 9.2 Hz), 6.69 (1H, d, J = 8.3 Hz), 5.67 (1H, d, J = 3.4 Hz), 5.34-5.26 (1H, m), 5.08-5.00 (1H, m), 5.00-4.75 (5H, m), 4.74-4.66 (1H, m), 4.60-4.50 (2H, m), 4.29-4.19 (2H, m), 3.75-3.70 (1H, brs), 3.31 (3H, s), 3.21 (3H, s), 3.06 (3H, s), 3.05 (3H, s), 3.03 (3H, s), 2.90 (3H, s), 2.49 (1H, d, J = 4.8 Hz), 2.45-1.90 (6H, m), 1.90-1.04 (12H, m), 1.41 (3H, d, J = 7.4 Hz), 1.32 (3H, d, J = 7.4 Hz), 1.18 (9H, s), 1.11 (3H, d, J = 6.9 Hz), 1.08 (3H, d, J = 6.2 Hz), 1.08 (3H, d, J = 6.4 Hz), 1.04-0.84 (32H, m), 0.81 (3H, d, J = 6.5 Hz), 0.71 (3H, d, J = 6.8 Hz) (for a major isomer) |
| 83 | 8.97 (1H, d, J = 9.3 Hz), 7.65 (1H, d, J = 9.0 Hz), 6.97 (1H, d, J = 8.9 Hz), 6.93 (1H, d, J = 8.8 Hz), 6.87 (1H, d, J = 7.5 Hz), 5.68 (1H, d, J = 3.4 Hz), 5.36-4.48 (12H, m), 4.26-4.16 (2H, m), 3.28 (3H, s), 3.19 (3H, s), 3.06 (9H, s), 2.92 (3H, s), 2.50-1.50 (16H, m), 1.50-1.03 (9H, m), 1.43 (3H, d, J = 7.5 Hz), 1.32 (3H, d, J = 6.8 Hz), 1.12 (3H, d, J = 6.8 Hz), 1.09 (3H, d, J = 6.5 Hz), 1.02-0.72 (30H, m), 0.81 (3H, d, J = 6.4 Hz), 0.72 (3H, d, J = 6.8 Hz) (for a major isomer) |

The structure of the compounds of the invention are shown in the following Table 44. These compounds can be easily prepared by the above preparation methods, methods described in Examples or Preparations, or methods that are well-known to one skilled in the art, or its variations.

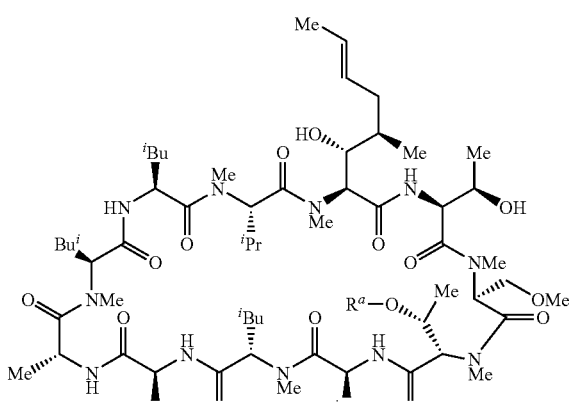

| Ex. | R$^a$ |
|---|---|
| A1 | H |
| A2 | $^t$Bu |

The invention claimed is:

1. A cyclic peptide compound of the following general formula (I):

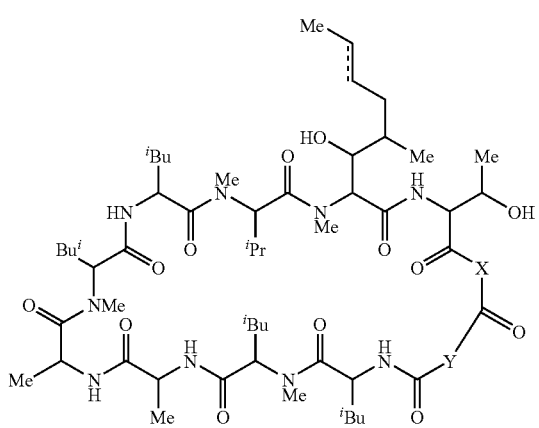

wherein
X is

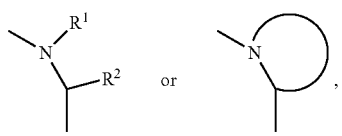

in which
R$^1$ is hydrogen or lower alkyl;
R$^2$ is hydrogen, aryl or lower alkyl which is optionally substituted by a suitable substituent selected from the group consisting of:

hydroxy, cyclo(lower)alkyl, lower alkoxy, aryl, aryl(lower)alkoxy, optionally substituted carbamoyloxy, and optionally substituted amino; and

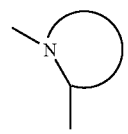

is N-containing heterocyclic group;

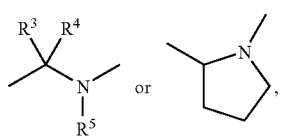

Y is
in which
R$^3$ is cyclo(lower)alkyl, aryl, optionally substituted heterocyclic group, or lower alkyl which is optionally substituted by a suitable substituent selected from the group consisting of:
hydroxy, cyclo(lower)alkyl, lower alkoxy, aryl, aryl(lower)alkoxy, lower alkoxy(lower)alkoxy, optionally substituted amino, and —OC(O)NR$^6$R$^7$ (wherein R$^6$ and R$^7$ are each independently hydrogen or lower alkyl, or alternatively R$^6$ and R$^7$, together with the nitrogen atom to which they are attached, represent N-containing heterocyclic group which is optionally substituted by a lower alkyl);
and
R$^4$ and R$^5$ are each independently hydrogen or lower alkyl;
and
--- represents single bond or double bond;
or a salt thereof,
provided that,
when R$^2$ is hydrogen, R$^3$ is cyclo(lower)alkyl, aryl, optionally substituted heterocyclic group, lower alkoxymethyl, aryl(lower)alkyl, t-butyl, sec-butyl, cyclo(lower)alkyl(lower)alkyl, or ethyl substituted by a suitable substituent selected from the group consisting of hydroxy, lower alkoxy, aryl(lower)alkoxy, lower alkoxy(lower)alkoxy, optionally substituted amino and —OC(O)NR$^6$R$^7$ (wherein R$^6$ and R$^7$ are each as defined above).

2. A compound of claim 1, wherein
X is

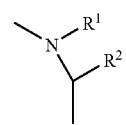

in which
R$^1$ is hydrogen or lower alkyl;
and

R² is aryl or lower alkyl which is optionally substituted by a suitable substituent selected from the group consisting of:
hydroxy, cyclo(lower)alkyl, lower alkoxy, aryl, aryl(lower)alkoxy, di(lower)alkylcarbamoyloxy, and amino which is optionally substituted by one or two suitable substituent(s) selected from the group consisting of:
lower alkyl, benzyloxycarbonyl, and t-butoxycarbonyl;
and
Y is

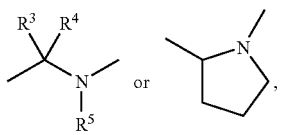

in which
R³ is cyclo(lower)alkyl, aryl, or lower alkyl which is optionally substituted by a suitable substituent selected from the group consisting of:
hydroxy, lower alkoxy, and aryl(lower)alkoxy;
R⁴ is hydrogen;
and
R⁵ is lower alkyl;
or a salt thereof.

3. A compound of claim 2,
wherein
R¹ is lower alkyl;
R² is lower alkyl;
Y is

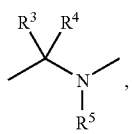

in which
R³ is aryl or lower alkyl which is optionally substituted by hydroxy or lower alkoxy;
R⁴ is hydrogen;
and
R⁵ is lower alkyl;
and
----- moiety is double bond;
or a salt thereof.

4. A compound of claim 3,
wherein
R³ is lower alkyl which is optionally substituted by hydroxy or lower alkoxy;
or a salt thereof.

5. A compound of claim 1,
wherein
X is

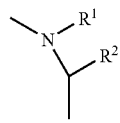

in which
R¹ is lower alkyl;
and
R² is hydrogen;
and
Y is

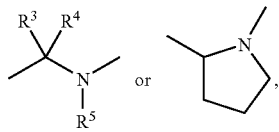

in which
R³ is cyclo(lower)alkyl, aryl, heterocyclic group which is optionally substituted by lower alkoxy carbonyl, (lower)alkoxy(lower)alkyl, aryl(lower)alkyl, t-butyl, sec-butyl, cyclo(lower)alkyl(lower)alkyl, or ethyl substituted by a suitable substituent selected from the group consisting of:
hydroxy, lower alkoxy, aryl(lower) alkoxy, lower alkoxy(lower)alkoxy, —OC(O)NR⁶R⁷ (wherein R⁶ and R⁷ are each independently hydrogen or lower alkyl, or alternatively R⁶ and R⁷, together with the nitrogen atom to which they are attached, represent N-containing heterocyclic group which is optionally substituted by a lower alkyl), and amino which is optionally substituted by one or two suitable substituent(s) selected from the group consisting of:
lower alkyl and benzyloxycarbonyl;
and
R⁴ and R⁵ are each independently hydrogen or lower alkyl;
or a salt thereof.

6. A compound of claim 5,
wherein
Y is

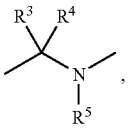

in which
R³ is cyclo(lower)alkyl, aryl, heterocyclic group which is optionally substituted by lower alkoxy carbonyl, t-butyl, sec-butyl, or ethyl substituted by a suitable substituent selected from the group consisting of:
hydroxy, lower alkoxy, aryl(lower)alkoxy, lower alkoxy(lower)alkoxy, and —OC(O)NR⁶R⁷

(wherein R⁶ and R⁷ are each independently hydrogen or lower alkyl, or alternatively R⁶ and R⁷, together with the nitrogen atom to which they are attached, represent N-containing heterocyclic group which is optionally substituted by a lower alkyl);

R⁴ is hydrogen
and
R⁵ is lower alkyl;
and
----- moiety is double bond;
or a salt thereof.

7. A compound of claim 1 wherein
X is

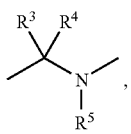

and
Y is

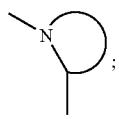

in which
R³ is lower alkyl;
and
R⁴ and R⁵ are each independently hydrogen or lower alkyl;
or a salt thereof.

8. A compound of claim 7, wherein
X is

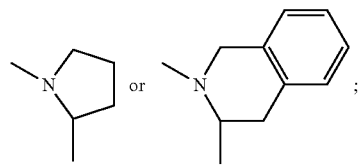

R⁴ is hydrogen;
R⁵ is lower alkyl;
and
----- moiety is double bond;
or a salt thereof.

9. A pharmaceutical composition which comprises, as an active ingredient, a compound of claim 1 or a pharmaceutically acceptable salt thereof in admixture with pharmaceutically acceptable carriers or excipients.

10. A process of manufacturing a medicament comprising admixing a compound of claim 1 or a pharmaceutically acceptable salt thereof with at least one pharmaceutically acceptable carrier or excipient.

11. A compound of claim 1, wherein the compound is

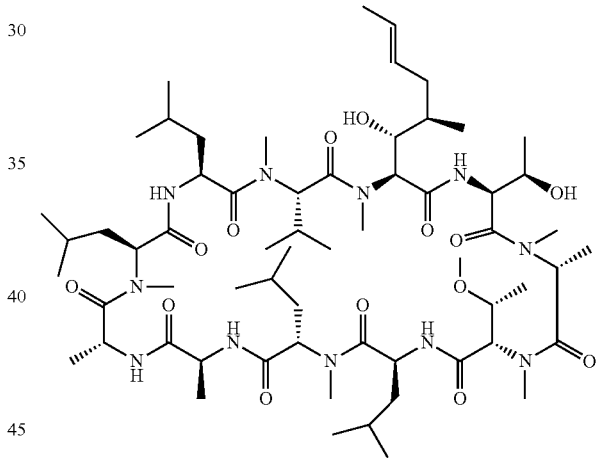

or a salt thereof.

* * * * *